US008829164B2

(12) United States Patent
Whalen et al.

(10) Patent No.: US 8,829,164 B2
(45) Date of Patent: Sep. 9, 2014

(54) ANTI-RON ANTIBODIES

(71) Applicant: AVEO Pharmaceuticals, Inc., Cambridge, MA (US)

(72) Inventors: Kerry Whalen, Chelmsford, MA (US); Steve Bottega, Cambridge, MA (US); Andrea Boudrow, Peabody, MA (US); Lyne Breault, Roslindale, MA (US); Ting Chen, Acton, MA (US); James Gifford, Somerville, MA (US); May Han, Brookline, MA (US); Jinwei Jiang, Chestnut Hill, MA (US); Lorena Lerner, Newton Centre, MA (US); Qing Liu, Acton, MA (US); Kristan Meetze, Lexington, MA (US); Sylvie Vincent, Somerville, MA (US); Solly Weiler, Newton, MA (US); William M. Winston, Jr., Marlborough, MA (US); Jeno Gyuris, Lincoln, MA (US)

(73) Assignee: AVEO Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/070,070

(22) Filed: Nov. 1, 2013

(65) Prior Publication Data

US 2014/0066603 A1 Mar. 6, 2014

Related U.S. Application Data

(62) Division of application No. 13/177,071, filed on Jul. 6, 2011, now Pat. No. 8,603,478.

(60) Provisional application No. 61/466,679, filed on Mar. 23, 2011, provisional application No. 61/361,808, filed on Jul. 6, 2010.

(51) Int. Cl.
*C07K 16/30* (2006.01)

(52) U.S. Cl.
USPC ........................ 530/387.3; 530/389.7

(58) Field of Classification Search
None
See application file for complete search history.

(56) References Cited

U.S. PATENT DOCUMENTS

| | | | |
|---|---|---|---|
| 5,707,624 | A | 1/1998 | Nickoloff et al. |
| 7,235,523 | B2 | 6/2007 | Waltz et al. |
| 7,498,416 | B2 | 3/2009 | Yayon et al. |
| 2009/0136510 | A1 | 5/2009 | Pereira et al. |
| 2009/0202547 | A1 | 8/2009 | Yayon et al. |
| 2009/0226442 | A1 | 9/2009 | Huet et al. |

FOREIGN PATENT DOCUMENTS

| | | |
|---|---|---|
| WO | WO-2005/120557 A2 | 12/2005 |
| WO | WO-2006/020258 A2 | 2/2006 |
| WO | WO-2008/100624 A2 | 8/2008 |
| WO | WO-2009/070294 A2 | 6/2009 |
| WO | WO-2009/094148 A2 | 7/2009 |
| WO | WO-2009/134776 A2 | 11/2009 |
| WO | WO-2010/037835 A2 | 4/2010 |
| WO | WO-2011/090761 A1 | 7/2011 |

OTHER PUBLICATIONS

Burgess et al. (2006) "Fully Human Monoclonal Antibodies to Hepatocyte Growth Factor with Therapeutic Potential against Hepatocyte Growth Factor/c-Met-Dependent Human Tumors" Cancer Res. 66:1721-1729.

Camp et al. (2007) "Tyrosine Kinase Receptor RON in Human Pancreatic Cancer—Expression, Function, and Validation as a Target" Cancer 109:1030-1039.

Carter (2006) "Potent Antibody Therapeutics by Design" Nature Reviews. Immunology 6:343-357.

Han et al. (2010) "Anti-tumor activity of anti-RON antibodies and biomarker of response" European Journal of Cancer. Supplement. Nov. 18, 2010, Plenary Session 6. Proffered papers. Abstract 2LB.

Hayden-Ledbetter et al. (2009) "CD20-Directed Small Modular Immunopharmaceutical, TRU-015, Depletes Normal and Malignant B Cells" Clin. Cancer Res. 15:2739-2746.

Lu et al. (2007) "Multiple variants of the RON receptor tyrosine kinase: Biochemical properties, tumorigenic activities, and potential drug targets" Cancer Lett. 257:157-164.

Montero-Julian et al. (1998) "Characterization of Two Monoclonal Antibodies Against the RON Tyrosine Kinase Receptor" Hybridoma 17:541-551.

O'Toole et al. (2006) "Therapeutic Implications of a Human Neutralizing Antibody to the Macrophage-Stimulating Protein Receptor Tyrosine Kinase (RON), a c-MET Family Member" Cancer Research 66:9162-9170.

Qian et al. (2009) "Inhibition of Tumor Cell Growth, Invasion, and Metastasis by EXEL-2880 (XL880, GSK1363089), a Novel Inhibitor of HGF and VEGF Receptor Tyrosine Kinases" Cancer Res. 69:8009-8016.

Raeppel et al. (2010) "Identification of a novel series of potent RON receptor tyrosine kinase inhibitors" Bioorg Med Chem Lett 20:2745-9.

Rampino et al. (2007) "Neutralization of macrophage-stimulating protein ameliorates renal injury in anti-thy 1 glomerulonephritis" Journal of the American Society of Nephrology 18:1486-1496.

(Continued)

*Primary Examiner* — Brian J Gangle
*Assistant Examiner* — Andrea McCollum
(74) *Attorney, Agent, or Firm* — Goodwin Procter LLP

(57) ABSTRACT

Monoclonal antibodies that bind and inhibit activation of human RON (Recepteur d'Origine Nantais) are disclosed. The antibodies can be used to treat certain forms of cancer that are associated with activation of RON.

11 Claims, 19 Drawing Sheets

(56) References Cited

OTHER PUBLICATIONS

Schroeder et al. (2009) "Discovery of N-(4-(2-Amino-3-chloropyridin-4-yloxy)-3-fluorophenyl)-4-ethoxy-1-(4-fluorophenyl)-2-oxo-1,2-dihydropyridine-3-carboxamide (BMS-777607), a Selective and Orally Efficacious Inhibitor of the Met Kinase Superfamily" J. Med Chem. 52:1251-1254.

Secco et al. (2004) "Characterization of a single-chain intrabody directed against the human receptor tyrosine kinase Ron" Journal of Immunological Methods 285:99-109.

Wagh et al. (2008) "Met Related Receptor Tyrosine Kinase Ron in Tumor Growth and Metastasis" Adv. Cancer Res. 100:1-33.

Wark et al. (2006) "Latest technologies for the enhancement of antibody affinity" Advanced Drug Delivery Reviews 58:657-670.

Yao et al. (2006) "Agonistic Monoclonal Antibodies Potentiate Tumorigenic and Invasive Activities of Splicing Variant of the RON Receptor Tyrosine Kinase" Cancer Biology and Therapy 5:1179-1186.

Zhang et al. (2008) "Identification of a Novel Recepteur d'Origine Nantais/c-Met Small-Molecule Kinase Inhibitor with Antitumor Activity In vivo" Cancer Res. 68:6680-6687.

Zhao et al. (2007) "Targeting CD37-positive lymphoid malignancies with a novel engineered small modular immunopharmaceutical" Blood 110:2569-2577.

Product insert for Human MSP R/Ron Antibody; Monoclonal Mouse IgG1 Clone #99211; Catalog No. MAB691 (R&D Systems) (1 page) (2010).

International Search Report and Written Opinion, International Patent Application No. PCT/US2011/043056, mailed on Jan. 24, 2012 (27 pages).

Complete Heavy Chain Variable Region Amino Acid Alignments

| Antibody | | CDR1 | CDR2 |
|---|---|---|---|
| 07F01 | (1) | EVKLLESGGGLVQPGGSLKLSCAASGFDFSRHMSWVRLAPGKGLEWIAEINPDSRTINYTPSLKEKFII |
| 12B11 | (1) | EVQLVESGGGLVKPGGSLKLSCAASGFTFSTYAMSWIRQTPEKRLEWVAGITNGGSFTYYPDTVKGRFTI |
| 17F06 | (1) | EVKLVESGGGLVKPGASLKLSCAASGFIFSSYGMSWVRQTSDKRLEWVASISSGGTTYLDTVKGRFTI |
| 18H09 | (1) | EVQLQESGPSLVKPSQTLSLTCYVTGDSITSDYWNWIRKFPGNKLEYMGYIS-YSGSTYYNPSLKSRISI |
| 29B06 | (1) | EVQLQESGPSLVKPSQTLSLTCSVTGDSITSGYWNWIRKFPGNKLEYMGYIS-YSGKTYYNPSLKSRISI |

| | | CDR3 | |
|---|---|---|---|
| 07F01 | (71) | SRDNAKNSLFLQMNRVRSEDTALYYCARRVRIHYYGAMDCWGQGTSVTVSS | (SEQ ID NO: 2) |
| 12B11 | (71) | SRDNARNILYLQMSGLRSEDTAMYYCARQGYYGVNF---DYWGQGTTLTVSS | (SEQ ID NO: 12) |
| 17F06 | (71) | SRENAKDTLYLQMSGLKSEDTALYYCTRGQWLLKF----AYWGQGTLVTVSA | (SEQ ID NO: 22) |
| 18H09 | (70) | TRDTSKNQFYLRLNSVTTEDTATYYCARTHILTI-----AYWGQGTLVTVSA | (SEQ ID NO: 32) |
| 29B06 | (70) | TRDTSKNHYLQLISVTAEDTATYYCARSKYDYAM----DYWGQGTSVTVSS | (SEQ ID NO: 42) |

Fig.2

Heavy Chain CDR Amino Acid Alignments

| Antibody | CDR1 | | CDR2 | | CDR3 | |
|---|---|---|---|---|---|---|
| 07F01 | RHWMS | (SEQ ID NO: 5) | EINPDSRTINYTPSLKE | (SEQ ID NO: 6) | RVRIHYYGAMDC | (SEQ ID NO: 7) |
| 12B11 | TYAMS | (SEQ ID NO: 15) | GITNGGSFTYPDTVKG | (SEQ ID NO: 16) | QGYYGVNF---DY | (SEQ ID NO: 17) |
| 17F06 | SYGMS | (SEQ ID NO: 25) | SISSGGGTTYYLDTVKG | (SEQ ID NO: 26) | GQWLLKF----AY | (SEQ ID NO: 27) |
| 18H09 | SDYWN | (SEQ ID NO: 35) | YIS-YSGSTYNPSLKS | (SEQ ID NO: 36) | THILTI------AY | (SEQ ID NO: 37) |
| 29B06 | SGYWN | (SEQ ID NO: 45) | YIS-YSGKTYNPSLKS | (SEQ ID NO: 46) | SKYDYAM---DY | (SEQ ID NO: 47) |

Fig.3

Complete Light (Kappa or Lambda) Chain Variable Region Amino Acid Alignments

| Antibody | | CDR1 | CDR2 |
|---|---|---|---|
| 07F01 | (1) | DIVLTQSQKIVSTSVGARVSVTCKASQ-----NVGSSLVWYQQKPGQSPKTLIY | SASFR----YSGVPDR |
| 12B11 | (1) | DAVMTQTPLSLPVSLGDQASISCRSSQSLENSNGNTYLNWYLQKPGQSPQLLIY | RVSNR----FSGVPDR |
| 17F06 | (1) | QLVLTQSSS-ASFSLGASAKLTCTLSSQ-----HTTYTIEWYQQLPLKPPKYVME | LKKDGSHSTGVGIPDR |
| 18H09 | (1) | QAVVTQESA-LTTSPGETVTLTCRSSAGAV--TTSNFANWVQEKPDHLFTGLIG | DTNIR----APGVPAR |
| 29B06 | (1) | DIVLTQSPASLAVSLGQRATISCRASEIVDN-FGISFMNWFQQKPGQPPKLLIY | AASNQ----GSVPAR |

| | | CDR3 | | |
|---|---|---|---|---|
| 07F01 | (62) | FTGSGSGTDFTLTISNVQSEDLADYFCQQYNNYP----LTFGAGTKLELK | (SEQ ID NO: 4) |
| 12B11 | (67) | FSGSGSGTDFTLKIIRVEAEDLGLYFCLQVTHVP----HTFGGGTKLELK | (SEQ ID NO: 14) |
| 17F06 | (66) | FSGSSSGADRYLTISNIQPEDEAIYICGVGETIEDQFYYVFGGGTKVTVL | (SEQ ID NO: 24) |
| 18H09 | (64) | FSGSLIGDKAALTITGAQTEDEAIYFCALWYSNHY----WVFGGGTKLTVL | (SEQ ID NO: 34) |
| 29B06 | (66) | FSGSGSGTDFSLNIHPVEEDDTAMYFCQQSKEVP----PTFGGGTKLEIK | (SEQ ID NO: 44) |

Fig.4

Light (Kappa or Lambda) Chain CDR Amino Acid Alignments

| Antibody | CDR1 | | CDR2 | | CDR3 | |
|---|---|---|---|---|---|---|
| 07F01 | KASQ-----NVGSSLV | (SEQ ID NO: 8) | SASFR----YS | (SEQ ID NO: 9) | QQYNNYP----LT | (SEQ ID NO: 10) |
| 12B11 | RSSQSLENSNGNTYLN | (SEQ ID NO: 18) | RVSNR----FS | (SEQ ID NO: 19) | LQVTHVP----HT | (SEQ ID NO: 20) |
| 17F06 | TLSSQ----HTTYTIE | (SEQ ID NO: 28) | LKKDGSHSTGV | (SEQ ID NO: 29) | GVGETIEDQFVYV | (SEQ ID NO: 30) |
| 18H09 | RSSAGAV--TTSNFAN | (SEQ ID NO: 38) | DTNIR----AP | (SEQ ID NO: 39) | ALWYSNHY---WV | (SEQ ID NO: 40) |
| 29B06 | RASEIVDN-FGISFMN | (SEQ ID NO: 48) | AASNQ----GS | (SEQ ID NO: 49) | QQSKEVP----PT | (SEQ ID NO: 50) |

Fig.5

Complete Heavy Chain Variable Region Amino Acid Alignments

| Antibody | | CDR1 | CDR2 |
|---|---|---|---|
| 07F01 | EVKLLESGGGLVQPGGSLKLSCAASGFDFS | RHWMS | WVRLAPGKGLEWIA EINPDSRTINYTPSLKEKFII |
| Chimeric 07F01 C102S | EVKLLESGGGLVQPGGSLKLSCAASGFDFS | RHWMS | WVRLAPGKGLEWIA EINPDSRTINYTPSLKEKFII |
| Sh07F01 Hv3-48 | EVQLVESGGGLVQPGGSLRLSCAASGFDFS | RHWMS | WVRQAPGKGLEWVS EINPDSRTINYTPSLKERFTI |
| Sh07F01 Hv3-48 D28T T60A L63V E65G | EVQLVESGGGLVQPGGSLRLSCAASGFTFS | RHWMS | WVRQAPGKGLEWVS EINPDSRTINYAPSVKGRFTI |

| | CDR3 | |
|---|---|---|
| 07F01 | SRDNAKNSLFLQMNRVRSEDTALYYCAR | RVRIHYYGAMDC WGQGTSVTVSS (SEQ ID NO: 2) |
| Chimeric 07F01 C102S | SRDNAKNSLFLQMNRVRSEDTALYYCAR | RVRIHYYGAMDS WGQGTSVTVSS (SEQ ID NO: 133) |
| Sh07F01 Hv3-48 | SRDNAKNSLYLQMNSLRAEDTAVYYCAR | RVRIHYYGAMDS WGQGTTVTVSS (SEQ ID NO: 135) |
| Sh07F01 Hv3-48 D28T T60A L63V E65G | SRDNAKNSLYLQMNSLRAEDTAVYYCAR | RVRIHYYGAMDS WGQGTTVTVSS (SEQ ID NO: 137) |

Fig. 12A

| Antibody | | CDR1 | CDR2 |
|---|---|---|---|
| 29B06 | EVQLQESGPSLVKPSQTLSLTCSVTGDSIT | SGYWN | WIRKFPGNKLEYMG YISYSGKTYYNPSLKSRISIT |
| Sh29B06_Hv4-59 | QVQLQESGPGLVKPSETLSLTCTVSGGSIS | SGYWN | WIRQPPGKGLEWIG YISYSGKTYYNPSLKSRVTIS |
| Hu29B06 Hv4-59 | QVQLQESGPGLVKPSETLSLTCTVSGGSIT | SGYWN | WIRKPPGKGLEWIG YISYSGKTYYNPSLKSRITIS |
| Hu29B06 Hv4-59 D27G T30S M48I I67V Y78F | QVQLQESGPGLVKPSETLSLTCTVSGGSIS | SGYWN | WIRKPPGKKLEYIG YISYSGKTYYNPSLKSRVTIS |

| | CDR3 | |
|---|---|---|
| 29B06 | RDTSKNHYLQLISVTAEDTATYYCAR | SKYDYAMDY WGQGTSVTVSS (SEQ ID NO: 42) |
| Sh29B06_Hv4-59 | VDTSKNQFSLKLSSVTAADTAVYYCAR | SKYDYAMDY WGQGTLVTVSS (SEQ ID NO: 143) |
| Hu29B06 Hv4-59 | RDTSKNQYSLKLSSVTAADTAVYYCAR | SKYDYAMDY WGQGTLVTVSS (SEQ ID NO: 145) |
| Hu29B06 Hv4-59 D27G T30S M48I I67V Y78F | RDTSKNQFSLKLSSVTAADTAVYYCAR | SKYDYAMDY WGQGTLVTVSS (SEQ ID NO: 147) |

Fig. 12B

Heavy Chain CDR Amino Acid Alignments

| Antibody | CDR1 | CDR2 | CDR3 |
|---|---|---|---|
| 07F01 | RHWMS (SEQ ID NO: 5) | EINPDSRTINYTPSLKE (SEQ ID NO: 6) | RVRIHYYGAMDC (SEQ ID NO: 7) |
| Chimeric 07F01 C102S | RHWMS (SEQ ID NO: 5) | EINPDSRTINYTPSLKE (SEQ ID NO: 6) | RVRIHYYGAMDS (SEQ ID NO: 123) |
| Sh07F01 Hv3-48 | RHWMS (SEQ ID NO: 5) | EINPDSRTINYTPSLKE (SEQ ID NO: 6) | RVRIHYYGAMDS (SEQ ID NO: 123) |
| Sh07F01 Hv3-48 D28T T60A L63V E65G | RHWMS (SEQ ID NO: 5) | EINPDSRTINYAPSVKG (SEQ ID NO: 122) | RVRIHYYGAMDS (SEQ ID NO: 123) |

Fig. 13A

| Antibody | CDR1 | CDR2 | CDR3 |
|---|---|---|---|
| 29B06 | SGYWN (SEQ ID NO: 45) | YISYSGKTYYNPSLKS (SEQ ID NO: 46) | SKYDYAMDY (SEQ ID NO: 47) |
| Sh29B06_Hv4-59 | SGYWN (SEQ ID NO: 45) | YISYSGKTYYNPSLKS (SEQ ID NO: 46) | SKYDYAMDY (SEQ ID NO: 47) |
| Hu29B06 Hv4-59 | SGYWN (SEQ ID NO: 45) | YISYSGKTYYNPSLKS (SEQ ID NO: 46) | SKYDYAMDY (SEQ ID NO: 47) |
| Hu29B06 Hv4-59 D27G T30S M48I I67V Y78F | SGYWN (SEQ ID NO: 45) | YISYSGKTYYNPSLKS (SEQ ID NO: 46) | SKYDYAMDY (SEQ ID NO: 47) |

Fig. 13B

Complete Light (Kappa) Chain Variable Region Amino Acid Alignments

| Antibody | CDR1 | CDR2 |
|---|---|---|

```
                              CDR1                              CDR2
07F01       DIVLTQSQKIVSTSVGARVSVTC KASQNVGSSLVW YQQKPGQSPKTLIY SASFRYS GVPDRFTGSGSGTD
HE L 07F01 Kv1-9    DIQLTQSQSFVSTSVGDRVTVTC RASQNVGSSLVW YQQKPGKSPKTLIY SASFLYS GVPSRFSGSGSGTE
Sh07F01 Kv1-9 F1    DIQLTQSPSFLSASVGDRVTITC RASQNVGSSLVW YQQKPGKAPKTLIY SASFLYS GVPSRFSGSGSGTE

CDR3
07F01       FTLTISNVQSEDLADYFC QQYNNYPLT FGAGTKLELK    (SEQ ID NO: 4)
HE L 07F01 Kv1-9    FTLTISSVQPEDFADYFC QQYNNYPLT FGGGTKVEIK    (SEQ ID NO: 139)
Sh07F01 Kv1-9 F1    FTLTISSLQPEDFATYYC QQYNNYPLT FGGGTKVEIK    (SEQ ID NO: 141)
```

Fig. 14A

```
                              CDR1                              CDR2
29B06       DIVLTQSPASLAVSLGQRATISC RASEIVDNFGISFMNW FQQKPGQPPKLLIY AASNQGS GVPARFSGSG
Sh29B06 Kv2-28  DIVMTQSPLSLPVTPGEPASISC RASEIVDNFGISFMNW YLQKPGQSPQLLIY AASNQGS GVPDRFSGSG

CDR3
29B06       SGTDFSLNIHPVEEDDTAMYFC QQSKEVPPT FGGGTKLEIK    (SEQ ID NO: 44)
Sh29B06 Kv2-28  SGTDFTLKISRVEAEDVGVYYC QQSKEVPPT FGGGTKVEIK    (SEQ ID NO: 149)
```

Fig. 14B

Light (Kappa) Chain CDR Amino Acid Alignments

| Antibody | CDR1 | CDR2 | CDR3 |
|---|---|---|---|
| 07F01 | KASQNVGSSLV (SEQ ID NO: 8) | SASFRYS (SEQ ID NO: 9) | QQYNNYPLT (SEQ ID NO: 10) |
| HE L 07F01 Kv1-9 | RASQNVGSSLV (SEQ ID NO: 130) | SASFLYS (SEQ ID NO: 131) | QQYNNYPLT (SEQ ID NO: 10) |
| Sh07F01 Kv1-9 F1 | RASQNVGSSLV (SEQ ID NO: 130) | SASFLYS (SEQ ID NO: 131) | QQYNNYPLT (SEQ ID NO: 10) |

Fig. 15A

| Antibody | CDR1 | CDR2 | CDR3 |
|---|---|---|---|
| 29B06 | RASEIVDNFGISFMN (SEQ ID NO: 48) | AASNQGS (SEQ ID NO: 49) | QQSKEVPPT (SEQ ID NO: 50) |
| Sh29B06 Kv2-28 | RASEIVDNFGISFMN (SEQ ID NO: 48) | AASNQGS (SEQ ID NO: 49) | QQSKEVPPT (SEQ ID NO: 50) |

Fig. 15B

ANTI-RON ANTIBODIES

CROSS-REFERENCE TO RELATED APPLICATIONS

This application is a divisional of U.S. patent application Ser. No. 13/177,071, filed Jul. 6, 2011, which claims the benefit of and priority to U.S. Provisional Application No. 61/466,679, filed Mar. 23, 2011, and U.S. Provisional Application Ser. No. 61/361,808, filed Jul. 6, 2010; the contents of each application are hereby incorporated by reference in their entirety.

FIELD OF THE INVENTION

The field of the invention is molecular biology, immunology and oncology. More particularly, the field is therapeutic antibodies.

BACKGROUND

Recepteur d'Origine Nantais (RON), also known as Macrophage Stimulating Protein Receptor (MSP R, or MST1-R), is a member of the MET family of receptor tyrosine kinases that binds the ligand known as Macrophage Stimulating Protein (MSP). RON is composed of a 40 kDa extracellular α chain and a 150 kDa transmembrane β chain. The β chain is responsible for the intrinsic kinase activity, and the extracellular portions of the two chains function together as the ligand binding domain (Wagh et al., 2008, ADV. CANCER RES. 100:1-33).

MSP binding to RON activates multiple downstream signaling pathways and mediates multiple cellular activities. RON pathway dysregulation is involved in inflammatory response, wound healing and liver regeneration. RON signaling can sustain tumor growth, survival, motility, invasion and angiogenesis in certain malignancies. The RON protein exists in several splice variants, some of which are tumorigenic in animal models of cancer. One such splice variant is delta 160 RON, which lacks exons 5 and 6 (Lu et al., 2007, CANCER LETT. 257:157-164).

When activated by ligand binding, RON activates the PI3K/AKT pathway and the MAPK pathway. RON also affects cells through interactions with other receptors, e.g., c-Met, integrins and EGFR. To date, no activating mutations in RON exons have been reported. Alternative splicing and overexpression appear to be the main mechanisms for constitutive activation of the receptor. Several small molecule inhibitors have been reported that inhibit multiple receptor tyrosine kinases, including RON, examples of which include EXCEL-2880, (Qian et al., 2009, CANCER RES. 69:8009-8016) and BMS-77607 (Schroeder et al., 2009 J. MED CHEM. 52:1251-1254). A dual c-met/RON inhibitor has also been reported, Amgen compound I (Zhang et al., 2008, CANCER RES. 68:6680-6687). A recent publication describes a selective RON small molecule inhibitor (Raeppel et al., 2010 BIOORG MED CHEM LETT 20:2745-9). Several antibodies that inhibit human RON activity have been reported (Huet et al., US 2009/0226442; Pereira et al., US 2009/0136510; Zhu et al., WO 2006/020258; Pereira et al., WO 2005/120557; and commercial antibody MAB691, R&D Systems, Minneapolis, Minn.).

Naturally occurring antibodies are multimeric proteins that contain four polypeptide chains (FIG. 1). Two of the polypeptide chains are called heavy chains (H chains), and two of the polypeptide chains are called light chains (L chains). The immunoglobulin heavy and light chains are connected by an interchain disulfide bond. The immunoglobulin heavy chains are connected by interchain disulfide bonds. A light chain consists of one variable region ($V_L$ in FIG. 1) and one constant region ($C_L$ in FIG. 1). The heavy chain consists of one variable region ($V_H$ in FIG. 1) and at least three constant regions ($CH_1$, $CH_2$ and $CH_3$ in FIG. 1). The variable regions determine the specificity of the antibody. Each variable region comprises three hypervariable regions also known as complementarity determining regions (CDRs) flanked by four relatively conserved framework regions (FRs). The three CDRs, referred to as $CDR_1$, $CDR_2$, and $CDR_3$, contribute to the antibody binding specificity. Naturally occurring antibodies have been used as starting material for engineered antibodies, such as chimeric antibodies and humanized antibodies.

Although antibodies that bind RON are known in the art, there is still a need for improved RON antibodies that can be used as therapeutic agents.

SUMMARY

The invention is based, in part, upon the discovery of a family of antibodies that specifically bind human RON. The antibodies contain RON binding sites based on the CDRs of the antibodies. The antibodies can be used as therapeutic agents. When used as therapeutic agents, the antibodies are engineered, e.g., humanized, to reduce or eliminate an immune response when administered to a human patient.

The antibodies prevent or inhibit the activation of (i.e., neutralize) human RON. In some embodiments, the antibodies prevent RON from binding to its ligand, MSP, thereby neutralizing RON activity. In certain embodiments, the antibodies prevent RON activation without inhibiting RON binding to MSP. The antibodies can be used to inhibit the downstream signaling of the breast tumor cell line T47D. Furthermore, when administered to a mammal, the antibodies can inhibit or reduce tumor growth in the mammal.

These and other aspects and advantages of the invention will become apparent upon consideration of the following figures, detailed description, and claims. As used herein, "including" means without limitation, and examples cited are non-limiting.

DESCRIPTION OF THE DRAWINGS

The invention can be more completely understood with reference to the following drawings.

FIG. 2 is a sequence alignment showing the amino acid sequence of the complete immunoglobulin heavy chain variable region of antibodies 07F01, 12B11, 17F06, 18H09 and 29B06. The amino acid sequences for each antibody are aligned against one another, and $CDR_1$, $CDR_2$, and $CDR_3$, are identified in boxes. The unboxed sequences represent framework (FR). Alignment positioning (gaps) are based on Kabat numbering, rather than an alignment algorithm such as Clustal sequences.

FIG. 3 is a sequence alignment showing the $CDR_1$, $CDR_2$, and $CDR_3$ sequences for each of the immunoglobulin heavy chain variable region sequences in FIG. 2.

FIG. 4 is a sequence alignment showing the amino acid sequence of the complete immunoglobulin light chain variable region of antibodies 07F01, 12B11, 17F06, 18H09 and 29B06. The amino acid sequences for each antibody are aligned against one another, and $CDR_1$, $CDR_2$, and $CDR_3$, are identified in boxes. The unboxed sequences represent framework (FR) sequences. Alignment positioning (gaps) are based on Kabat numbering, rather than an alignment algorithm such as Clustal sequences.

FIG. 5 is a sequence alignment showing the $CDR_1$, $CDR_2$, and $CDR_3$ sequences for each of the immunoglobulin light chain variable region sequences in FIG. 4.

FIG. 12A is a schematic diagram showing the amino acid sequences of the complete immunoglobulin heavy chain variable region of 07F01 (SEQ ID NO: 2) and the complete heavy chain variable regions denoted as Chimeric 07F01 C102S (SEQ ID NO: 133), Sh07F01 Hv3-48 (SEQ ID NO: 135), and Sh07F01 Hv3-48 D28T T60A L63V E65G (SEQ ID NO: 137). The amino acid sequences for each heavy chain variable region are aligned against one another, and Complementary Determining Sequences (CDR) (Kabat definition), $CDR_1$, $CDR_2$, and $CDR_3$, are identified in boxes. The unboxed sequences represent framework (FR) sequences.

FIG. 12B is a schematic diagram showing the amino acid sequences of the complete immunoglobulin heavy chain variable region of 29B06 (SEQ ID NO: 42) and the complete heavy chain variable regions denoted as Sh29B06_Hv4-59 (SEQ ID NO: 143), Hu29B06 Hv4-59 (SEQ ID NO: 145), and Hu29B06 Hv4-59 D27G T30S M48I I67V Y78F (SEQ ID NO: 147). The amino acid sequences for each heavy chain variable region are aligned against one another, and $CDR_1$, $CDR_2$, and $CDR_3$ sequences (Kabat definition) are identified in boxes. The unboxed sequences represent framework (FR) sequences.

FIG. 13A is a schematic diagram showing the $CDR_1$, $CDR_2$, and $CDR_3$ sequences (Kabat definition) for each of the variable region sequences shown in FIG. 12A.

FIG. 13B is a schematic diagram showing the $CDR_1$, $CDR_2$, and $CDR_3$ sequences (Kabat definition) for each of the variable region sequences shown in FIG. 12B.

FIG. 14A is a schematic diagram showing the amino acid sequences of the complete light chain variable region of 07F01 (SEQ ID NO: 4) and the complete light chain variable regions denoted as HE L 07F01 Kv1-9 (SEQ ID NO: 139) and Sh07F01 Kv1-9 F1 (SEQ ID NO: 141). The amino acid sequences for each light chain variable region are aligned against one another, and $CDR_1$, $CDR_2$, and $CDR_3$ sequences (Kabat definition) are identified in boxes. The unboxed sequences represent framework (FR) sequences.

FIG. 14B is a schematic diagram showing the amino acid sequences of the complete light chain variable region of 29B06 (SEQ ID NO: 44) and the complete light chain variable region denoted as Sh29B06 Kv2-28 (SEQ ID NO: 149). The amino acid sequences for each light chain variable region are aligned against one another, and $CDR_1$, $CDR_2$, and $CDR_3$ sequences (Kabat definition) are identified in boxes. The unboxed sequences represent framework (FR) sequences.

FIG. 15A is a sequence alignment showing the $CDR_1$, $CDR_2$, and $CDR_3$ sequences (Kabat definition) for each of the variable region sequences shown in FIG. 14A.

FIG. 15B is a sequence alignment showing the $CDR_1$, $CDR_2$, and $CDR_3$ sequences (Kabat definition) for each of the variable region sequences shown in FIG. 14B.

DETAILED DESCRIPTION

Figure 1:
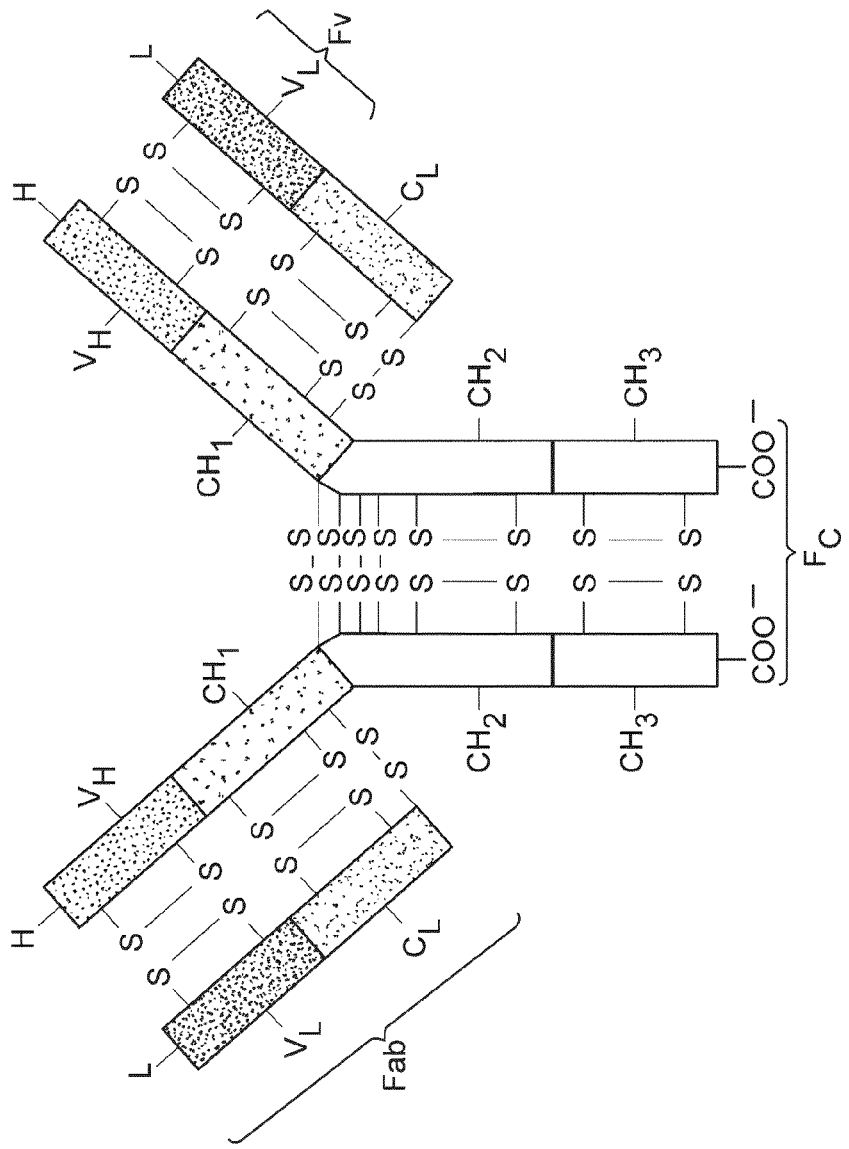
FIG. 1 (prior art) is a schematic representation of a typical naturally-occurring antibody.

The anti-RON antibodies disclosed herein are based on the antigen binding sites of certain monoclonal antibodies that have been selected on the basis of binding and neutralizing the activity of human RON. The antibodies contain immunoglobulin variable region CDR sequences that define a binding site for human RON.

In view of the neutralizing activity of these antibodies, they are useful for modulating the growth and/or proliferation of certain types of cancer cells. When used as a therapeutic agent, the antibodies can be engineered to minimize or eliminate an immune response when administered to a human patient. In some embodiments, the antibodies are fused or conjugated to other moieties, such as effector molecules (e.g., other proteins or small molecule therapeutics), a detectable label or a toxin moiety. Various features and aspects of the invention are discussed in more detail below.

As used herein, unless otherwise indicated, the term "antibody" means an intact antibody (e.g., an intact monoclonal antibody) or antigen-binding fragment of an antibody (e.g., an antigen-binding fragment of a monoclonal antibody), including an intact antibody or antigen-binding fragment that has been modified, engineered or chemically conjugated, or that is a human antibody. Examples of antibodies that have been modified or engineered are chimeric antibodies, humanized antibodies, and multispecific antibodies (e.g., bispecific antibodies). Examples of antigen-binding fragments include Fab, Fab', F(ab')$_2$, Fv, single chain antibodies (e.g., scFv), minibodies and diabodies. An antibody conjugated to a toxin moiety is an example of a chemically conjugated antibody.

I. Antibodies that Bind RON

The antibodies disclosed herein comprise: (a) an immunoglobulin heavy chain variable region comprising the structure CDR$_{H1}$-CDR$_{H2}$-CDR$_{H3}$ and (b) an immunoglobulin light chain variable region comprising the structure CDR$_{L1}$-CDR$_{L2}$-CDR$_{L3}$, wherein the heavy chain variable region and the light chain variable region together define a single binding site for binding human RON protein.

In some embodiments, the antibody comprises: (a) an immunoglobulin heavy chain variable region comprising the structure CDR$_{H1}$-CDR$_{H2}$-CDR$_{H3}$ and (b) an immunoglobulin light chain variable region, wherein the heavy chain variable region and the light chain variable region together define a single binding site for binding human RON. A CDR$_{H1}$ comprises an amino acid sequence selected from the group consisting of SEQ ID NO: 5 (07F01), SEQ ID NO: 51 (07F01), SEQ ID NO: 124 (Sh07F01 Hv3-48 D28T T60A L63V E65G), SEQ ID NO: 15 (12B11), SEQ ID NO: 53 (12B11), SEQ ID NO: 25 (17F06), SEQ ID NO: 55 (17F06), SEQ ID NO: 35 (18H09), SEQ ID NO: 57 (18H09), SEQ ID NO: 45 (29B06), SEQ ID NO: 59 (29B06), and SEQ ID NO: 126 (Sh29B06 Hv4-59, Hu29B06 Hv4-59 D27G T30S M48I I67V Y78F); a CDR$_{H2}$ comprises an amino acid sequence selected from the group consisting of SEQ ID NO: 6 (07F01), SEQ ID NO: 16 (12B11), SEQ ID NO: 26 (17F06), SEQ ID NO: 36 (18H09), SEQ ID NO: 46 (29B06), and SEQ ID NO: 122 (Sh07F01 Hv3-48 D28T T60A L63V E65G); and a CDR$_{H3}$ comprises an amino acid sequence selected from the group consisting of SEQ ID NO:7 (07F01), SEQ ID NO: 17 (12B11), SEQ ID NO: 27 (17F06), SEQ ID NO: 37 (18H09), SEQ ID NO: 47 (29B06), and SEQ ID NO: 123 (Chimeric 07F01 C102S, Sh07F01 Hv3-48, Sh07F01 Hv3-48 D28T T60A L63V E65G). Throughout the specification a particular SEQ ID NO. is followed in parentheses by the antibody that was the origin of that sequence. For example, "SEQ ID NO: 5 (07F01)" means that SEQ ID NO: 5 comes from antibody 07F01.

In some embodiments, the antibody comprises an immunoglobulin heavy chain variable region comprising a CDR$_{H1}$ comprising the amino acid sequence of SEQ ID NO: 5 (07F01), SEQ ID NO: 51 (07F01), or SEQ ID NO: 124 (Sh07F01 Hv3-48 D28T T60A L63V E65G); a CDR$_{H2}$ comprising the amino acid sequence of SEQ ID NO: 6 (07F01) or SEQ ID NO: 122 (Sh07F01 Hv3-48 D28T T60A L63V E65G), and a CDR$_{H3}$ comprising the amino acid sequence of SEQ ID NO: 7 (07F01) or SEQ ID NO: 123 (Chimeric 07F01 C102S, Sh07F01 Hv3-48, Sh07F01 Hv3-48 D28T T60A L63V E65G).

In some embodiments, the heavy chain variable region comprises a CDR$_{H1}$ comprising the amino acid sequence of SEQ ID NO: 5 (07F01), a CDR$_{H2}$ comprising the amino acid sequence of SEQ ID NO: 122 (Sh07F01 Hv3-48 D28T T60A L63V E65G), and a CDR$_{H3}$ comprising the amino acid sequence of SEQ ID NO: 123 (Chimeric 07F01 C102S, Sh07F01 Hv3-48, Sh07F01 Hv3-48 D28T T60A L63V E65G).

In some embodiments, the antibody comprises an immunoglobulin heavy chain variable region comprising a CDR$_{H1}$ comprising the amino acid sequence of SEQ ID NO: 15 (12B11) or SEQ ID NO: 53 (12B11), a CDR$_{H2}$ comprising the amino acid sequence of SEQ ID NO: 16 (12B11), and a CDR$_{H3}$ comprising the amino acid sequence of SEQ ID NO: 17 (12B11).

In some embodiments, the heavy chain variable region comprises a CDR$_{H1}$ comprising the amino acid sequence of SEQ ID NO: 25 (17F06) or SEQ ID NO: 55 (17F06), a CDR$_{H2}$ comprising the amino acid sequence of SEQ ID NO: 26 (17F06), and a CDR$_{H3}$ comprising the amino acid sequence of SEQ ID NO: 27 (17F06).

In some embodiments, the heavy chain variable region comprises a CDR$_{H1}$ comprising the amino acid sequence of SEQ ID NO: 35 (18H09) or SEQ ID NO: 57 (18H09), a CDR$_{H2}$ comprising the amino acid sequence of SEQ ID NO: 36 (18H09), and a CDR$_{H3}$ comprising the amino acid sequence of SEQ ID NO: 37 (18H09).

In some embodiments, the heavy chain variable region comprises a CDR$_{H1}$ comprising the amino acid sequence of SEQ ID NO: 45 (29B06), SEQ ID NO: 59 (29B06), or SEQ ID NO: 126 (Sh29B06 Hv4-59, Hu29B06 Hv4-59 D27G T30S M48I I67V Y78F), a CDR$_{H2}$ comprising the amino acid sequence of SEQ ID NO: 46 (29B06), and a CDR$_{H3}$ comprising the amino acid sequence of SEQ ID NO: 47 (29B06).

In some embodiments, the heavy chain variable region comprises a CDR$_{H1}$ comprising the amino acid sequence of SEQ ID NO: 45 (29B06) or SEQ ID NO: 126 (Sh29B06 Hv4-59, Hu29B06 Hv4-59 D27G T30S M48I I67V Y78F), a CDR$_{H2}$ comprising the amino acid sequence of SEQ ID NO: 46 (29B06), and a CDR$_{H3}$ comprising the amino acid sequence of SEQ ID NO: 47 (29B06).

Preferably, the CDR$_{H1}$, CDR$_{H2}$, and CDR$_{H3}$ sequences are interposed between human or humanized immunoglobulin FRs. The antibody can be an intact antibody or an antigen-binding antibody fragment.

In some embodiments, the antibody comprises (a) an immunoglobulin light chain variable region comprising the structure CDR$_{L1}$-CDR$_{L2}$-CDR$_{L3}$, and (b) an immunoglobulin heavy chain variable region, wherein the IgG light chain variable region and the IgG heavy chain variable region together define a single binding site for binding human RON. A CDR$_{L1}$ comprises an amino acid sequence selected from the group consisting of SEQ ID NO: 8 (07F01), SEQ ID NO: 18 (12B11), SEQ ID NO: 28 (17F06), SEQ ID NO: 38 (18H09), SEQ ID NO: 48 (29B06), and SEQ ID NO: 130 (HE L 07F01 Kv1-9, Sh07F01 Kv1-9 F1); a CDR$_{L2}$ comprises an amino acid sequence selected from the group consisting of SEQ ID NO: 9 (07F01), SEQ ID NO: 19 (12B11), SEQ ID NO: 29 (17F06), SEQ ID NO: 39 (18H09), SEQ ID NO: 49 (29B06), and SEQ ID NO: 131 (HE L 07F01 Kv1-9, Sh07F01 Kv1-9 F1); and a CDR$_{L3}$ comprises an amino acid sequence selected from the group consisting of SEQ ID NO: 10 (07F01), SEQ ID NO: 20 (12B11), SEQ ID NO:30 (17F06), SEQ ID NO: 40 (18H09), and SEQ ID NO: 50 (29B06).

In some embodiments, the antibody comprises an immunoglobulin light chain variable region comprising a CDR$_{L1}$ comprising the amino acid sequence of SEQ ID NO: 8 (07F01) or SEQ ID NO: 130 (HE L 07F01 Kv1-9, Sh07F01 Kv1-9 F1), a CDR$_{L2}$ comprising the amino acid sequence of SEQ ID NO: 9 (07F01) or SEQ ID NO: 131 (HE L 07F01 Kv1-9, Sh07F01 Kv1-9 F1), and a CDR$_{L3}$ comprising the amino acid sequence of SEQ ID NO: 10 (07F01).

In some embodiments, the antibody comprises an immunoglobulin light chain variable region comprising a CDR$_{L1}$ comprising the amino acid sequence of SEQ ID NO: 130 (HE L 07F01 Kv1-9, Sh07F01 Kv1-9 F1); a CDR$_{L2}$ comprising the amino acid sequence of SEQ ID NO: 131 (HE L 07F01 Kv1-9, Sh07F01 Kv1-9 F1); and a CDR$_{L3}$ comprising the amino acid sequence of SEQ ID NO: 10 (07F01).

In some embodiments, the antibody comprises an immunoglobulin light chain variable region comprising a CDR$_{L1}$ comprising the amino acid sequence of SEQ ID NO: 18

(12B11); a CDR$_{L2}$ comprising the amino acid sequence of SEQ ID NO: 19 (12B11); and a CDR$_{L3}$ comprising the amino acid sequence of SEQ ID NO: 20 (12B11).

In some embodiments, the antibody comprises an immunoglobulin light chain variable region comprising a CDR$_{L1}$ comprising the amino acid sequence of SEQ ID NO: 28 (17F06); a CDR$_{L2}$ comprising the amino acid sequence of SEQ ID NO: 29 (17F06); and a CDR$_{L3}$ comprising the amino acid sequence of SEQ ID NO: 30 (17F06).

In some embodiments, the antibody comprises an immunoglobulin light chain variable region comprising a CDR$_{L1}$ comprising the amino acid sequence of SEQ ID NO: 38 (18H09); a CDR$_{L2}$ comprising the amino acid sequence of SEQ ID NO: 39 (18H09); and a CDR$_{L3}$ comprising the amino acid sequence of SEQ ID NO: 40 (18H09).

In some embodiments, the antibody comprises an immunoglobulin light chain variable region comprising a CDR$_{L1}$ comprising the amino acid sequence of SEQ ID NO: 48 (29B06); a CDR$_{L2}$ comprising the amino acid sequence of SEQ ID NO: 49 (29B06); and a CDR$_{L3}$ comprising the amino acid sequence of SEQ ID NO: 50 (29B06).

Preferably, the CDR$_{L1}$, CDR$_{L2}$, and CDR$_{L3}$ sequences are interposed between human or humanized immunoglobulin FRs. The antibody can be an intact antibody or an antigen-binding antibody fragment.

In some embodiments, the antibody comprises: (a) an immunoglobulin heavy chain variable region comprising the structure CDR$_{H1}$-CDR$_{H2}$-CDR$_{H3}$ and (b) an immunoglobulin light chain variable region comprising the structure CDR$_{L1}$-CDR$_{L2}$-CDR$_{L3}$, wherein the heavy chain variable region and the light chain variable region together define a single binding site for binding human RON. The CDR$_{H1}$ is an amino acid sequence selected from the group consisting of SEQ ID NO: 5 (07F01), SEQ ID NO: 51 (07F01), SEQ ID NO: 124 (Sh07F01 Hv3-48 D28T T60A L63V E65G), SEQ ID NO: 15 (12B11), SEQ ID NO: 53 (12B11), SEQ ID NO: 25 (17F06), SEQ ID NO: 55 (17F06), SEQ ID NO: 35 (18H09), SEQ ID NO: 57 (18H09), SEQ ID NO: 45 (29B06), SEQ ID NO: 59 (29B06), and SEQ ID NO: 126 (Sh29B06 Hv4-59, Hu29B06 Hv4-59 D27G T30S M48I I67V Y78F); the CDR$_{H2}$ is an amino acid sequence selected from the group consisting SEQ ID NO: 6 (07F01), SEQ ID NO: 16 (12B11), SEQ ID NO: 26 (17F06), SEQ ID NO: 36 (18H09), SEQ ID NO: 46 (29B06), and SEQ ID NO: 122 (Sh07F01 Hv3-48 D28T T60A L63V E65G); and the CDR$_{H3}$ is an amino acid sequence selected from the group consisting of SEQ ID NO:7 (07F01), SEQ ID NO: 17 (12B11), SEQ ID NO: 27 (17F06), SEQ ID NO: 37 (18H09), SEQ ID NO: 47 (29B06), and SEQ ID NO: 123 (Chimeric 07F01 C102S, Sh07F01 Hv3-48, Sh07F01 Hv3-48 D28T T60A L63V E65G). The CDR$_{L1}$ is an amino acid sequence selected from the group consisting of SEQ ID NO: 8 (07F01), SEQ ID NO: 18 (12B11), SEQ ID NO: 28 (17F06), SEQ ID NO: 38 (18H09), SEQ ID NO: 48 (29B06), and SEQ ID NO: 130 (HE L 07F01 Kv1-9, Sh07F01 Kv1-9 F1); the CDR$_{L2}$ is an amino acid sequence selected from the group consisting of SEQ ID NO: 9 (07F01), SEQ ID NO: 19 (12B11), SEQ ID NO: 29 (17F06), SEQ ID NO: 39 (18H09), SEQ ID NO: 49 (29B06), and SEQ ID NO: 131 (HE L 07F01 Kv1-9, Sh07F01 Kv1-9 F1); and the CDR$_{L3}$ is an amino acid sequence selected from the group consisting of SEQ ID NO: 10 (07F01), SEQ ID NO: 20 (12B11), SEQ ID NO: 30 (17F06), SEQ ID NO: 40 (18H09), and SEQ ID NO: 50 (29B06).

The antibodies disclosed herein comprise an immunoglobulin heavy chain variable region and an immunoglobulin light chain variable region. In some embodiments, the antibody comprises an immunoglobulin heavy chain variable region selected from the group consisting of SEQ ID NO: 2 (07F01), SEQ ID NO: 12 (12B11), SEQ ID NO: 22 (17F06), SEQ ID NO: 32 (18H09), SEQ ID NO: 42 (29B06), SEQ ID NO: 133 (Chimeric 07F01 C102S), SEQ ID NO: 135 (Sh07F01 Hv3-48), SEQ ID NO: 137 (Sh07F01 Hv3-48 D28T T60A L63V E65G), SEQ ID NO: 143 (Sh29B06 Hv4-59), SEQ ID NO: 145 (Hu29B06 Hv4-59), and SEQ ID NO: 147 (Hu29B06 Hv4-59 D27G T30S M48I I67V Y78F), and an immunoglobulin light chain variable region.

In other embodiments, the antibody comprises an immunoglobulin light chain variable region selected from the group consisting of SEQ ID NO: 4 (07F01), SEQ ID NO: 14 (12B11), SEQ ID NO: 24 (17F06), SEQ ID NO: 34 (18H09), SEQ ID NO: 44 (29B06), SEQ ID NO: 139 (HE L 07F01 Kv1-9), SEQ ID NO: 141 (Sh07F01 Kv1-9 F1), and SEQ ID NO: 149 (Sh29B06 Kv2-28), and an immunoglobulin heavy chain variable region.

In some embodiments, the antibody comprises an immunoglobulin heavy chain variable region selected from the group consisting of SEQ ID NO: 2 (07F01), SEQ ID NO: 12 (12B11), SEQ ID NO: 22 (17F06), SEQ ID NO: 32 (18H09), SEQ ID NO: 42 (29B06), SEQ ID NO: 133 (Chimeric 07F01 C102S), SEQ ID NO: 135 (Sh07F01 Hv3-48), SEQ ID NO: 137 (Sh07F01 Hv3-48 D28T T60A L63V E65G), SEQ ID NO: 143 (Sh29B06 Hv4-59), SEQ ID NO: 145 (Hu29B06 Hv4-59), and SEQ ID NO: 147 (Hu29B06 Hv4-59 D27G T30S M48I I67V Y78F), and an immunoglobulin light chain variable region selected from the group consisting of SEQ ID NO: 4 (07F01), SEQ ID NO: 14 (12B11), SEQ ID NO: 24 (17F06), SEQ ID NO: 34 (18H09), SEQ ID NO: 44 (29B06), SEQ ID NO: 139 (HE L 07F01 Kv1-9), SEQ ID NO: 141 (Sh07F01 Kv1-9 F1), and SEQ ID NO: 149 (Sh29B06 Kv2-28).

In some embodiments, the antibody comprises an immunoglobulin heavy chain variable region comprising the amino acid sequence of SEQ ID NO: 2 (07F01), and an immunoglobulin light chain variable region comprising the amino acid sequence of SEQ ID NO: 4 (07F01).

In some embodiments, the antibody comprises an immunoglobulin heavy chain variable region comprising the amino acid sequence of SEQ ID NO: 12 (12B11), and an immunoglobulin light chain variable region comprising the amino acid sequence of SEQ ID NO: 14 (12B11).

In some embodiments, the antibody comprises an immunoglobulin heavy chain variable region comprising the amino acid sequence of SEQ ID NO: 22 (17F06), and an immunoglobulin light chain variable region comprising the amino acid sequence of SEQ ID NO: 24 (17F06).

In some embodiments, the antibody comprises an immunoglobulin heavy chain variable region comprising the amino acid sequence of SEQ ID NO: 32 (18H09), and an immunoglobulin light chain variable region comprising the amino acid sequence of SEQ ID NO: 34 (18H09).

In some embodiments, the antibody comprises an immunoglobulin heavy chain variable region comprising the amino acid sequence of SEQ ID NO: 42 (29B06), and an immunoglobulin light chain variable region comprising the amino acid sequence of SEQ ID NO: 44 (29B06).

In some embodiments, the antibody comprises an immunoglobulin heavy chain variable region comprising the amino acid sequence of SEQ ID NO: 137 (Sh07F01 Hv3-48 D28T T60A L63V E65G), and an immunoglobulin light chain variable region comprising the amino acid sequence of SEQ ID NO: 139 (HE L 07F01 Kv1-9).

In some embodiments, the antibody comprises an immunoglobulin heavy chain variable region comprising the amino acid sequence of SEQ ID NO: 147 (Hu29B06 Hv4-59 D27G T30S M48I I67V Y78F), and an immunoglobulin light chain variable region comprising the amino acid sequence of SEQ ID NO: 149 (Sh29B06 Kv2-28).

In certain embodiments, the antibodies disclosed herein comprise an immunoglobulin heavy chain and an immunoglobulin light chain. In some embodiments, the antibody comprises an immunoglobulin heavy chain selected from the group consisting of SEQ ID NO: 93 (07F01), SEQ ID NO: 97 (12B11), SEQ ID NO: 101 (17F06), SEQ ID NO: 105 (18H09), SEQ ID NO: 109 (29B06), SEQ ID NO: 156 (Chimeric 07F01 C102S IgG1), SEQ ID NO: 160 (Chimeric 29B06 IgG1), SEQ ID NO: 164 (Sh07F01 Hv3-48 IgG1), SEQ ID NO: 166 (Sh07F01 Hv3-48 D28T T60A L63V E65G IgG1), SEQ ID NO: 172 (Sh29B06 Hv4-59 IgG1), SEQ ID NO: 174 (Hu29B06 Hv4-59 IgG1), and SEQ ID NO: 176 (Hu29B06 Hv4-59 D27G T30S M48I I67V Y78F IgG1), and an immunoglobulin light chain.

In other embodiments, the antibody comprises an immunoglobulin light chain selected from the group consisting of SEQ ID NO: 95 (07F01), SEQ ID NO: 99 (12B11), SEQ ID NO: 103 (17F06), SEQ ID NO: 107 (18H09), SEQ ID NO: 111 (29B06), SEQ ID NO: 158 (Chimeric 07F01 Kappa), SEQ ID NO: 162 (Chimeric 29B06 Kappa), SEQ ID NO: 168 (HE L 07F01 Kv1-9 Kappa), SEQ ID NO: 170 (Sh07F01 Kv1-9 F1 Kappa), and SEQ ID NO: 178 (Sh29B06 Kv2-28 Kappa), and an immunoglobulin heavy chain.

In some embodiments, the antibody comprises (i) an immunoglobulin heavy chain selected from the group consisting of SEQ ID NO: 93 (07F01), SEQ ID NO: 97 (12B11), SEQ ID NO: 101 (17F06), SEQ ID NO: 105 (18H09), SEQ ID NO: 109 (29B06), SEQ ID NO: 156 (Chimeric 07F01 C102S IgG1), SEQ ID NO: 160 (Chimeric 29B06 IgG1), SEQ ID NO: 164 (Sh07F01 Hv3-48 IgG1), SEQ ID NO: 166 (Sh07F01 Hv3-48 D28T T60A L63V E65G IgG1), SEQ ID NO: 172 (Sh29B06 Hv4-59 IgG1), SEQ ID NO: 174 (Hu29B06 Hv4-59 IgG1), and SEQ ID NO: 176 (Hu29B06 Hv4-59 D27G T30S M48I I67V Y78F IgG1), and (ii) an immunoglobulin light chain selected from the group consisting of SEQ ID NO: 95 (07F01), SEQ ID NO: 99 (12B11), SEQ ID NO: 103 (17F06), SEQ ID NO: 107 (18H09), SEQ ID NO: 111 (29B06), SEQ ID NO: 158 (Chimeric 07F01 Kappa), SEQ ID NO: 162 (Chimeric 29B06 Kappa), SEQ ID NO: 168 (HE L 07F01 Kv1-9 Kappa), SEQ ID NO: 170 (Sh07F01 Kv1-9 F1 Kappa), and SEQ ID NO: 178 (Sh29B06 Kv2-28 Kappa).

In some embodiments, the antibody comprises an immunoglobulin heavy chain comprising the amino acid sequence of SEQ ID NO: 93 (07F01), and an immunoglobulin light chain comprising the amino acid sequence of SEQ ID NO: 95 (07F01).

In some embodiments, the antibody comprises an immunoglobulin heavy chain comprising the amino acid sequence of SEQ ID NO: 97 (12B11), and an immunoglobulin light chain comprising the amino acid sequence of SEQ ID NO: 99 (12B11).

In some embodiments, the antibody comprises an immunoglobulin heavy chain comprising the amino acid sequence of SEQ ID NO: 101 (17F06), and an immunoglobulin light chain comprising the amino acid sequence of SEQ ID NO: 103 (17F06).

In some embodiments, the antibody comprises an immunoglobulin heavy chain comprising the amino acid sequence of SEQ ID NO: 105 (18H09), and an immunoglobulin light chain comprising the amino acid sequence of SEQ ID NO: 107 (18H09).

In some embodiments, the antibody comprises an immunoglobulin heavy chain comprising the amino acid sequence of SEQ ID NO: 109 (29B06), and an immunoglobulin light chain comprising the amino acid sequence of SEQ ID NO: 111 (29B06).

In some embodiments, the antibody comprises an immunoglobulin heavy chain comprising the amino acid sequence of SEQ ID NO: 166 (Sh07F01 Hv3-48 D28T T60A L63V E65G IgG1), and an immunoglobulin light chain comprising the amino acid sequence of SEQ ID NO: 168 (HE L 07F01 Kv1-9 Kappa).

In some embodiments, the antibody comprises an immunoglobulin heavy chain comprising the amino acid sequence of SEQ ID NO: 176 (Hu29B06 Hv4-59 D27G T30S M48I I67V Y78F IgG1), and an immunoglobulin light chain comprising the amino acid sequence of SEQ ID NO: 178 (Sh29B06 Kv2-28 Kappa).

In certain embodiments, an isolated antibody that binds human RON comprises an immunoglobulin heavy chain variable region comprising an amino acid sequence that is at least 70%, 75%, 80%, 85%, 90%, 95%, 98%, or 99% identical to the entire variable region or the framework region sequence of SEQ ID NO: 2 (07F01), SEQ ID NO: 12 (12B11), SEQ ID NO: 22 (17F06), SEQ ID NO: 32 (18H09), SEQ ID NO: 42 (29B06), SEQ ID NO: 133 (Chimeric 07F01 C102S), SEQ ID NO: 135 (Sh07F01 Hv3-48), SEQ ID NO: 137 (Sh07F01 Hv3-48 D28T T60A L63V E65G), SEQ ID NO: 143 (Sh29B06 Hv4-59), SEQ ID NO: 145 (Hu29B06 Hv4-59), or SEQ ID NO: 147 (Hu29B06 Hv4-59 D27G T30S M48I I67V Y78F).

In certain embodiments, an isolated antibody that binds human RON comprises an immunoglobulin light chain variable region comprising an amino acid sequence that is at least 70%, 75%, 80%, 85%, 90%, 95%, 98%, or 99% identical to the entire variable region or the framework region sequence of SEQ ID NO: 4 (07F01), SEQ ID NO: 14 (12B11), SEQ ID NO: 24 (17F06), SEQ ID NO: 34 (18H09), SEQ ID NO: 44 (29B06), SEQ ID NO: 139 (HE L 07F01 Kv1-9), SEQ ID NO: 141 (Sh07F01 Kv1-9 F1), or SEQ ID NO: 149 (Sh29B06 Kv2-28).

Homology or identity may be determined in various ways that are within the skill in the art, for instance, using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) PROC. NATL. ACAD. SCI. USA 87, 2264-2268; Altschul, (1993) J. MOL. EVOL. 36, 290-300; Altschul et al., (1997) NUCLEIC ACIDS RES. 25, 3389-3402, incorporated by reference) are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases see Altschul et al., (1994) NATURE GENETICS 6, 119-129 which is fully incorporated by reference. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) PROC. NATL. ACAD. SCI. USA 89, 10915-10919, fully incorporated by reference). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: -G, Cost to open gap [Integer]: default=5 for nucleotides/11 for proteins; -E, Cost to extend gap [Integer]: default=2 for nucleotides/1 for proteins; -q, Penalty for nucleotide mismatch [Integer]: default=−3; -r, reward for nucleotide match [Integer]: default=1; -e, expect value [Real]: default=10; -W, wordsize [Integer]: default=11 for nucleotides/28 for megablast/3 for proteins; -y, Dropoff (X) for blast extensions in bits: default=20 for blastn/7 for others; -X, X dropoff value for gapped alignment (in bits): default=15 for all programs, not applicable to blastn; and -Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

In each of the foregoing embodiments, it is contemplated herein that immunoglobulin heavy chain variable region sequences and/or light chain variable region sequences that together bind human RON may contain amino acid alterations (e.g., at least 1, 2, 3, 4, 5, or 10 amino acid substitutions, deletions, or additions) in the framework regions of the heavy and/or light chain variable regions.

In certain embodiments, the antibody binds human RON with a $K_D$ of 1 nM, 900 pM, 750 pM, 650 pM, 600 pM, 500 pM, 400 pM, 300 pM, 250 pM, 200 pM, 150 pM, 100 pM, 50 pM or lower. Unless otherwise specified, $K_D$ values are determined by surface plasmon resonance methods under the conditions described in Examples 5 and 14.

Antibody Sh29B06-78 binds human RON with a $K_D$ of 500 pM, 250 pM, 200 pM, 150 pM, 100 pM or lower as measured by surface plasmon resonance methods under the conditions described in Examples 5 and 14. In an exemplary embodiment, antibody Sh29B06-78 binds human RON with a $K_D$ of 150 pM or lower as measured by surface plasmon resonance methods at 37° C. under the conditions described in Examples 5 and 14.

Antibody SH07F01-62 binds human RON with a $K_D$ of 500 pM, 400 pM, 350 pM, 300 pM, 250 pM, 200 pM, 150 pM, 100 pM or lower as measured by surface plasmon resonance methods under the conditions described in Examples 5 and 14. In an exemplary embodiment, antibody SH07F01-62 binds human RON with a $K_D$ of 250 pM to 350 pM or lower as measured by surface plasmon resonance methods at 37° C. under the conditions described in Examples 5 and 14.

In certain embodiments, the antibodies inhibit human MSP binding to human RON. For example, the antibodies can have an $IC_{50}$ (concentration at 50% of maximum inhibition) of about 5 nM, 2 nM, 1 nM or lower, when assayed using the protocol described in Examples 8 and 15.

Although the embodiments illustrated in the Examples comprise pairs of variable regions, pairs of full length antibody chains, or pairs of CDR1, CDR2 and CDR3 regions, one from a heavy chain and one from a light chain, a skilled artisan will recognize that alternative embodiments may comprise single heavy chain variable regions or single light chain variable regions, single full length antibody chains, or CDR1, CDR2 and CDR3 regions from one antibody chain, either heavy or light. The single variable region, full length antibody chain or CDR1, CDR2 and CDR3 region of one chain can be used to screen for corresponding domains in another chain, the two chains capable of forming an antibody that binds antigen. The screening may be accomplished by phage display screening methods using, e.g., a hierarchical dual combinatorial approach disclosed in PCT Publ. No. WO92/01047. In this approach, an individual colony containing either a heavy or light chain clone is used to infect a complete library of clones encoding the other chain (light or heavy), and the resulting two-chain specific antigen-binding domain is selected in accordance with phage display techniques as described.

II. Production of Antibodies

Methods for producing antibodies, such as those disclosed herein, are known in the art. For example, DNA molecules encoding light chain variable regions and/or heavy chain variable regions can be chemically synthesized using the sequence information provided herein. Synthetic DNA molecules can be ligated to other appropriate nucleotide sequences, including, e.g., constant region coding sequences, and expression control sequences, to produce conventional gene expression constructs encoding the desired antibodies. Production of defined gene constructs is within routine skill in the art. Alternatively, the sequences provided herein can be cloned out of hybridomas by conventional hybridization techniques or polymerase chain reaction (PCR) techniques, using synthetic nucleic acid probes whose sequences are based on sequence information provided herein, or prior art sequence information regarding genes encoding the heavy and light chains of murine antibodies in hybridoma cells.

Nucleic acids encoding desired antibodies can be incorporated (ligated) into expression vectors, which can be introduced into host cells through conventional transfection or transformation techniques. Exemplary host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the immunoglobulin light and/or heavy chain variable regions.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

If the engineered gene is to be expressed in eukayotic host cells, e.g., CHO cells, it is first inserted into an expression vector containing a suitable eukaryotic promoter, a secretion signal, IgG enhancers, and various introns. This expression vector optionally contains sequences encoding all or part of a constant region, enabling an entire, or a part of, a heavy or light chain to be expressed. The gene construct can be introduced into eukaryotic host cells using conventional techniques. The host cells express $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof, each of which may be attached to a moiety having another function (e.g., cytotoxicity). In some embodiments, a host cell is transfected with a single vector expressing a polypeptide expressing an entire, or part of, a heavy chain (e.g., a heavy chain variable region) or a light chain (e.g., a light chain variable region). In other embodiments, a host cell is transfected with a single vector encoding (a) a polypeptide comprising a heavy chain variable region and a polypeptide comprising a light chain variable region, or (b) an entire immunoglobulin heavy chain and an entire immunoglobulin light chain. In still other embodiments, a host cell is co-transfected with more than one expression vector (e.g., one expression vector expressing a polypeptide comprising an entire, or part of, a heavy chain or heavy chain variable region, and another expression vector expressing a polypeptide comprising an entire, or part of, a light chain or light chain variable region).

A polypeptide comprising an immunoglobulin heavy chain variable region or light chain variable region can be produced by growing a host cell transfected with an expression vector encoding such variable region, under conditions that permit expression of the polypeptide. Following expression, the polypeptide can be harvested and purified using techniques well known in the art, e.g., affinity tags such as glutathione-S-transferase (GST) and histidine tags.

A monoclonal antibody that binds human RON, or an antigen-binding fragment of the antibody, can be produced by growing a host cell transfected with: (a) an expression vector that encodes a complete or partial immunoglobulin heavy chain, and a separate expression vector that encodes a complete or partial immunoglobulin light chain; or (b) a single expression vector that encodes both chains (e.g., complete or partial heavy and light chains), under conditions that permit expression of both chains. The intact antibody (or antigen-binding fragment) can be harvested and purified using techniques well known in the art, e.g., Protein A, Protein G, affinity tags such as glutathione-S-transferase (GST) and histidine tags. It is within ordinary skill in the art to express the heavy chain and the light chain from a single expression vector or from two separate expression vectors.

III. Antibody Modifications

Methods for reducing or eliminating the antigenicity of antibodies and antibody fragments are known in the art. When the antibodies are to be administered to a human, the antibodies preferably are "humanized" to reduce or eliminate antigenicity in humans. Preferably, the humanized antibodies have the same or substantially the same affinity for the antigen as the non-humanized mouse antibody from which it was derived.

In one humanization approach, chimeric proteins are created in which mouse immunoglobulin constant regions are replaced with human immunoglobulin constant regions. See, e.g., Morrison et al., 1984, PROC. NAT. ACAD. SCI. 81:6851-6855, Neuberger et al., 1984, NATURE 312:604-608; U.S. Pat. No. 6,893,625 (Robinson); U.S. Pat. No. 5,500,362 (Robinson); and U.S. Pat. No. 4,816,567 (Cabilly).

In an approach known as CDR grafting, the CDRs of the light and heavy chain variable regions are grafted into frameworks from another species. For example, murine CDRs can be grafted into human FRs. In some embodiments, the CDRs of the light and heavy chain variable regions of an anti-RON antibody are grafted into human FRs or consensus human FRs. To create consensus human FRs, FRs from several human heavy chain or light chain amino acid sequences are aligned to identify a consensus amino acid sequence. CDR grafting is described in U.S. Pat. No. 7,022,500 (Queen); U.S. Pat. No. 6,982,321 (Winter); U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); Jones et al. (1986) NATURE 321: 522-525; Riechmann et al. (1988) NATURE 332: 323-327; Verhoeyen et al. (1988) SCIENCE 239: 1534-1536; and Winter (1998) FEBS LETT 430: 92-94.

In an approach called "SUPERHUMANIZATION™," human CDR sequences are chosen from human germline genes, based on the structural similarity of the human CDRs to those of the mouse antibody to be humanized. See, e.g., U.S. Pat. No. 6,881,557 (Foote); and Tan et al., 2002, J. IMMUNOL. 169:1119-1125.

Other methods to reduce immunogenicity include "reshaping," "hyperchimerization," and "veneering/resurfacing." See, e.g., Vaswami et al., 1998, ANNALS OF ALLERGY, ASTHMA, & IMMUNOL. 81:105; Roguska et al., 1996, PROT. ENGINEER 9:895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, e.g., in U.S. Pat. No. 5,639,641 (Pedersen).

Another approach for converting a mouse antibody into a form suitable for medical use in humans is known as ACTIVMAB™ technology (Vaccinex, Inc., Rochester, N.Y.), which involves a vaccinia virus-based vector to express antibodies in mammalian cells. High levels of combinatorial diversity of IgG heavy and light chains are said to be produced. See, e.g., U.S. Pat. No. 6,706,477 (Zauderer); U.S. Pat. No. 6,800,442 (Zauderer); and U.S. Pat. No. 6,872,518 (Zauderer).

Another approach for converting a mouse antibody into a form suitable for use in humans is technology practiced commercially by KaloBios Pharmaceuticals, Inc. (Palo Alto, Calif.). This technology involves the use of a proprietary human "acceptor" library to produce an "epitope focused" library for antibody selection.

Another approach for modifying a mouse antibody into a form suitable for medical use in humans is HUMAN ENGINEERING™ technology, which is practiced commercially by XOMA (US) LLC. See, e.g., PCT Publication No. WO 93/11794 and U.S. Pat. No. 5,766,886 (Studnicka); U.S. Pat. No. 5,770,196 (Studnicka); U.S. Pat. No. 5,821,123 (Studnicka); and U.S. Pat. No. 5,869,619 (Studnicka).

Any suitable approach, including any of the above approaches, can be used to reduce or eliminate human immunogenicity of an antibody.

In addition, it is possible to create fully human antibodies in mice. Fully human mAbs lacking any non-human sequences can be prepared from human immunoglobulin transgenic mice by techniques referenced in, e.g., Lonberg et al., NATURE 368:856-859, 1994; Fishwild et al., NATURE BIOTECHNOLOGY 14:845-851, 1996; and Mendez et al., NATURE GENETICS 15:146-156, 1997. Human mAbs can also be prepared and optimized from phage display libraries by techniques referenced in, e.g., Knappik et al., J. MOL. BIOL. 296: 57-86, 2000; and Krebs et al., J. Immunol. Meth. 254:67-84 2001).

If the antibody is for use as a therapeutic, it can be conjugated to an effector agent such as a small molecule toxin or a radionuclide using standard in vitro conjugation chemistries. If the effector agent is a polypeptide, the antibody can be chemically conjugated to the effector or joined to the effector as a fusion protein. Construction of fusion proteins is within ordinary skill in the art.

IV. Use of Antibodies

The antibodies disclosed herein can be used to treat various forms of cancer, e.g., non-small cell lung cancer, breast, ovarian, prostate, cervical, colorectal, lung, pancreatic, gastric, and head and neck cancers. The cancer cells are exposed to a therapeutically effective amount of the antibody so as to inhibit or reduce proliferation of the cancer cell. In some embodiments, the antibodies inhibit cancer cell proliferation by at least 40%, 50%, 60%, 70%, 80%, 90%, 95%, 98%, 99%, or 100%.

In some embodiments, the antibody (e.g., 07F01, 29B06, 17F06, 18H09, 12B11, sh29B06, sh07F01) inhibits or reduces proliferation of a tumor cell by inhibiting binding of human RON to its ligand, MSP. In some embodiments, the antibody (e.g., 07F01, 29B06, 17F06, 18H09, 12B11, sh29B06, sh07F01) inhibits or reduces proliferation of a tumor cell without inhibiting RON binding to MSP. The antibody (e.g., 07F01, 29B06, 17F06, 18H09, 12B11, sh29B06, sh07F01) can also be used in therapy. The antibody (e.g., 07F01, 29B06, 17F06, 18H09, 12B11, sh29B06, sh07F01) can be used to inhibit tumor growth in a mammal (e.g., a human patient). In some embodiments, use of the antibody to inhibit tumor growth in a mammal comprises administering to the mammal a therapeutically effective amount of the antibody.

In certain embodiments, antibody Sh29B06-78 is used in therapy. For example, antibody Sh29B06-78 can be used for inhibiting or reducing proliferation of a tumor cell. Antibody Sh29B06-78 can also be used for inhibiting or reducing tumor growth in a mammal.

In other embodiments, antibody Sh07F01-62 is used in therapy. For example, antibody Sh07F01-62 can be used for inhibiting or reducing proliferation of a tumor cell. Antibody Sh07F01-62 can also be used for inhibiting or reducing tumor growth in a mammal.

Cancers associated with overexpression or inappropriate activation of RON include non-small cell lung cancer, breast cancer, ovarian cancer, prostate cancer, lung cancer, colorectal cancer, pancreatic cancer, bladder cancer, and some forms of brain cancer, melanomas, and gastrointestinal cancers.

As used herein, "treat," "treating" and "treatment" mean the treatment of a disease in a mammal, e.g., in a human. This includes: (a) inhibiting the disease, i.e., arresting its development; and (b) relieving the disease, i.e., causing regression of the disease state.

Generally, a therapeutically effective amount of active component is in the range of 0.1 mg/kg to 100 mg/kg, e.g., 1 mg/kg to 100 mg/kg, 1 mg/kg to 10 mg/kg. The amount administered will depend on variables such as the type and extent of disease or indication to be treated, the overall health of the patient, the in vivo potency of the antibody, the pharmaceutical formulation, and the route of administration. The initial dosage can be increased beyond the upper level in order to rapidly achieve the desired blood-level or tissue level. Alternatively, the initial dosage can be smaller than the optimum, and the dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount and the disease being treated. Exemplary dosing frequencies are once per day, once per week and once every two weeks. In some embodiments, dosing is once every two weeks. A preferred route of administration is parenteral, e.g., intravenous infusion. Formulation of monoclonal antibody-based drugs is within ordinary skill in the art. In some embodiments, the antibody is lyophilized and reconstituted in buffered saline at the time of administration.

For therapeutic use, an antibody preferably is combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing antibodies, such as those disclosed herein, can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, and rectal administration. A preferred route of administration for monoclonal antibodies is IV infusion. Useful formulations can be prepared by methods well known in the pharmaceutical art. For example, see *Remington's Pharmaceutical Sciences*, 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

EXAMPLES

The following Examples are merely illustrative and are not intended to limit the scope or content of the invention in any way.

Example 1

Production of Human RON Extracellular Domain (ECD)

This Example describes the production of the antigen, hRON ECD protein. The use of the full length ECD as the immunogen, allowed for the selection of two classes of hybridomas: (a) those producing antibodies that interact with the ligand binding domain, thereby inhibiting contact of the ligand to the receptor; and (b) those producing antibodies that bind outside the ligand binding domain, thereby inhibiting the receptor functions through mechanisms other than inhibition of ligand binding.

DNA encoding the extracellular domain of human RON (hRON ECD) (ref seq. NM_002447) was amplified by PCR and subcloned using the XmaI/EcoRI restriction sites in-frame into the pEE14.4 vector (Lonza, Basel, Switzerland) containing THXmFC (Thrombin/His tag/Factor Xa-AJ mouse IgG-Fc), to produce a fusion protein. The resulting clone was linearized using the PvuI enzyme (NEBiolabs, Cat. No. R0150), then electroporated into CHO K1SVcells (Lonza). The electroporated cells were diluted in 200 ml CD CHO media (Gibco Cat. No. 10743-011). The next day, CD CHO media containing methionine sulfoximine (MSX) for a final concentration of 50 µM was added to the cells. After four weeks, positive clones were selected by sandwich ELISA in which the immobilized antibody was commercial monoclonal anti-hRON antibody MAB691 (R&D Systems), and the detection antibody was commercial polyclonal anti-hRON antibody AF691 (R&D Systems). Positive clones were re-transfected using LIPOFECTAMINE™ 2000 in a standard protocol. Cells were aliquoted into four separate shaker flasks and selected using 50 uM, 100 uM, 200 uM, and 400 uM MSX. After two weeks of selection, the individual flasks were checked for hRON-ECD protein expression by ELISA. The highest selection pressure, 400 µM MSX, yielded good protein expression and was chosen for scale-up and purification. Cells were grown for 2 weeks at 37° C. in BELLOCELL® Bottles (Bellco Glass, Vineland, N.J.) at a concentration of 2-2.5×10$^6$ cells/ml in CD CHO media, with a final concentration of 80 µM MSX for protein production. The resulting cells were spun down in 500 ml conical tubes for 15 minutes. The supernatant was filtered using vacuum filtration using a 0.45 micron filter and then a 0.22 micron filter. The protein was then batch bound to PROSEP®-A beads (Millipore) at 4° C. overnight with rotation after adjusting the pH to 7.5. The beads were washed with 1×PBS and loaded onto disposable protein A affinity columns (Bio-Rad ECONO-PAC® columns; Bio-Rad cat. No. 732-1010). The beads were washed with 10 column volumes (CV) of glycine binding buffer (3M glycine ph 9.0, 1M NaCl). The protein was then eluted off the column using 5-10 CV of 200 mM glycine pH 2.5 acid elution buffer. The samples were then neutralized using 1.3 mL of 1.0 M Tris pH 8.0 neutralization buffer concentrated using VIVASPIN® concentrators (Sartorius Stedim Biotech).

Example 2

Anti-RON Antibodies

This Example describes the production of anti-hRON monoclonal antibodies. Immunizations, fusions, and primary screens were conducted at Maine Biotechnology Services Inc. (Portland, Me.), following the Repetitive Immunization Multiple Sites (RIMMS) protocol. Five AJ mice and five Balb/c mice were immunized with recombinant human RON extracellular domain (hRON-ECD). Two Balb/c mice with sera displaying the highest anti-RON activity by Enzyme Linked Immunosorbent Assay (ELISA) were chosen for subsequent fusion. Spleens and lymph nodes from the appropriate mice were harvested. B-cells were harvested and fused with a myeloma line. Fusion products were serially diluted onto forty 96-well plates to near clonality.

Approximately 4,000 supernatants from the cell fusions were screened by ELISA for binding to recombinant hRON-ECD. A total of 158 supernatants containing antibodies against RON were further characterized by in vitro biochemical and cell-based assays, as described below. A panel of hybridomas was selected, subcloned and expanded. Hybridoma cell lines were transferred to BioXCell (West Lebanon, N.H.) for antibody expression and purification by affinity chromatography on Protein G resin, under standard conditions.

Example 3

Screening Assays

A biochemical assay was carried out to identify antibodies that inhibit ligand binding. A cell-based assay was carried out to identify antibodies that inhibit MSP induced phosphoERK downstream signaling of the receptor. Antibodies that inhibited RON mediated cellular signaling were selected for further characterization regardless of whether they blocked ligand binding in the neutralization assay.

The biochemical neutralization assay measures inhibition of MSP binding to hRON by antibodies in hybridoma supernatants, using electrochemiluminescence (ECL). MA2400 96-well high binding plates (Meso Scale Discovery) were coated with 25 µl of 0.42 µg/mL hRON SEMA+PSI (an N-terminal portion of the ECD of hRON; R&D Systems) in PBS for one hour at room temperature with agitation. The plates were washed four times with PBS+0.1% TWEEN-20™ (PBST), and blocked with 150 µl of charcoal-stripped fetal bovine serum (FBS) (Gibco). The hybridoma supernatant were added and incubated for 45 minutes at room temperature. After incubation, 5 µl of MSP (3 µg/mL) in charcoal stripped FBS was added to each well, and incubated for 45 minutes. The plate was washed four times with PBST, and 25 µl of 1 µg/mL biotinylated anti-MSP antibody (R&D Systems) was added to the plates for one hour at room temperature with agitation. The plates were washed four times with PBST, and incubated with 25 µl of 1 µg/mL ST-streptavidin (Meso Scale Discovery) for one hour at room temperature with agitation. The plates were washed four times with PBST, and 150 µl read buffer (Meso Scale Discovery) was added to each well before the plates were analyzed on a SECTOR® IMAGER 2400 (Meso Scale Discovery) instrument. Antibodies 07F01, 18H09 and 29B06 each blocked MSP binding to hRON SEMA+PSI in this neutralization assay.

In the cell-based assay, antibodies in the hybridoma supernatant were tested for inhibition of MSP-induced phosphorylation of ERK, which is a RON downstream signaling molecule. T47D cells were cultured in 96-well plates in RPMI 1640+10% FBS+insulin. Medium was removed, and cells were incubated in serum-free medium for 24 hours. Hybridoma supernatants containing RON antibodies were added to the cells at a dilution of 1:4 in-serum-free medium, and incubated for one hour at 37° C. MSP (5 nM) was added to the wells and incubated for 15 minutes. Medium was removed, and cells were fixed in 4% paraformaldehyde (PFA) in PBS. Total ERK and phospho-ERK were measured according to the vendor's instructions (R&D Systems, DY1018). Antibodies 07F01, 12B11, 17F06, 18H09 and 29B06 each inhibited MSP induced ERK phosphorylation in T47D cells.

As discussed herein (see Examples 8 and 9), antibodies 07F01, 12B11, 17F06, 18H09 and 29B06 each inhibited MSP induced ERK phosphorylation in T47D cells, while only antibodies 07F01, 18H09 and 29B06 each blocked MSP binding to hRON SEMA+PSI in the neutralization assay. This suggests that antibodies 12B11 and 17F06 do not neutralize binding of MSP to the hRON SEMA+PSI domain, neutralize binding of MSP to RON in the context of the full RON extracellular domain, or function by a mechanism other than blocking MSP binding to RON.

Example 4

Antibody Sequence Analysis

The light chain isotype and heavy chain isotype of each monoclonal antibody in Example 2 was determined using the ISOSTRIP™ Mouse Monoclonal Antibody Isotyping Kit according the kit vendor's instructions (Roche Applied Science, Indianapolis, Ind.). All antibodies were found to be kappa or lambda light chain and IgG1 or IgG2a heavy chain.

The heavy and light chain variable regions of the mouse monoclonal antibodies were sequenced using 5' RACE (Rapid Amplification of cDNA Ends). Total RNA was extracted from each monoclonal hybridoma cell line using the RNEASY® Miniprep kit according to the kit vendor's instructions (Qiagen, Valencia, Calif.). Full-length first strand cDNA containing 5' ends was generated using either the GENERACER™ Kit (Invitrogen, Carlsbad, Calif.) or SMARTER™ RACE cDNA Amplification Kit (Clontech, Mountain View, Calif.) according to the kit vendor's instructions using random primers for 5' RACE.

The variable regions of the light (kappa or lambda) and heavy (IgG1 or IgG2b) chains were amplified by PCR, using KOD Hot Start Polymerase (EMD Chemicals, Gibbstown, N.J.), Expand High Fidelity PCR System (Roche Applied Science), or Advantage 2 Polymerase Mix (Clontech) according to the kit vendor's instructions. For amplification of 5' cDNA ends in conjunction with the GENERACER™ Kit, the GENERACER™ 5' Primer, 5' cgactggagcacgaggacactga 3' (SEQ ID NO: 112) (Invitrogen) was used as a 5' primer. For amplification of 5' cDNA ends in conjunction with the SMARTER™ RACE cDNA Amplification Kit, the Universal Primer Mix A primer (Clontech), a mix of: 5' CTAATACGACTCAC-TATAGGGCAAGCAGTGGTATCAACGCAGAGT 3' (SEQ ID NO: 113) and 5' CTAATACGACTCACTATAGGGC 3' (SEQ ID NO: 114), was used as a 5' primer. Heavy chain variable regions were amplified using the above 5' primers and a 3' IgG1 constant region specific primer, 5' TATGCAAGGCTTACAACCACA 3' (SEQ ID NO: 115), or a 3' IgG2a constant region specific primer, 5' AGGA-CAGGGCTTGATTGTGGG 3' (SEQ ID NO: 116). Kappa chain variable regions were amplified with the above 5' primers and a 3' kappa constant region specific primer, 5' CTCATTCCTGT-TGAAGCTCTTGACAAT 3' (SEQ ID NO: 117). Lambda chain variable regions were amplified with the above 5' primers and a mix of 3' lambda constant region specific primers, 5' GCACGG-GACAAACTCTTCTC 3' (SEQ ID NO: 118) and 5' CACAGTGTCCCCT-TCATGTG 3' (SEQ ID NO: 119).

Individual PCR products were isolated by agarose gel electrophoresis and purified using the QIAQUICK® Gel Purification kit according to the kit vendor's instructions (Qiagen). The PCR products were subsequently cloned into the PCR® 4Blunt TOPO® plasmid or PCR2.1® TOPO plasmid using the ZERO BLUNT® TOPO® PCR Cloning Kit or the TOPO® TA Cloning Kit, respectively, according to the kit vendor's instructions (Invitrogen) and transformed into DH5-α bacteria (Invitrogen) through standard molecular biology techniques. Plasmid DNA isolated from transformed bacterial clones was sequenced using M13 Forward (5' GTAAAACGACGGCCAGT 3') (SEQ ID NO: 120) and M13 Reverse primers (5' CAGGAAACAGCTATGACC 3') (SEQ ID NO: 121) by Beckman Genomics (Danvers, Mass.), using standard dideoxy DNA sequencing methods to identify the sequence of the variable region sequences. The sequences were analyzed using VECTOR NTI® software (Invitrogen) and the IMGT/V-Quest web server (imgt.cines.fr) to identify and confirm variable region sequences.

The nucleic acid sequences encoding and the protein sequences defining variable regions of the murine monoclonal antibodies are shown below (amino terminal signal peptide sequences are not shown). CDR sequences (Kabat definition) are indicated by bold font and underlining in the amino acid sequences.

```
Nucleic Acid Sequence Encoding the Heavy Chain Variable Region of the
07F01 Antibody
                                                          (SEQ ID NO: 1)
  1  gaggtgaagc ttctcgagtc tggaggtggc ctggtgcagc cgggtggatc cctgaaactc 61  tcctgtgcag cctcaggatt cgatttagt agacactgga tgagttgggt ccggctggct 121  ccagggaaag ggctagaatg gatcgcagaa attaatccag atagcagaac gataaactat 181  acgccatctc taaaggagaa attcatcatc tccagagaca cgccaaaaa ttcgctgttt 241  ctgcaaatga acagagtgag atctgaggac acagcccttt attactgtgc aagacgggta 301  agaattcatt actacggcgc tatggactgc tggggtcaag aacctcagt caccgtctcc 361  tca Protein Sequence Defining the Heavy Chain Variable Region of the
07F01 Antibody
                                                          (SEQ ID NO: 2)
  1  evkllesggg lvqpggslkl scaasgfdfs rhwmswvrla pgkglewiae inpdsrtiny

61  tpslkekfii srdnaknslf lqmnrvrsed talyycarrv rihyygamdc wgqgtsvtvs 121  s Nucleic Acid Sequence Encoding the Kappa Chain Variable Region of the
07F01 Antibody
                                                          (SEQ ID NO: 3)
  1  gacattgtgt tgacccagtc tcaaaaaatc gtgtccacat cagtaggagc cagggtcagc 61  gtcacctgca aggccagtca gaatgtgggt tctagtttag tctggtatca acagaaacca
```

-continued

```
121  ggtcaatctc ctaaaacact gatttactcg gcatccttcc ggtacagtgg agtccctgat 181  cgcttcacag gcagtggatc tgggacagat tcactctca ccatcagcaa tgtgcagtct 241  gaagacttgg cagattattt ctgtcaacaa tataataact atccgctcac gttcggtgct 301  gggaccaagc tggagctgaa a
```

Protein Sequence Defining the Kappa Chain Variable Region of the
07F01 Antibody
(SEQ ID NO: 4)
```
  1  divltqsqki vstsvgarvs vtckasqnvg sslvwyqqkp gqspktliys asfrysgvpd 61  rftgsgsgtd ftltisnvqs edladyfcqq ynnypltfga gtklelk
```

Nucleic Acid Sequence Encoding the Heavy Chain Variable Region of the
12B11 Antibody
(SEQ ID NO: 11)
```
  1  gaggtgcagt tagtggagtc tgggggaggc ttagtgaagc ctggagggtc cctgaaactc 61  tcctgtgcag cctctggatt cactttcagt acctatgcca tgtcttggat tcgccagact 121  ccggagaaga ggctggagtg gtcgcagga atcactaatg gtggtagttt cacctactat 181  ccagacactg tgaaggacg attcaccatc tccagagaca atgccaggaa catcctatac 241  ctgcaaatga gcggtctgag gtctgaggac acggccatgt attattgtgc aagacagggt 301  tactatggtt taactttga ctactggggc caaggcacca ctctcacagt ctcctca
```

Protein Sequence Defining the Heavy Chain Variable Region of the
12B11 Antibody
(SEQ ID NO: 12)
```
  1  evqlvesggg lvkpggslkl scaasgftfs tyamswirqt pekrlewvag itnggsftyy

61  pdtvkgrfti srdnarnily lqmsglrsed tamyycargg yygvnfdywg qgttltvss
```

Nucleic Acid Sequence Encoding the Kappa Chain Variable Region of the
12B11 Antibody
(SEQ ID NO: 13)
```
  1  gatgctgtga tgacccaaac tccactctcc ctgcctgtca gtcttggaga tcaagcctcc 61  atctcttgca ggtctagtca gagccttgaa aacagtaacg gaaacactta tttgaactgg 121  tacctccaga accaggcca gtctccacag ctcctgatct cagggtttc caaccgattt 181  tctggggtcc cagacaggtt cagtggtagt ggatcaggga cagatttcac actgaaaatc 241  atcagagtgg aggctgagga tttgggactt tatttctgcc tccaagttac acatgtcccg 301  cacacgttcg gaggggggac caaactggaa ttaaaa
```

Protein Sequence Defining the Kappa Chain Variable Region of the
12B11 Antibody
(SEQ ID NO: 14)
```
  1  davmtqtpls lpvslgdqas iscrssqsle nsngntylnw ylqkpgqspq lliyrvsnrf

61  sgvpdrfsgs gsgtdftlki irveaedlgl yfclqvthvp htfgggtkle lk
```

Nucleic Acid Sequence Encoding the Heavy Chain Variable Region of the
17F06 Antibody
(SEQ ID NO: 21)
```
  1  gaagtgaagc tggtggagtc gggggaggc ttagtgaagc ctggagcgtc tctgaaactc 61  tcctgtgcag cctctggatt catttcagt cctatggca tgtcttgggt tcgccagact 121  tcagacaaga ggctggagtg gtcgcttcc attagtagtg gtggtggtac acctactat 181  ctagacactg taaagggccg attcaccatc tccagagaga atgccaagga caccctgtac 241  ctgcaaatga gtggtctgaa gtctgaagac acggccttgt attactgtac aagaggccaa 301  tggttactaa agtttgctta ctggggccaa gggactctgg tcactgtctc tgca
```

Protein Sequence Defining the Heavy Chain Variable Region of the
17F06 Antibody
(SEQ ID NO: 22)
```
  1  evklvesggg lvkpgaslkl scaasgfifs sygmswvrqt sdkrlewvas issgggttyy

61  ldtvkgrfti srenakdtly lqmsglksed talyyctrgq wllkfaywgq gtlvtvsa
```

Nucleic Acid Sequence Encoding the Lambda Chain Variable Region of the
17F06 Antibody
(SEQ ID NO: 23)

```
  1  caacttgtgc tcactcagtc atcttcagcc tctttctccc tgggagcctc agcaaaactc 61  acgtgcacct tgagtagtca gcacactacg tacaccattg aatggtatca gcaactgcca 121  ctcaagcctc ctaagtatgt gatggagctt aagaaagatg gaagccacag cacaggtgtt 181  gggattcctg atcgcttctc tggatccagc tctggtgctg atcgctacct taccatttcc 241  aacatccagc ctgaagatga agcaatatac atctgtggtg tgggtgagac aattgaggac 301  caatttgtgt atgttttcgg cggtggcacc aaggtcactg tccta
```

Protein Sequence Defining the Lambda Chain Variable Region of the
17F06 Antibody
(SEQ ID NO: 24)

```
  1  qlvltqsssa sfslgasakl tctlssqhtt ytiewyqqlp lkppkyvmel kkdgshstgv

61  gipdrfsgss sgadryltis niqpedeaiy icgvgetied qfvyvfgggt kvtvl
```

Nucleic Acid Sequence Encoding the Heavy Chain Variable Region of the
18H09 Antibody
(SEQ ID NO: 31)

```
  1  gaggtgcagc ttcaggagtc aggacctagc ctcgtgaaac cttctcagac tctgtccctc 61  acctgttatg tcactggcga ctccatcacc agtgattact ggaattggat ccggaaattc 121  ccaggaaata aacttgagta catgggatat atcagctaca gtggtagcac ttactacaat 181  ccatctctca aaagtcgaat ctccatcact cgagacacat ccaagaacca gttctacctt 241  cggttgaatt ctgtgactac tgaggacaca gccacatatt actgtgcaag aacccatata 301  cttacgattg cttactgggg ccaagggact ctggtcactg tctctgca
```

Protein Sequence Defining the Heavy Chain Variable Region of the
18H09 Antibody
(SEQ ID NO: 32)

```
  1  evqlqesgps lvkpsqtlsl tcyvtgdsit sdywnwirkf pgnkleymgy isysgstyyn

61  pslksrisit rdtsknqfyl rlnsvttedt atyycarthi ltiaywgqgt lvtvsa
```

Nucleic Acid Sequence Encoding the Lambda Chain Variable Region of the
18H09 Antibody
(SEQ ID NO: 33)

```
  1  caggctgttg tgactcagga atctgcactc accacatcac ctggtgaaac agtcacactc 61  acttgtcgct caagtgccgg ggctgttaca actagtaact tgccaactg gtccaagaa 121  aaaccagatc atttattcac tggtctaata ggtgatacca acatccgagc tccaggtgtt 181  cctgccagat tctcaggctc cctgattgga acaaggctg ccctcaccat cacagggca 241  cagactgagg atgaggcaat atatttctgt gctctttggt acagcaacca ttactgggtg 301  ttcggtggag gaaccaaact gactgtccta
```

Protein Sequence Defining the Lambda Chain Variable Region of the
18H09 Antibody
(SEQ ID NO: 34)

```
  1  qavvtqesal ttspgetvtl tcrssagavt tsnfanwvqe kpdhlftgli gdtnirapgv 61  parfsgslig dkaaltitga qtedeaiyfc alwysnhywv fgggtkltvl
```

Nucleic Acid Sequence Encoding the Heavy Chain Variable Region of the
29B06 Antibody
(SEQ ID NO: 41)

```
  1  gaggtgcagc ttcaggagtc aggacctagc ctcgtgaaac cttctcagac tctgtccctc 61  acctgttctg tcactggcga ctccatcacc agtggttact ggaactggat ccggaaattc 121  ccagggaata aacttgagta catggggtac ataagctaca gtggtaaaac ttactacaat 181  ccatctctca aaagtcgaat ctccatcact cgagacacat ccaagaacca ttactacctg 241  cagttgattt ctgtgactgc tgaggacaca gccacatatt actgtgcaag gtctaagtac 301  gactatgcta tggactactg gggtcaagga acctcagtca ccgtctcctc a
```

```
Protein Sequence Defining the Heavy Chain Variable Region of the
29B06 Antibody
                                                      (SEQ ID NO: 42)
  1  evqlqesgps lvkpsqtlsl tcsvtgdsit sgywnwirkf pgnkleymgy isysgktyyn 61  pslksrisit rdtsknhyyl qlisvtaedt atyycarsky dyamdywgqg tsvtvss Nucleic Acid Sequence Encoding the Kappa Chain Variable Region of the
29B06 Antibody
                                                      (SEQ ID NO: 43)
  1  gacattgtgc tgacccaatc tccagcttct ttggctgtgt ctctaggaca gagggccacc 61  atctcctgca gagccagcga aattgttgat aattttggca ttagttttat gaactggttc 121  caacagaaac caggacagcc acccaaactc ctcatctatg ctgcatccaa ccaaggatcc 181  ggggtccctg ccaggtttag tggcagtggg tctgggacag acttcagcct caacatccat 241  cctgtggagg aggatgatac tgcaatgtat ttctgtcagc aaagtaagga ggttcctccg 301  acgttcggtg gaggcaccaa gctggaaatc aaa Protein Sequence Defining the Kappa Chain Variable Region of the
29B06 Antibody
                                                      (SEQ ID NO: 44)
  1  divltqspas lavslgqrat iscraseivd nfgisfmnwf qqkpgqppkl liyaasnqgs 61  gvparfsgsg sgtdfslnih pveeddtamy fcqqskevpp tfgggtklei k
```

The amino acid sequences defining the immunoglobulin heavy chain variable regions for the antibodies produced in Example 2 are aligned in FIG. 2. Amino terminal signal peptide sequences (for expression/secretion) are not shown. $CDR_1$, $CDR_2$, and $CDR_3$ (Kabat definition) are identified by boxes. FIG. 3 shows an alignment of the separate $CDR_1$, $CDR_2$, and $CDR_3$ sequences for each antibody.

The amino acid sequences defining the immunoglobulin light chain variable regions of the antibodies in Example 2 are aligned in FIG. 4. Amino terminal signal peptide sequences (for expression/secretion) are not shown. $CDR_1$, $CDR_2$ and $CDR_3$ are identified by boxes. FIG. 5 shows an alignment of the separate $CDR_1$, $CDR_2$, and $CDR_3$ sequences for each antibody.

Table 1 shows the SEQ ID NO. of each sequence discussed in this Example.

TABLE 1

| SEQ. ID NO. | Nucleic Acid or Protein |
|---|---|
| 1 | 07F01 Heavy Chain Variable Region-nucleic acid |
| 2 | 07F01 Heavy Chain Variable Region-protein |
| 3 | 07F01 Light (kappa) Chain Variable Region-nucleic acid |
| 4 | 07F01 Light (kappa) Chain Variable Region-protein |
| 5 | 07F01 Heavy Chain $CDR_1$ |
| 6 | 07F01 Heavy Chain $CDR_2$ |
| 7 | 07F01 Heavy Chain $CDR_3$ |
| 8 | 07F01 Light (kappa) Chain $CDR_1$ |
| 9 | 07F01 Light (kappa) Chain $CDR_2$ |
| 10 | 07F01 Light (kappa) Chain $CDR_3$ |
| 11 | 12B11 Heavy Chain Variable Region-nucleic acid |
| 12 | 12B11 Heavy Chain Variable Region-protein |
| 13 | 12B11 Light (kappa) Chain Variable Region-nucleic acid |
| 14 | 12B11 Light (kappa) Chain Variable Region-protein |
| 15 | 12B11 Heavy Chain $CDR_1$ |
| 16 | 12B11 Heavy Chain $CDR_2$ |
| 17 | 12B11 Heavy Chain $CDR_3$ |
| 18 | 12B11 Light (kappa) Chain $CDR_1$ |
| 19 | 12B11 Light (kappa) Chain $CDR_2$ |
| 20 | 12B11 Light (kappa) Chain $CDR_3$ |
| 21 | 17F06 Heavy Chain Variable Region-nucleic acid |
| 22 | 17F06 Heavy Chain Variable Region-protein |
| 23 | 17F06 Light (lambda) Chain Variable Region-nucleic acid |
| 24 | 17F06 Light (lambda) Chain Variable Region-protein |
| 25 | 17F06 Heavy Chain $CDR_1$ |
| 26 | 17F06 Heavy Chain $CDR_2$ |
| 27 | 17F06 Heavy Chain $CDR_3$ |
| 28 | 17F06 Light (lambda) Chain $CDR_1$ |
| 29 | 17F06 Light (lambda) Chain $CDR_2$ |
| 30 | 17F06 Light (lambda) Chain $CDR_3$ |
| 31 | 18H09 Heavy Chain Variable Region-nucleic acid |
| 32 | 18H09 Heavy Chain Variable Region-protein |
| 33 | 18H09 Light (lambda) Chain Variable Region-nucleic acid |
| 34 | 18H09 Light (lambda) Chain Variable Region-protein |
| 35 | 18H09 Heavy Chain $CDR_1$ |
| 36 | 18H09 Heavy Chain $CDR_2$ |
| 37 | 18H09 Heavy Chain $CDR_3$ |
| 38 | 18H09 Light (lambda) Chain $CDR_1$ |
| 39 | 18H09 Light (lambda) Chain $CDR_2$ |
| 40 | 18H09 Light (lambda) Chain $CDR_3$ |
| 41 | 29B06 Heavy Chain Variable Region-nucleic acid |
| 42 | 29B06 Heavy Chain Variable Region-protein |
| 43 | 29B06 Light (kappa) Chain Variable Region-nucleic acid |
| 44 | 29B06 Light (kappa) Chain Variable Region-protein |
| 45 | 29B06 Heavy Chain $CDR_1$ |
| 46 | 29B06 Heavy Chain $CDR_2$ |
| 47 | 29B06 Heavy Chain $CDR_3$ |
| 48 | 29B06 Light (kappa) Chain $CDR_1$ |
| 49 | 29B06 Light (kappa) Chain $CDR_2$ |
| 50 | 29B06 Light (kappa) Chain $CDR_3$ |

Mouse monoclonal antibody heavy chain CDR sequences (Kabat, Chothia, and IMGT definitions) are shown in Table 2.

TABLE 2

| | CDR1 | CDR2 | CDR3 |
|---|---|---|---|
| | Kabat | | |
| 07F01 | RHWMS (SEQ ID NO: 5) | EINPDSRTINYTPSLKE (SEQ ID NO: 6) | RVRIHYYGAMDC (SEQ ID NO: 7) |

TABLE 2-continued

| | CDR1 | CDR2 | CDR3 |
|---|---|---|---|
| 12B11 | TYAMS (SEQ ID NO: 15) | GITNGGSFTYYPDTVKG (SEQ ID NO: 16) | QGYYGVNFDY (SEQ ID NO: 17) |
| 17F06 | SYGMS (SEQ ID NO: 25) | SISSGGGTTYYLDTVKG (SEQ ID NO: 26) | GQWLLKFAY (SEQ ID NO: 27) |
| 18H09 | SDYWN (SEQ ID NO: 35) | YISYSGSTYYNPSLK (SEQ ID NO: 36) | THILTIAY (SEQ ID NO: 37) |
| 29B06 | SGYWN (SEQ ID NO: 45) | YISYSGKTYYNPSLKS (SEQ ID NO: 46) | SKYDYAMDY (SEQ ID NO: 47) |
| Chothia | | | |
| 07F01 | GFDFSRH (SEQ ID NO: 51) | NPDSRT (SEQ ID NO: 52) | RVRIHYYGAMDC (SEQ ID NO: 7) |
| 12B11 | GFTFSTY (SEQ ID NO: 53) | TNGGSF (SEQ ID NO: 54) | QGYYGVNFDY (SEQ ID NO: 17) |
| 17F06 | GFIFSSY (SEQ ID NO: 55) | SSGGGT (SEQ ID NO: 56) | GQWLLKFAY (SEQ ID NO: 27) |
| 18H09 | GDSITSD (SEQ ID NO: 57) | SYSGS (SEQ ID NO: 58) | THILTIAY (SEQ ID NO: 37) |
| 29B06 | GDSITSG (SEQ ID NO: 59) | SYSGK (SEQ ID NO: 60) | SKYDYAMDY (SEQ ID NO: 47) |
| IMGT | | | |
| 07F01 | GFDFSRHW (SEQ ID NO: 61) | INPDSRTI (SEQ ID NO: 62) | ARRVRIHYYGAMDC (SEQ ID NO: 63) |
| 12B11 | GFTFSTYA (SEQ ID NO: 64) | ITNGGSFT (SEQ ID NO: 65) | ARQGYYGVNFDY (SEQ ID NO: 66) |
| 17F06 | GFIFSSYG (SEQ ID NO: 67) | ISSGGGTT (SEQ ID NO: 68) | TRGQWLLKFAY (SEQ ID NO: 69) |
| 18H09 | GDSITSDY (SEQ ID NO: 70) | ISYSGST (SEQ ID NO: 71) | ARTHILTIAY (SEQ ID NO: 72) |
| 29B06 | GDSITSGY (SEQ ID NO: 73) | ISYSGKT (SEQ ID NO: 74) | ARSKYDYAMDY (SEQ ID NO: 75) |

Mouse monoclonal antibody Kappa light chain CDR sequences (Kabat, Chothia, and IMGT definitions) are shown in Table 3.

TABLE 3

| | CDR1 | CDR2 | CDR3 |
|---|---|---|---|
| Kabat/Chothia | | | |
| 07F01 | KASQNVGSSLV (SEQ ID NO: 8) | SASFRYS (SEQ ID NO: 9) | QQYNNYPLT (SEQ ID NO: 10) |
| 12B11 | RSSQSLENSNGNTYLN (SEQ ID NO: 18) | RVSNRFS (SEQ ID NO: 19) | LQVTHVPHT (SEQ ID NO: 20) |
| 17F06 | TLSSQHTTYTIE (SEQ ID NO: 28) | LKKDGSHSTGV (SEQ ID NO: 29) | GVGETIEDQFVYV (SEQ ID NO: 30) |
| 18H09 | RSSAGAVTTSNFAN (SEQ ID NO: 38) | DTNIRAP (SEQ ID NO: 39) | ALWYSNHYWV (SEQ ID NO: 40) |
| 29B06 | RASEIVDNFGISFMN (SEQ ID NO: 48) | AASNQGS (SEQ ID NO: 49) | QQSKEVPPT (SEQ ID NO: 50) |
| IMGT | | | |
| 07F01 | QNVGSS (SEQ ID NO: 76) | SAS | QQYNNYPLT (SEQ ID NO: 10) |
| 12B11 | QSLENSNGNTY (SEQ ID NO: 77) | RVS | LQVTHVPHT (SEQ ID NO: 20) |
| 17F06 | SQHTTYT (SEQ ID NO: 78) | LKKDGSH (SEQ ID NO: 79) | GVGETIEDQFVYV (SEQ ID NO: 30) |
| 18H09 | AGAVTTSNF (SEQ ID NO: 80) | DTN | ALWYSNHYWV (SEQ ID NO: 40) |
| 29B06 | EIVDNFGISF (SEQ ID NO: 81) | AAS | QQSKEVPPT (SEQ ID NO: 50) |

To create the complete heavy or kappa chain antibody sequences, each variable sequence above is combined with its respective constant region. For example, a complete heavy chain comprises a heavy variable sequence followed by the murine IgG1 or IgG2a heavy chain constant sequence, a complete kappa chain comprises a kappa variable sequence followed by the murine kappa light chain constant sequence, and a complete lambda chain comprises a lambda variable sequence followed by the murine lambda IGLC1 or IGLC2 light chain constant sequence.

Nucleic Acid Sequence Encoding the Murine IgG1 Heavy Chain Constant Region
(SEQ ID NO: 82)

```
  1 gccaaaacga caccccatc tgtctatcca ctggcccctg gatctgctgc ccaaactaac
 61 tccatggtga ccctgggatg cctggtcaag ggctatttcc ctgagccagt gacagtgacc
121 tggaactctg gatccctgtc cagcggtgtg cacaccttcc cagctgtcct gcagtctgac
181 ctctacactc tgagcagctc agtgactgtc ccctccagca cctggcccag cgagaccgtc
241 acctgcaacg ttgcccaccc ggccagcagc accaaggtgg acaagaaaat tgtgcccagg
301 gattgtggtt gtaagccttg catatgtaca gtcccagaag tatcatctgt cttcatcttc
```

-continued

```
361  cccccaaagc caaggatgt gctcaccatt actctgactc ctaaggtcac gtgtgttgtg
421  gtagacatca gcaaggatga tcccgaggtc cagttcagct ggtttgtaga tgatgtggag
481  gtgcacacag ctcagacgca accccgggag gagcagttca acagcacttt ccgctcagtc
541  agtgaacttc ccatcatgca ccaggactgg ctcaatggca aggagttcaa atgcagggtc
601  aacagtgcag ctttccctgc ccccatcgag aaaaccatct ccaaaccaa aggcagaccg
661  aaggctccac aggtgtacac cattccacct cccaaggagc agatgccaa ggataaagtc
721  agtctgacct gcatgataac agacttcttc cctgaagaca ttactgtgga gtggcagtgg
781  aatgggcagc cagcggagaa ctacaagaac actcagccca tcatggacac agatggctct
841  tacttcgtct acagcaagct caatgtgcag aagagcaact gggaggcagg aaatactttc
901  acctgctctg tgttacatga gggcctgcac aaccaccata ctgagaagag cctctcccac
961  tctcctggta aa
```

Protein Sequence Defining the Murine IgG1 Heavy Chain Constant Region
(SEQ ID NO: 83)

```
  1  akttppsvyp lapgsaaqtn smvtlgclvk gyfpepvtvt wnsgslssgv htfpavlqsd
 61  lytlsssvtv psstwpsetv tcnvahpass tkvdkkivpr dcgckpcict vpevssvfif
121  ppkpkdvlti tltpkvtcvv vdiskddpev qfswfvddve vhtaqtqpre eqfnstfrsv
181  selpimhqdw lngkefkcrv nsaafpapie ktisktkgrp kapqvytipp pkeqmakdkv
241  sltcmitdff peditvewqw ngqpaenykn tqpimdtdgs yfvysklnvq ksnweagntf
301  tcsvlheglh nhhtekslsh spgk
```

Nucleic Acid Sequence Encoding the Murine IgG2a Heavy Chain Constant Region
(SEQ ID NO: 84)

```
  1  gccaaaacaa cagcccccatc ggtctatcca ctggcccctg tgtgtggaga tacaactggc
 61  tcctcggtga ctctaggatg cctggtcaag ggttatttcc ctgagccagt gaccttgacc
121  tggaactctg gatccctgtc cagtggtgtg cacaccttcc cagctgtcct gcagtctgac
181  ctctacaccc tcagcagctc agtgactgta acctcgagca cctggcccag ccagtccatc
241  acctgcaatg tggcccaccc ggcaagcagc accaaggtgg acaagaaaat tgagcccaga
301  gggcccacaa tcaagccctg tcctccatgc aaatgcccag cacctaacct cttgggtgga
361  ccatccgtct tcatcttccc tccaaagatc aaggatgtac tcatgatctc cctgagcccc
421  atagtcacat gtgtggtggt ggatgtgagc gaggatgacc cagatgtcca gatcagctgg
481  tttgtgaaca acgtggaagt acacacagct cagacacaaa cccatagaga ggattacaac
541  agtactctcc gggtggtcag tgccctcccc atccagcacc aggactggat gagtggcaag
601  gagttcaaat gcaaggtcaa caacaaagac ctcccagcgc ccatcgagag aaccatctca
661  aaacccaaag ggtcagtaag agctccacag gtatatgtct tgcctccacc agaagaagag
721  atgactaaga acaggtcac tctgacctgc atggtcacag acttcatgcc tgaagacatt
781  tacgtggagt ggaccaacaa cgggaaaaca gagctaaact acaagaacac tgaaccagtc
841  ctggactctg atggttctta cttcatgtac agcaagctga gagtggaaaa aagaactgg
901  gtggaaagaa atagcactc ctgttcagtg gtccacgagg gtctgcacaa tcaccacacg
961  actaagagct ctcccggac tccgggtaaa
```

Protein Sequence Defining the Murine IgG2a Heavy Chain Constant Region
(SEQ ID NO: 85)

```
  1  akttapsvyp lapvcgdttg ssvtlgclvk gyfpepvtvt wnsgslssgv htfpavlqsd
 61  lytlsssvtv tsstwpsqsi tcnvahpass tkvdkkiepr gptikpcppc kcpapnllgg
121  psvfifppki kdvlmislsp ivtcvvvdvs eddpdvqisw fvnnvevhta qtqthredyn
```

```
181 stlrvvsalp iqhqdwmsgk efkckvnnkd lpapiertis kpkgsvrapq vyvlpppeee 241 mtkkqvtltc mvtdfmpedi yvewtnngkt elnykntepv ldsdgsyfmy sklrvekknw 301 vernsyscsv vheglhnhht tksfsrtpgk
```

Nucleic Acid Sequence Encoding the Murine Kappa Light Chain Constant Region
(SEQ ID NO: 86)
```
  1 cgggctgatg ctgcaccaac tgtatccatc ttcccaccat ccagtgagca gttaacatct 61 ggaggtgcct cagtcgtgtg cttcttgaac aacttctacc ccaaagacat caatgtcaag 121 tggaagattg atggcagtga acgacaaaat ggcgtcctga acagttggac tgatcaggac 181 agcaaagaca gcacctacag catgagcagc accctcacgt tgaccaagga cgagtatgaa 241 cgacataaca gctatacctg tgaggccact cacaagacat caacttcacc cattgtcaag 301 agcttcaaca ggaatgagtg t
```

Protein Sequence Defining the Murine Kappa Light Chain Constant Region
(SEQ ID NO: 87)
```
  1 radaaptvsi fppsseqlts ggasvvcfln nfypkdinvk wkidgserqn gvlnswtdqd 61 skdstysmss tltltkdeye rhnsytceat hktstspivk sfnrnec
```

Nucleic Acid Sequence Encoding the Murine Lambda (IGLC1) Light Chain Constant Region
(SEQ ID NO: 88)
```
  1 ggccagccca agtcttcgcc atcagtcacc ctgtttccac cttcctctga agagctcgag 61 actaacaagg ccacactggt gtgtacgatc actgatttct acccaggtgt ggtgacagtg 121 gactggaagg tagatggtac ccctgtcact cagggtatgg agacaaccca gccttccaaa 181 cagagcaaca acaagtacat ggctagcagc tacctgaccc tgacagcaag agcatgggaa 241 aggcatagca gttacagctg ccaggtcact catgaaggtc acactgtgga agagtttg 301 tcccgtgctg actgttcc
```

Protein Sequence Defining the Murine Lambda (IGLC1) Light Chain Constant Region
(SEQ ID NO: 89)
```
  1 gqpksspsvt lfppsseele tnkatlvcti tdfypgvvtv dwkvdgtpvt qgmettqpsk 61 qsnnkymass yltltarawe rhssyscqvt heghtveksl sradcs
```

Nucleic Acid Sequence Encoding the Murine Lambda (IGLC2) Light Chain Constant Region
(SEQ ID NO: 90)
```
  1 ggtcagccca agtccactcc cactctcacc gtgtttccac cttcctctga ggagctcaag 61 gaaaacaaag ccacactggt gtgtctgatt tccaacttt ccccgagtgg tgtgacagtg 121 gcctggaagg caaatggtac acctatcacc cagggtgtgg acacttcaaa tcccaccaaa 181 gagggcaaca agttcatggc cagcagcttc ctacatttga catcggacca gtggagatct 241 cacaacagtt ttacctgtca agttacacat gaagggggaca ctgtggagaa gagtctgtct 301 cctgcagaat gtctc
```

Protein Sequence Defining the Murine Lambda (IGLC2) Light Chain Constant Region
(SEQ ID NO: 91)
```
  1 gqpkstptlt vfppsseelk enkatlvcli snfspsgvtv awkangtpit qgvdtsnptk 61 egnkfmassf lhltsdqwrs hnsftcqvth egdtveksls paecl
```

The following sequences represent the actual or contemplated full length heavy and light chain sequence (i.e., containing both the variable and constant regions sequences) for each antibody described in this Example. Signal sequences for proper secretion of the antibodies (e.g., signal sequences at the 5' end of the DNA sequences or the amino terminal end of the protein sequences) are not shown in the full length heavy and light chain sequences disclosed herein and are not included in the final secreted protein. Also not shown are stop codons for termination of translation required at the 3' end of the DNA sequences. It is within ordinary skill in the art to select a signal sequence and/or a stop codon for expression of the disclosed full length IgG heavy chain and light chain sequences. It is also contemplated that the variable region sequences can be ligated to other constant region sequences to produce active full length IgG heavy and light chains.

Nucleic Acid Sequence Encoding the Full Length Heavy Chain Sequence (Heavy
Chain Variable Region and IgG1 Constant Region) of 07F01
(SEQ ID NO: 92)

```
   1 gaggtgaagc ttctcgagtc tggaggtggc ctggtgcagc cgggtggatc cctgaaactc 61 tcctgtgcag cctcaggatt cgattttagt agacactgga tgagttgggt ccggctggct 121 ccagggaaag gctagaatg gatcgcagaa attaatccag atagcagaac gataaactat 181 acgccatctc taaaggagaa attcatcatc tccagagaca cgccaaaaa ttcgctgttt 241 ctgcaaatga cagagtgag atctgaggac acagcccttt attactgtgc aagacgggta 301 agaattcatt actacggcgc tatggactgc tggggtcaag aacctcagt caccgtctcc 361 tcagccaaaa cgacacccc atctgtctat ccactggccc ctggatctgc tgcccaaact 421 aactccatgg tgaccctggg atgcctggtc aagggctatt ccctgagcc agtgacagtg 481 acctggaact ctggatccct gtccagcggt gtgcacacct tcccagctgt cctgcagtct 541 gacctctaca ctctgagcag ctcagtgact gtcccctcca gcacctggcc cagcgagacc 601 gtcacctgca acgttgccca ccggccagc agcaccaagg tggacaagaa aattgtgccc 661 agggattgtg gttgtaagcc ttgcatatgt acagtccag aagtatcatc tgtcttcatc 721 ttccccccaa agcccaagga tgtgctcacc attactctga ctcctaaggt cacgtgtgtt 781 gtggtagaca tcagcaagga tgatcccgag gtccagttca gctggtttgt agatgatgtg 841 gaggtgcaca cagctcagac gcaaccccgg gaggagcagt tcaacagcac tttccgctca 901 gtcagtgaac ttcccatcat gcaccaggac tggctcaatg gcaaggagtt caaatgcagg 961 gtcaacagtg cagctttccc tgcccccatc gagaaaacca tctccaaaac caaaggcaga 1021 ccgaaggctc cacaggtgta caccattcca cctcccaagg agcagatggc caaggataaa 1081 gtcagtctga cctgcatgat aacagacttc ttccctgaag acattactgt ggagtggcag 1141 tggaatgggc agccagcgga gaactacaag aacactcagc ccatcatgga cacagatggc 1201 tcttacttcg tctacagcaa gctcaatgtg cagaagagca ctgggaggc aggaaatact 1261 ttcacctgct ctgtgttaca tgagggcctg cacaaccacc atactgagaa gagcctctcc 1321 cactctcctg gtaaa
```

Protein Sequence Defining the Full Length Heavy Chain Sequence (Heavy Chain
Variable Region and IgG1 Constant Region) of 07F01
(SEQ ID NO: 93)

```
   1 evkllesggg lvqpggslkl scaasgfdfs rhwmswvrla pgkglewiae inpdsrtiny 61 tpslkekfii srdnaknslf lqmnrvrsed talyycarrv rihyygamdc wgqgtsvtvs 121 sakttppsvy plapgsaaqt nsmvtlgclv kgyfpepvtv twnsgslssg vhtfpavlqs 181 dlytlsssvt vpsstwpset vtcnvahpas stkvdkkivp rdcgckpcic tvpevssvfi 241 fppkpkdvlt itltpkvtcv vvdiskddpe vqfswfvddv evhtaqtqpr eeqfnstfrs 301 vselpimhqd wlngkefkcr vnsaafpapi ektisktkgr pkapqvytip ppkeqmakdk 361 vsltcmitdf fpeditvewq wngqpaenyk ntqpimdtdg syfvysklnv qksnweagnt 421 ftcsvlhegl hnhhteksls hspgk
```

Nucleic Acid Sequence Encoding the Full Length Light Chain Sequence (Kappa
Chain Variable Region and Constant Region) of 07F01
(SEQ ID NO: 94)

```
   1 gacattgtgt tgacccagtc tcaaaaaatc gtgtccacat cagtaggagc cagggtcagc 61 gtcacctgca aggccagtca gaatgtgggt tctagtttag tctggtatca acagaaacca 121 ggtcaatctc ctaaaacact gatttactcg gcatccttcc ggtacagtgg agtccctgat 181 cgcttcacag gcagtggatc tgggacagat ttcactctca ccatcagcaa tgtgcagtct 241 gaagacttgg cagattattt ctgtcaacaa tataataact atccgctcac gttcggtgct
```

```
301 gggaccaagc tggagctgaa acgggctgat gctgcaccaa ctgtatccat cttcccacca 361 tccagtgagc agttaacatc tggaggtgcc tcagtcgtgt gcttcttgaa caacttctac 421 cccaaagaca tcaatgtcaa gtggaagatt gatggcagtg aacgacaaaa tggcgtcctg 481 aacagttgga ctgatcagga cagcaaagac agcacctaca gcatgagcag caccctcacg 541 ttgaccaagg acgagtatga acgacataac agctatacct gtgaggccac tcacaagaca 601 tcaacttcac ccattgtcaa gagcttcaac aggaatgagt gt
```

Protein Sequence Defining the Full Length Light Chain Sequence (Kappa Chain Variable Region and Constant Region) of 07F01

(SEQ ID NO: 95)
```
  1 divltqsqki vstsvgarvs vtckasqnvg sslvwyqqkp gqspktliys asfrysgvpd 61 rftgsgsgtd ftltisnvqs edladyfcqq ynnypltfga gtklelkrad aaptvsifpp 121 sseqltsgga svvcflnnfy pkdinvkwki dgserqngvl nswtdqdskd stysmsstlt 181 ltkdeyerhn sytceathkt stspivksfn rnec
```

Nucleic Acid Sequence Encoding the Full Length Heavy Chain Sequence (Heavy Chain Variable Region and IgG1 Constant Region) of 12B11

(SEQ ID NO: 96)
```
  1 gaggtgcagt tagtggagtc tggggaggc ttagtgaagc ctggagggtc cctgaaactc 61 tcctgtgcag cctctggatt cactttcagt acctatgcca tgtcttggat tcgccagact 121 ccggagaaga ggctggagtg ggtcgcagga atcactaatg gtggtagttt cacctactat 181 ccagacactg tgaagggacg attcaccatc tccagagaca atgccaggaa catcctatac 241 ctgcaaatga gcggtctgag gtctgaggac acggccatgt attattgtgc aagacagggt 301 tactatggtg ttaactttga ctactgggc caaggcacca ctctcacagt ctcctcagcc 361 aaaacgacac cccccatctgt ctatccactg gcccctggat ctgctgccca aactaactcc 421 atggtgaccc tgggatgcct ggtcaagggc tatttccctg agccagtgac agtgacctgg 481 aactctggat ccctgtccag cggtgtgcac accttcccag ctgtcctgca gtctgacctc 541 tacactctga gcagctcagt gactgtcccc tccagcacct ggcccagcga gaccgtcacc 601 tgcaacgttg cccacccggc cagcagcacc aaggtggaca agaaaattgt gcccagggat 661 tgtggttgta agccttgcat atgtacagtc ccagaagtat catctgtctt catcttcccc 721 ccaaagccca aggatgtgct caccattact ctgactccta aggtcacgtg tgttgtggta 781 gacatcagca aggatgatcc cgaggtccag ttcagctggt ttgtagatga tgtggaggtg 841 cacacagctc agacgcaacc ccgggaggag cagttcaaca gcactttccg ctcagtcagt 901 gaacttccca tcatgcacca ggactggctc aatggcaagg agttcaaatg cagggtcaac 961 agtgcagctt ccctgccccc catcgagaaa accatctcca aaaccaaagg cagaccgaag 1021 gctccacagg tgtacaccat tccacctccc aaggagcaga tggccaagga taaagtcagt 1081 ctgacctgca tgataacaga cttcttccct gaagacatta ctgtggagtg gcagtggaat 1141 gggcagccag cggagaacta caagaacact cagcccatca tggacacaga tggctcttac 1201 ttcgtctaca gcaagctcaa tgtgcagaag agcaactggg aggcaggaaa tactttcacc 1261 tgctctgtgt tacatgaggg cctgcacaac accatactg agaagagcct ctcccactct 1321 cctggtaaa
```

Protein Sequence Defining the Full Length Heavy Chain Sequence (Heavy Chain Variable Region and IgG1 Constant Region) of 12B11

(SEQ ID NO: 97)
```
  1 evqlvesggg lvkpggslkl scaasgftfs tyamswirqt pekrlewvag itnggsftyy 61 pdtvkgrfti srdnarnily lqmsglrsed tamyycarqg yygvnfdywg qgttltvssa 121 kttppsvypl apgsaaqtns mvtlgclvkg yfpepvtvtw nsgslssgvh tfpavlqsdl
```

-continued

```
181 ytlsssvtvp sstwpsetvt cnvahpasst kvdkkivprd cgckpcictv pevssvfifp 241 pkpkdvltit ltpkvtcvvv diskddpevq fswfvddvev htaqtqpree qfnstfrsvs 301 elpimhqdwl ngkefkcrvn saafpapiek tisktkgrpk apqvytippp keqmakdkvs 361 ltcmitdffp editvewqwn gqpaenyknt qpimdtdgsy fvysklnvqk snweagntft 421 csvlheglhn hhtekslshs pgk
```

Nucleic Acid Sequence Encoding the Full Length Light Chain Sequence (Kappa Chain Variable Region and Constant Region) of 12B11
(SEQ ID NO: 98)

```
  1 gatgctgtga tgacccaaac tccactctcc ctgcctgtca gtcttggaga tcaagcctcc 61 atctcttgca ggtctagtca gagccttgaa aacagtaacg gaaacactta tttgaactgg 121 tacctccaga aaccaggcca gtctccacag ctcctgatct acagggtttc aaccgattt 181 tctgggtcc cagacaggtt cagtggtagt ggatcaggga cagatttcac actgaaaatc 241 atcagagtgg aggctgagga tttgggactt tatttctgcc tccaagttac acatgtcccg 301 cacacgttcg gagggggggac caaactggaa ttaaaacggg ctgatgctgc accaactgta 361 tccatcttcc caccatccag tgagcagtta acatctggag gtgcctcagt cgtgtgcttc 421 ttgaacaact ctacccccaa agacatcaat gtcaagtgga agattgatgg cagtgaacga 481 caaaatggcg tcctgaacag ttggactgat caggacagca aagacagcac ctacagcatg 541 agcagcaccc tcacgttgac caaggacgag tatgaacgac ataacagcta tacctgtgag 601 gccactcaca agacatcaac ttcacccatt gtcaagagct caacaggaa tgagtgt
```

Protein Sequence Defining the Full Length Light Chain Sequence (Kappa Chain Variable Region and Constant Region) of 12B11
(SEQ ID NO: 99)

```
  1 davmtqtpls lpvslgdqas iscrssqsle nsngntylnw ylqkpgqspq lliyrvsnrf 61 sgvpdrfsgs gsgtdftlki irveaedlgl yfclqvthvp htfgggtkle lkradaaptv 121 sifppsseql tsggasvvcf lnnfypkdin vkwkidgser qngvinswtd qdskdstysm 181 sstltltkde yerhnsytce athktstspi vksfnrnec
```

Nucleic Acid Sequence Encoding the Full Length Heavy Chain Sequence (Heavy Chain Variable Region and IgG2A Constant Region) of 17F06
(SEQ ID NO: 100)

```
  1 gaagtgaagc tggtggagtc gggggaggc ttagtgaagc ctggagcgtc tctgaaactc 61 tcctgtgcag cctctggatt cattttcagt tcctatggca tgtcttgggt tcgccagact 121 tcagacaaga ggctggagtg gtcgcttcc attagtagtg gtggtggtac cacctactat 181 ctagacactg taaagggccg attcaccatc tccagagaga atgccaagga caccctgtac 241 ctgcaaatga gtggtctgaa gtctgaagac acggccttgt attactgtac aagaggccaa 301 tggttactaa agtttgctta ctggggccaa gggactctgg tcactgtctc tgcagccaaa 361 acaacagccc catcggtcta tccactggcc cctgtgtgtg gagatacaac tggctcctcg 421 gtgactctag gatgcctggt caagggttat ttccctgagc cagtgacctt gacctggaac 481 tctggatccc tgtccagtgg tgtgcacacc ttcccagctg tcctgcagtc tgacctctac 541 accctcagca gctcagtgac tgtaacctcg agcacctggc ccagccagtc catcacctgc 601 aatgtggccc acccggcaag cagcaccaag gtggacaaga aaattgagcc cagagggccc 661 acaatcaagc cctgtcctcc atgcaaatgc ccagcaccta acctcttggg tggaccatcc 721 gtcttcatct tccctccaaa gatcaaggat gtactcatga tctcccctgag ccccatagtc 781 acatgtgtgg tggtggatgt gagcgaggat gacccagatg tccagatcag ctggtttgtg 841 aacaacgtgg aagtacacac agctcagaca caaaccccata gagaggatta caacagtact 901 ctccgggtgg tcagtgccct ccccatccag caccaggact ggatgagtgg caaggagttc
```

```
 961 aaatgcaagg tcaacaacaa agacctccca gcgcccatcg agagaaccat ctcaaaaccc 1021 aaagggtcag taagagctcc acaggtatat gtcttgcctc caccagaaga agagatgact 1081 aagaaacagg tcactctgac ctgcatggtc acagacttca tgcctgaaga catttacgtg 1141 gagtggacca caacgggaa aacagagcta aactacaaga acactgaacc agtcctggac 1201 tctgatggtt cttacttcat gtacagcaag ctgagagtgg aaaagaagaa ctgggtggaa 1261 agaaatagct actcctgttc agtggtccac gagggtctgc acaatcacca cacgactaag 1321 agcttctccc ggactccggg taaa
```

Protein Sequence Defining the Full Length Heavy Chain Sequence (Heavy Chain Variable Region and IgG2A Constant Region) of 17F06

(SEQ ID NO: 101)

```
  1 evklvesggg lvkpgaslkl scaasgfifs sygmswvrqt sdkrlewvas issgggttyy 61 ldtvkgrfti srenakdtly lqmsglksed talyyctrgq wllkfaywgq gtlvtvsaak 121 ttapsvypla pvcgdttgss vtlgclvkgy fpepvtltwn sgslssgvht fpavlqsdly 181 tlsssvtvts stwpsqsitc nvahpasstk vdkkieprgp tikpcppckc papnllggps 241 vfifppkikd vlmislspiv tcvvvdvsed dpdvqiswfv nnvevhtaqt qthredynst 301 lrvvsalpiq hqdwmsgkef kckvnnkdlp apiertiskp kgsvrapqvy vlpppeeemt 361 kkqvtltcmv tdfmpediyv ewtnngktel nykntepvld sdgsyfmysk lrvekknwve 421 rnsyscsvvh eglhnhhttk sfsrtpgk
```

Nucleic Acid Sequence Encoding the Full Length Light Chain Sequence (Lambda Chain Variable Region and Constant Region (IGLC2)) of 17F06

(SEQ ID NO: 102)

```
  1 caacttgtgc tcactcagtc atcttcagcc tctttctccc tgggagcctc agcaaaactc 61 acgtgcacct tgagtagtca gcacactacg tacaccattg aatggtatca gcaactgcca 121 ctcaagcctc ctaagtatgt gatggagctt aagaaagatg gaagccacag cacaggtgtt 181 gggattcctg atcgcttctc tggatccagc tctggtgctg atcgctacct taccatttcc 241 aacatccagc ctgaagatga agcaatatac atctgtggtg tgggtgagac aattgaggac 301 caatttgtgt atgttttcgg cggtggcacc aaggtcactg tcctaggtca gcccaagtcc 361 actcccactc tcaccgtgtt tccaccttcc tctgaggagc tcaaggaaaa caaagccaca 421 ctggtgtgtc tgatttccaa cttttccccg agtggtgtga cagtggcctg aaggcaaat 481 ggtacaccta tcacccaggg tgtggacact tcaaatccca ccaaagaggg caacaagttc 541 atggccagca gcttcctaca tttgacatcg gaccagtgga gatctcacaa cagtttacc 601 tgtcaagtta cacatgaagg ggacactgtg gagaagagtc tgtctcctgc agaatgtctc
```

Protein Sequence Defining the Full Length Light Chain Sequence (Lambda Chain Variable Region and Constant Region (IGLC2)) of 17F06

(SEQ ID NO: 103)

```
  1 qlvltqsssa sfslgasakl tctlssqhtt ytiewyqqlp lkppkyvmel kkdgshstgv 61 gipdrfsgss sgadryltis niqpedeaiy icgvgetied qfvyvfgggt kvtvlgqpks 121 tptltvfpps seelkenkat lvclisnfsp sgvtvawkan gpitqgvdt snptkegnkf 181 massflhlts dqwrshnsft cqvthegdtv ekslspaecl
```

Nucleic Acid Sequence Encoding the Full Length Heavy Chain Sequence (Heavy Chain Variable Region and IgG1 Constant Region) of 18H09

(SEQ ID NO: 104)

```
  1 gaggtgcagc ttcaggagtc aggacctagc ctcgtgaaac cttctcagac tctgtccctc 61 acctgttatg tcactggcga ctccatcacc agtgattact ggaattggat ccggaaattc 121 ccaggaaata acttgagta catgggatat atcagctaca gtggtagcac ttactacaat 181 ccatctctca aaagtcgaat ctccatcact cgagacacat ccaagaacca gttctacctt 241 cggttgaatt ctgtgactac tgaggacaca gccacatatt actgtgcaag aacccatata
```

```
301 cttacgattg cttactgggg ccaagggact ctggtcactg tctctgcagc caaaacgaca
361 cccccatctg tctatccact ggcccctgga tctgctgccc aaactaactc catggtgacc
421 ctgggatgcc tggtcaaggg ctatttccct gagccagtga cagtgacctg aactctgga
481 tccctgtcca gcggtgtgca caccttccca gctgtcctgc agtctgacct ctacactctg
541 agcagctcag tgactgtccc ctccagcacc tggcccagcg agaccgtcac ctgcaacgtt
601 gcccacccgg ccagcagcac caaggtggac aagaaaattg tgcccaggga ttgtggttgt
661 aagccttgca tatgtacagt cccagaagta tcatctgtct tcatcttccc cccaaagccc
721 aaggatgtgc tcaccattac tctgactcct aaggtcacgt gtgttgtggt agacatcagc
781 aaggatgatc ccgaggtcca gttcagctgg tttgtagatg atgtggaggt gcacacagct
841 cagacgcaac cccgggagga gcagttcaac agcactttcc gctcagtcag tgaacttccc
901 atcatgcacc aggactggct caatggcaag gagttcaaat gcagggtcaa cagtgcagct
961 ttccctgccc ccatcgagaa aaccatctcc aaaaccaaag cagaccgaa ggctccacag
1021 gtgtacacca ttccacctcc caaggagcag atggccaagg ataaagtcag tctgacctgc
1081 atgataacag acttcttccc tgaagacatt actgtggagt ggcagtggaa tgggcagcca
1141 gcggagaact acaagaacac tcagcccatc atggacacag atggctctta cttcgtctac
1201 agcaagctca atgtgcagaa gagcaactgg gaggcaggaa atactttcac ctgctctgtg
1261 ttacatgagg gcctgcacaa ccaccatact gagaagagcc tctcccactc tcctggtaaa
```

Protein Sequence Defining the Full Length Heavy Chain Sequence (Heavy Chain Variable Region and IgG1 Constant Region) of 18H09

(SEQ ID NO: 105)
```
  1 evqlqesgps lvkpsqtlsl tcyvtgdsit sdywnwirkf pgnkleymgy isysgstyyn
 61 pslksrisit rdtsknqfyl rinsvttedt atyycarthi ltiaywgqgt lvtvsaaktt
121 ppsvyplapg saaqtnsmvt lgclvkgyfp epvtvtwnsg slssgvhtfp avlqsdlytl
181 sssvtvpsst wpsetvtcnv ahpasstkvd kkivprdcgc kpcictvpev ssvfifppkp
241 kdvltitltp kvtcvvvdis kddpevqfsw fvddvevhta qtqpreeqfn stfrsyselp
301 imhqdwlngk efkcrvnsaa fpapiektis ktkgrpkapq vytipppkeq makdkvsltc
361 mitdffpedi tvewqwngqp aenykntqpi mdtdgsyfvy sklnvqksnw eagntftcsv
421 lheglhnhht ekslshspgk
```

Nucleic Acid Sequence Encoding the Full Length Light Chain Sequence (Lambda Chain Variable Region and Constant Region (IGLC1)) of 18H09

(SEQ ID NO: 106)
```
  1 caggctgttg tgactcagga atctgcactc accacatcac ctggtgaaac agtcacactc
 61 acttgtcgct caagtgccgg ggctgttaca actagtaact ttgccaactg ggtccaagaa
121 aaaccagatc atttattcac tggtctaata ggtgatacca acatccgagc tccaggtgtt
181 cctgccagat tctcaggctc cctgattgga gacaaggctg ccctcaccat cacaggggca
241 cagactgagg atgaggcaat atatttctgt gctctttggt acagcaacca ttactgggtg
301 ttcggtggag gaaccaaact gactgtccta ggccagccca gtcttcgcc atcagtcacc
361 ctgtttccac cttcctctga agagctcgag actaacaagg ccacactggt gtgtacgatc
421 actgatttct acccaggtgt ggtgacagtg gactggaagt agatggtac ccctgtcact
481 cagggtatgg agacaaccca gccttccaaa cagagcaaca caagtacat ggctagcagc
541 tacctgaccc tgacagcaag agcatgggaa aggcatagca gttacagctg ccaggtcact
601 catgaaggtc acactgtgga gaagagtttg tcccgtgctg actgttcc
```

-continued

Protein Sequence Defining the Full Length Light Chain Sequence (Lambda Chain Variable Region and Constant Region (IGLC1)) of 18H09

(SEQ ID NO: 107)

```
  1 qavvtqesal ttspgetvtl tcrssagavt tsnfanwvqe kpdhlftgli gdtnirapgv 61 parfsgslig dkaaltitga qtedeaiyfc alwysnhywv fgggtkltvl gqpksspsvt 121 lfppsseele tnkatlvcti tdfypgvvtv dwkvdgtpvt qgmettqpsk qsnnkymass 181 yltltarawe rhssyscqvt heghtveksl sradcs
```

Nucleic Acid Sequence Encoding the Full Length Heavy Chain Sequence (Heavy Chain Variable Region and IgG1 Constant Region) of 29B06

(SEQ ID NO: 108)

```
   1 gaggtgcagc ttcaggagtc aggacctagc ctcgtgaaac cttctcagac tctgtccctc 61 acctgttctg tcactggcga ctccatcacc agtggttact ggaactggat ccggaaattc 121 ccagggaata aacttgagta catggggtac ataagctaca gtggtaaaac ttactacaat 181 ccatctctca aaagtcgaat ctccatcact cgagacacat ccaagaacca ttactacctg 241 cagttgattt ctgtgactgc tgaggacaca gccacatatt actgtgcaag gtctaagtac 301 gactatgcta tggactactg gggtcaagga acctcagtca ccgtctcctc agccaaaacg 361 acacccccat ctgtctatcc actggcccct ggatctgctg cccaaactaa ctccatggtg 421 accctgggat gcctggtcaa gggctatttc cctgagccag tgacagtgac ctggaactct 481 ggatccctgt ccagcggtgt gcacaccttc ccagctgtcc tgcagtctga cctctacact 541 ctgagcagct cagtgactgt cccctccagc acctggccca cgagaccgt cacctgcaac 601 gttgcccacc cggccagcag caccaaggtg gacaagaaaa ttgtgcccag ggattgtggt 661 tgtaagcctt gcatatgtac agtcccagaa gtatcatctg tcttcatctt cccccccaaag 721 cccaaggatg tgctcaccat tactctgact cctaaggtca cgtgtgttgt ggtagacatc 781 agcaaggatg atcccgaggt ccagttcagc tggtttgtag atgatgtgga ggtgcacaca 841 gctcagacgc aaccccggga ggagcagttc aacagcactt tccgctcagt cagtgaactt 901 cccatcatgc accaggactg gctcaatggc aaggagttca atgcagggt caacagtgca 961 gctttccctg cccccatcga gaaaaccatc tccaaaacca aaggcagacc gaaggctcca 1021 caggtgtaca ccattccacc tcccaaggag cagatggcca aggataaagt cagtctgacc 1081 tgcatgataa cagacttctt ccctgaagac attactgtgg agtggcagtg gaatgggcag 1141 ccagcggaga actacaagaa cactcagccc atcatggaca gatggctc ttacttcgtc 1201 tacagcaagc tcaatgtgca gaagagcaac tgggaggcag gaaatacttt cacctgctct 1261 gtgttacatg agggcctgca caaccaccat actgagaaga gcctctccca ctctcctggt 1321 aaa
```

Protein Sequence Defining the Full Length Heavy Chain Sequence (Heavy Chain Variable Region and IgG1 Constant Region) of 29B06

(SEQ ID NO: 109)

```
  1 evqlqesgps lvkpsqtlsl tcsvtgdsit sgywnwirkf pgnkleymgy isysgktyyn 61 pslksrisit rdtsknhyyl qlisvtaedt atyycarsky dyamdywgqg tsvtvssakt 121 tppsvyplap gsaaqtnsmv tlgclvkgyf pepvtvtwns gslssgvhtf pavlqsdlyt 181 lsssvtvpss twpsetvtcn vahpasstkv dkkivprdcg ckpcictvpe vssvfifppk 241 pkdvltitlt pkvtcvvvdi skddpevqfs wfvddvevht aqtqpreeqf nstfrsvsel 301 pimhqdwlng kefkcrvnsa afpapiekti sktkgrpkap qvytipppke qmakdkvslt 361 cmitdffped itvewqwngq paenykntqp imdtdgsyfv ysklnvqksn weagntftcs 421 vlheglhnhh tekslshspg k
```

Nucleic Acid Sequence Encoding the Full Length Light Chain Sequence (Kappa Chain Variable Region and Constant Region) of 29B06

(SEQ ID NO: 110)

```
  1 gacattgtgc tgacccaatc tccagcttct ttggctgtgt ctctaggaca gagggccacc 61 atctcctgca gagccagcga aattgttgat aattttggca ttagttttat gaactggttc 121 caacagaaac caggacagcc acccaaactc ctcatctatg ctgcatccaa ccaaggatcc 181 ggggtccctg ccaggtttag tggcagtggg tctgggacag acttcagcct caacatccat 241 cctgtggagg aggatgatac tgcaatgtat ttctgtcagc aaagtaagga ggttcctccg 301 acgttcggtg gaggcaccaa gctggaaatc aaacgggctg atgctgcacc aactgtatcc 361 atcttcccac catccagtga gcagttaaca tctggaggtg cctcagtcgt gtgcttcttg 421 aacaacttct accccaaaga catcaatgtc aagtggaaga ttgatggcag tgaacgacaa 481 aatggcgtcc tgaacagttg gactgatcag gacagcaaag acagcaccta cagcatgagc 541 agcaccctca cgttgaccaa ggacgagtat gaacgacata acagctatac ctgtgaggcc 601 actcacaaga catcaacttc acccattgtc aagagcttca acaggaatga gtgt
```

Protein Sequence Defining the Full Length Light Chain Sequence (Kappa Chain Variable Region and Constant Region) of 29B06

(SEQ ID NO: 111)

```
  1 divltqspas lavslgqrat iscraseivd nfgisfmnwf qqkpgqppkl liyaasnqgs 61 gvparfsgsg sgtdfslnih pveeddtamy fcqqskevpp tfgggtklei kradaaptvs 121 ifppsseqlt sggasvvcfl nnfypkdinv kwkidgserq ngvinswtdq dskdstysms 181 stltltkdey erhnsytcea thktstspiv ksfnrnec
```

Table 4 shows the correspondence between the full-length sequences of the antibodies discussed in this Example with those presented in the Sequence Listing.

TABLE 4

| SEQ ID NO. | Nucleic Acid or Protein |
|---|---|
| 92 | 07F01 Heavy Variable + IgG1 Constant-nucleic acid |
| 93 | 07F01 Heavy Variable + IgG1 Constant-protein |
| 94 | 07F01 Kappa Variable + Constant-nucleic acid |
| 95 | 07F01 Kappa Variable + Constant-protein |
| 96 | 12B11 Heavy Variable + IgG1 Constant-nucleic acid |
| 97 | 12B11 Heavy Variable + IgG1 Constant-protein |
| 98 | 12B11 Kappa Variable + Constant-nucleic acid |
| 99 | 12B11 Kappa Variable + Constant-protein |
| 100 | 17F06 Heavy Variable + IgG2A Constant-nucleic acid |
| 101 | 17F06 Heavy Variable + IgG2A Constant-protein |
| 102 | 17F06 Lambda Variable + Constant (IGLC2)-nucleic acid |
| 103 | 17F06 Lambda Variable + Constant (IGLC2)-protein |
| 104 | 18H09 Heavy Variable + IgG1 Constant-nucleic acid |
| 105 | 18H09 Heavy Variable + IgG1 Constant-protein |
| 106 | 18H09 Lambda Variable + Constant (IGLC1)-nucleic acid |
| 107 | 18H09 Lambda Variable + Constant (IGLC1)-protein |
| 108 | 29B06 Heavy Variable + IgG1 Constant-nucleic acid |
| 109 | 29B06 Heavy Variable + IgG1 Constant-protein |
| 110 | 29B06 Kappa Variable + Constant-nucleic acid |
| 111 | 29B06 Kappa Variable + Constant-protein |

Example 5

Binding Affinities

The binding affinities and kinetics of binding of antibodies 07F01, 29B06, 17F06, 18H09, and 12B11 to recombinant human RON-ECD/mFc fusion protein (rhRON ECD/mFc) and recombinant human RON SEMA and PSI domains (rhRON SEMA+PSI) (R&D Systems, Inc., Minneapolis, Minn.) were measured by surface plasmon resonance, using a BIACORE® T100 instrument (GE Healthcare, Piscataway, N.J.).

Rabbit anti-mouse IgGs (GE Healthcare) were immobilized on carboxymethylated dextran CM4 sensor chips (GE Healthcare) by amine coupling, according to a standard protocol. Analyses were performed at 25° C. and 37° C., using PBS containing 0.05% surfactant P20 as running buffer. The antibodies were captured in individual flow cells at a flow rate of 10 µl/min. Injection time was varied for each antibody to yield an Rmax between 30 and 60 RU. 250 µg/mL mouse Fc were injected at 30 µl/min for 120 seconds to block non-specific binding of antibodies to Fc portion of the protein when needed. Buffer, rhRon ECD/mFc or rhRON SEMA+PSI diluted in running buffer was injected sequentially over a reference surface (no antibody captured) and the active surface (antibody to be tested) for 300 seconds at 60 µl/minute. The dissociation phase was monitored for up to 3600 seconds. The surface was then regenerated with two 60-second injections of 10 mM Glycine-HCl, pH 1.7, at a flow rate of 60 µl/min. The rhRON ECD/mFc or rhRON SEMA+PSI concentration range tested was 0.625 nM to 20 nM.

Kinetic parameters were determined using the kinetic function of the BIAevaluation software (GE Healthcare) with double reference subtraction. Kinetic parameters for each antibody, $k_a$ (association rate constant), $k_d$ (dissociation rate constant) and $K_D$ (equilibrium dissociation constant) were determined. Kinetic values of the monoclonal antibodies on rhRON ECD/mFc at 25° C. and 37° C. are summarized in Table 5.

TABLE 5

Antibody Binding to rhRON ECD/mFc

| Antibody | | Measurements at 25° C. | | | | Measurements at 37° C. | | | |
|---|---|---|---|---|---|---|---|---|---|
| | | ka (1/Ms) | kd (1/s) | $K_D$ (M) | n | ka (1/Ms) | kd (1/s) | $K_D$ (M) | n |
| 07F01 | AVG | 4.0E+05 | 9.3E−05 | 2.3E−10 | 4 | 2.1E+06 | 3.5E−04 | 2.1E−10 | 3 |
| | STDEV | 7.1E+04 | 5.5E−06 | 3.4E−11 | | 2.4E+06 | 2.8E−04 | 7.1E−11 | |
| 29B06 | AVG | 2.0E+05 | 1.3E−04 | 6.5E−10 | 3 | 2.3E+06 | 7.0E−04 | 2.8E−10 | 3 |
| | STDEV | 3.5E+04 | 1.0E−05 | 1.2E−10 | | 1.3E+06 | 4.8E−04 | 7.8E−11 | |
| 17F06 | AVG | 1.7E+05 | 4.6E−08* | 2.9E−13* | 3 | 1.4E+05 | 2.4E−05 | 2.1E−10 | 3 |
| | STDEV | 4.8E+04 | 3.3E−08 | 1.7E−13 | | 3.1E+04 | 2.2E−05 | 2.4E−10 | |
| 18H09 | AVG | 3.3E+05 | 5.7E−05 | 2.2E−10 | 3 | 1.8E+06 | 7.0E−04 | 4.0E−10 | 1 |
| | STDEV | 1.5E+05 | 2.3E−05 | 1.6E−10 | | | | | |
| 12B11 | AVG | 1.2E+05 | 5.9E−05 | 5.0E−10 | 3 | 2.0E+05 | 2.0E−04 | 1.1E−09 | 3 |
| | STDEV | 2.8E+04 | 1.7E−05 | 4.6E−11 | | 1.1E+05 | 3.8E−05 | 4.6E−10 | |

*Outside instrument limit of detection

The data in Table 5 demonstrate that antibodies 07F01, 29B06, 17F06, 18H09, and 12B11 bind rhRON ECD/mFc with a $K_D$ of about 1 nM or less, 750 pM or less, 650 pM or less, 600 pM or less, 500 pM or less, 400 pM or less, 300 pM or less, 250 pM or less, 200 pM or less, 150 pM or less, 100 pM or less, or 50 pM or less.

Kinetic values of the monoclonal antibodies on rhRON SEMA+PSI at 25° C. and 37° C. are summarized in Table 6.

TABLE 6

Antibody Binding to rhRON SEMA + PSI

| Antibody | | Measurements at 25° C. | | | | Measurements at 37° C. | | | |
|---|---|---|---|---|---|---|---|---|---|
| | | ka (1/Ms) | kd (1/s) | $K_D$ (M) | n | ka (1/Ms) | kd (1/s) | $K_D$ (M) | n |
| 07F01 | AVG | 5.2E+06 | 3.6E−04 | 8.8E−11 | 3 | 2.0E+06 | 8.0E−04 | 4.0E−10 | 3 |
| | STDEV | 7.0E+06 | 4.3E−04 | 3.3E−11 | | 2.1E+05 | 7.5E−05 | 8.3E−12 | |
| 29B06 | AVG | 4.2E+05 | 7.0E−05 | 1.8E−10 | 3 | 5.2E+05 | 6.9E−04 | 1.3E−09 | 3 |
| | STDEV | 1.2E+05 | 8.7E−06 | 6.1E−11 | | 4.7E+04 | 4.9E−05 | 9.9E−11 | |
| 17F06 | AVG | 1.9E+05 | 1.4E−06 | 9.0E−12 | 4 | 2.6E+05 | 2.1E−05 | 1.3E−10 | 3 |
| | STDEV | 3.6E+04 | 1.7E−06 | 1.1E−11 | | 1.2E+05 | 2.9E−05 | 1.9E−10 | |
| 18H09 | AVG | 4.4E+05 | 3.8E−06 | 8.6E−12 | 3 | 5.8E+05 | 1.2E−04 | 2.2E−10 | 2 |
| | STDEV | 2.7E+04 | 6.3E−06 | 1.4E−11 | | 7.6E+04 | 5.3E−05 | 1.2E−10 | |
| 12B11 | AVG | No binding | | | 2 | No binding | | | |

The data in Table 6 demonstrate that antibodies 07F01, 29B06, 17F06 and 18H09 bind rhRON SEMA+PSI with a $K_D$ of about 1 nM or less, 750 pM or less, 650 pM or less, 600 pM or less, 500 pM or less, 400 pM or less, 300 pM or less, 250 pM or less, 200 pM or less, 150 pM or less, 100 pM or less, 75 pM or less, 50 pM or less, or 10 pM or less. Antibody 12B11 did not bind to rhRON SEMA+PSI.

Binding to cell surface human wild-type RON and the delta 160 RON variant by antibodies 29B06 and 07F01 was measured at 4° C., using Fluorescence Activated Cell Sorting (FACS). PC3 cells expressing the human wild-type RON, and HT29 cells expressing the delta 160 variant, were harvested using cell dissociation buffer (Invitrogen), washed twice with FACS buffer (PBS with 0.5% BSA), and treated for 10 minutes with Cyto Q Antibody diluent and FC receptor block (Innovex Biosciences, Richmond, Calif.). Purified antibodies were diluted in FACS buffer over a concentration range from 0.02 nM to 40 nM. Cells were incubated with 100 µl of antibody for one hour, washed with FACS buffer three times, and incubated for 45 minutes with goat anti-mouse PE-conjugated antibody (Jackson ImmunoResearch Laboratories, West Grove, Pa.). Cells were washed three times with FACS buffer, resuspended in 300 µl of FACS buffer, and analyzed using a Beckman Coulter Cytomics FC 500 FACS instrument. Results are summarized in Table 7.

TABLE 7

| | 29B06 | 07F01 |
|---|---|---|
| Human RON - $K_D$ (nM) | 0.133 | 0.032 |
| Human RON - $K_D$ range (nM) | 0.089-0.177 | 0.025-0.039 |
| Delta 160 RON - $K_D$ (nM) | 0.146 | 0.024 |
| Delta 160 RON - $K_D$ range (nM) | 0.100-0.192 | 0.020-0.029 |

The results in Table 7 demonstrate that antibodies 29B06 and 07F01 bind both wild-type RON and the delta 160 RON variant on the cell surface with similar affinity.

Example 6

Cell Surface Binding

Binding to cell surface wild-type RON and delta 160 RON at 4° C. was determined for antibodies 07F01, 12B11, 17F06, 18H09, and 29B06, using FACS. Cells expressing wild-type RON (PC3), and cells expressing delta 160 RON (HT-29), were harvested using cell dissociation buffer (Invitrogen), washed twice with FACS buffer (0.5% BSA PBS) and treated with CytoQ Antibody diluent and FC receptor block (Innovex). Purified antibodies were diluted at a concentration of 10 μg/ml, in FACS buffer. Cells were incubated with 100 μl of antibody mix for one hour, washed with FACS buffer three times, and incubated for 45 minutes with goat anti-mouse PE conjugated antibody (Jackson Immunoresearch Laboratories). Cells were washed three times with FACS buffer, resuspended in 300 μl of FACS buffer and analyzed using a Beckman Coulter Cytomics FC 500 FACS instrument. Percent binding as compared to murine IgG control is shown in Table 8.

TABLE 8

| Antibody | PC3 % cell surface binding | HT-29 % cell surface binding |
|---|---|---|
| 07F01 | 99.29 | 99.08 |
| 17F06 | 99.08 | 99.00 |
| 29B06 | 99.06 | 99.04 |
| 18H09 | 99.03 | 98.33 |
| 12B11 | 94.52 | 88.64 |
| mIgG | 5.50 | 5.62 |

The results in Table 8 demonstrate that antibodies 07F01, 29B06, 17F06, 18H09, and 12B11 bind both wild-type RON and the delta 160 RON variant expressed on the surface of cells.

Example 7

Receptor Internalization

Antibody-stimulated receptor internalization was measured using FACS. PC3 cells were used to measure antibody-stimulated internalization of the wild-type RON receptor. HT-29 cells were used for the delta 160 RON receptor variant. Antibodies were first conjugated with R-Phycocerthrin (Prozyme cat. No. PJ31K). All cells were washed with PBS and treated with CytoQ Antibody diluent and FC receptor block (Innovex). Cells were incubated with the antibodies (10 μg/ml) for 2 hours at 37° C. or at 4° C. The cells were transferred to 4° C., washed with an acidic solution (0.5 M NaCl, 0.18 M Acetic Acid, 0.5% Na azide) to strip off the antibody remaining on the cell surface, and fixed using BD CYTOFIX/CYTOPERM™ Plus kit (BD Biosciences, cat. No. 555028) to measure antibodies retained intracellularly due to internalization. At 37° C., cells can undergo antibody-mediated receptor internalization, and the process is inhibited at low temperature of 4° C., thus serving as a baseline (no internalization). The cells were analyzed using a Beckman Coulter Cytomics FC 500 FACS instrument. A lowered anti-RON median fluorescent intensity (MFI) and a left shift of the histograms at 4° C. compared to that obtained at 37° C. indicate antibody-induced receptor internalization. Receptor internalization was quantified by subtracting MFI at 4° C. from that at 37° C. Results are summarized in Table 9.

TABLE 9

| Antibody | MFI @ 37° C. − MFI @ 4° C. in PC-3 cells | MFI @ 37° C. − MFI @ 4° C. in HT-29 cells |
|---|---|---|
| mIgG control | −0.15 | −0.07 |
| 29B06 | 0.49 | 0.00 |
| 07F01 | 0.21 | 0.22 |
| 12B11 | 0.48 | 0.81 |

These results demonstrate that antibodies, 29B06, 07F01 and 12B11 induce receptor internalization in PC-3 cells expressing wild-type RON. Only 07F01 and 12B11 induce receptor internalization in HT-29 cells expressing delta 160 RON variant.

Example 8

Inhibition of MSP-RON Binding

Antibodies 07F01, 12B11, 17F06, 18H09, and 29B06 were tested for inhibition of MSP binding to hRON SEMA+PSI, as measured by electrochemiluminescence (ECL) assay as described in Example 3. The antibodies (concentration range: 0.006-10 μg/mL) were incubated for 45 minutes at room temperature.

Figure 6:
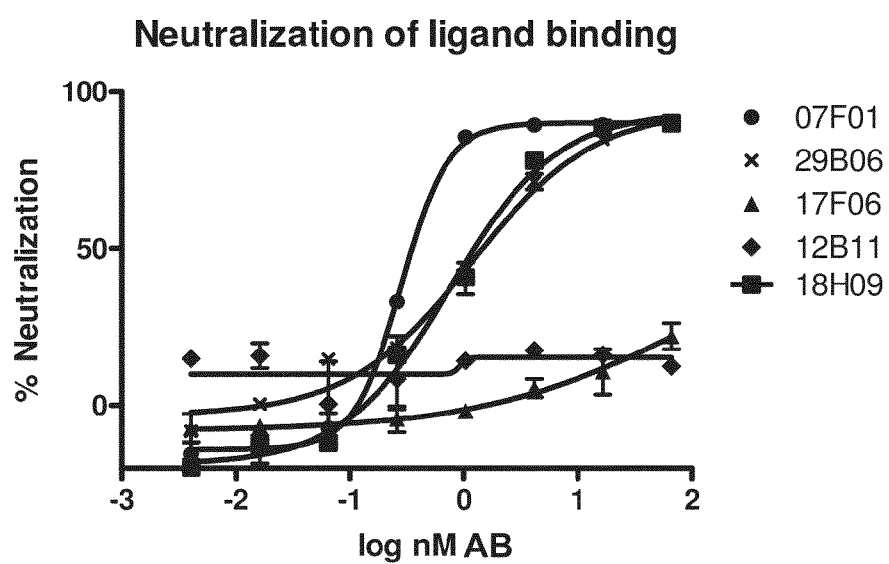
FIG. 6 is a graph showing dose-response curves for inhibition of the MSP-RON binding interaction by antibodies 17F06 (▲), 07F01 (●), 12B11 (♦), 18H09 (■), and 29B06 (x), as measured by electrochemiluminescence assay.

The MSP-hRON binding interaction was inhibited by antibodies 07F01, 18H06, and 29B06, but not by antibodies 17F06 and 12B11 (FIG. 6). The $IC_{50}$ and maximum percent inhibition values for the antibodies (IgG1) are shown in Table 10.

TABLE 10

| Antibody | $IC_{50}$ (nM) Average | Std Dev | Maximum Neutralization (%) Average | Std Dev | n |
|---|---|---|---|---|---|
| 07F01 | 0.26 | 0.05 | 88.3 | 2.1 | 3 |
| 18H09 | 0.91 | 0.15 | 86.9 | 6.7 | 3 |
| 29B06 | 1.11 | 0.06 | 87.6 | 4.7 | 3 |
| 12B11 | N/A | N/A | 44.8 | 20 | 3 |
| 17F06 | N/A | N/A | 7.9 | 11.2 | 2 |

The results in Table 10 demonstrate that antibodies 07F01, 18H09 and 29B06 block MSP binding to hRON SEMA+PSI, while antibodies 12B11 and 17F06 do not.

Example 9

Inhibition of Downstream Signaling by Anti-RON Antibodies

Antibodies 07F01, 12B11, 17F06, 18H09, and 29B06 were tested for inhibition of MSP-dependent phosphorylation of ERK, a RON downstream signaling molecule using the cell-based assay described in Example 3. The antibodies (concentration range: 0.006-10 μg/mL) in RPMI were added to the cells and incubated for one hour at 37° C.

Figure 7:
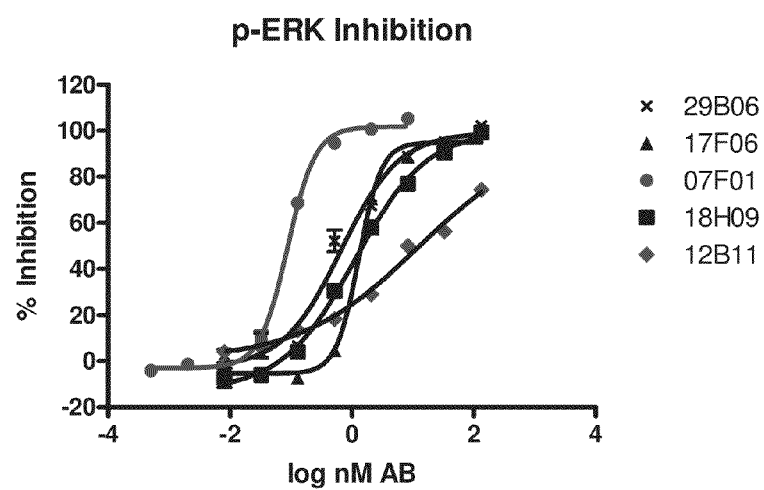
FIG. 7 is a graph showing dose-response curves for inhibition of MSP-dependent phosphorylation of ERK by antibodies 17F06 (▲), 07F01 (●), 12B11 (♦), 18H09 (■), and 29B06 (x) by ELISA assay.

Dose-dependent inhibition of ERK phosphorylation by antibodies 07F01, 12B11, 17F06, 18H09, and 29B06 is shown in Table 11 and FIG. 7.

TABLE 11

| Antibody | Mean IC50 (nM) | Std Dev | N |
|---|---|---|---|
| 07F01 | 0.07 | 0.02 | 3 |
| 18H09 | 0.71 | 0.36 | 3 |
| 29B06 | 0.44 | 0.27 | 3 |
| 12B11 | 5.91 | 5.92 | 3 |
| 17F06 | 0.96 | 0.4 | 3 |

The results in Table 11 and FIG. 7 demonstrate that antibodies 07F01, 18H09, 29B06, 12B11 and 17F06 inhibit MSP-induced ERK phosphorylation in T47D breast cancer cell line, even though 12B11 and 17F06 do not effectively block MSP binding to RON (see Examples 3 and 8).

Example 10

Inhibition of MSP-Dependent Cell Migration

Figure 8:
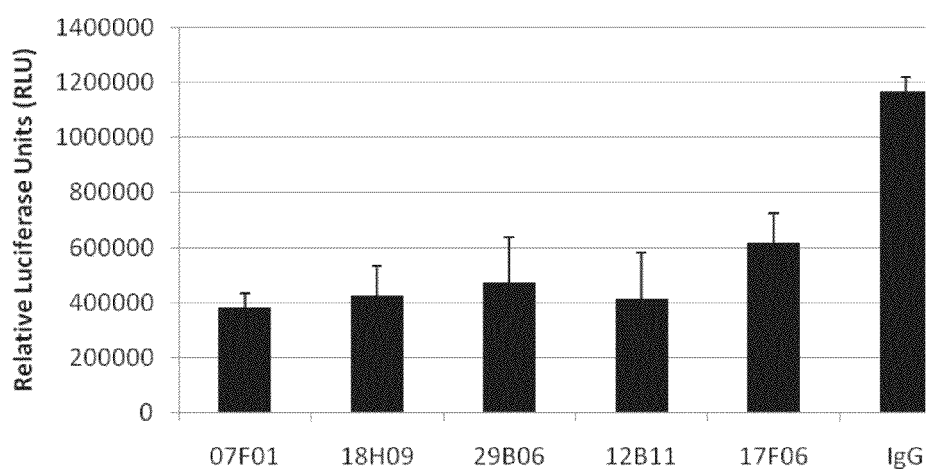
FIG. 8 is a histogram summarizing results from an experiment measuring inhibition of MSP induced HPAF-II cell migration by antibodies 07F01, 18H09, 29B06, 12B11, 17F06 and an IgG negative control (murine IgG) by transwell assay.

Antibodies 07F01, 18H09, 29B06, 12B11 and 17F06 were tested for inhibition of MSP-dependent cell migration. HPAF-II pancreatic cancer cells (ATCC) were incubated overnight under low serum conditions (1% FBS, MEM). Cells were trypsinized, counted, and placed at a concentration of 50,000/well in 45 µl of 1% FBS/MEM in the upper chamber of a BD 96-well FLUOROBLOK™ plate (Becton Dickinson). Antibodies were added at a concentration of 2 µg/ml, and cells were incubated for 2 hours. The bottom chamber contained 1% FBS MEM (200 µl) and 1 nM MSP, and cells were incubated for 24 hours. The number of migrated cells was determined by the addition of Calcien Dye at 4 µg/ml final concentration to the bottom chamber, followed by a one-hour incubation. Fluorescence intensity was measured using a WALLAC 1420 VICTOR™. Baseline fluorescent measurements were done in the absence of MSP. Percent inhibition was determined by comparing antibody-treated and antibody-untreated samples to the baseline using the following formula: 100-(anti-RON antibody treated-baseline)/(control huIgG treated-baseline)*100. Results on inhibition of MSP-induced HPAFII cell migration by antibodies 07F01, 18H09, 29B06, 12B11, and 17F06 are summarized in Table 12 and FIG. 8.

TABLE 12

| Antibody (2 µg/ml) | Percent Inhibition |
|---|---|
| 07F01 | 95.63 |
| 29B06 | 96.79 |
| 17F06 | 70.74 |
| 18H09 | 106.96 |
| 12B11 | 98.93 |

The results in Table 12 demonstrate that antibodies 07F01, 18H09, 29B06, 12B11 and 17F06 inhibit MSP-dependent cell migration in HPAF-II pancreatic cancer cell lines, even though 12B11 and 17F06 do not effectively block MSP binding to RON.

Example 11

Inhibition of Growth of Wild-Type RON-Dependent Tumor Model

Figure 9:
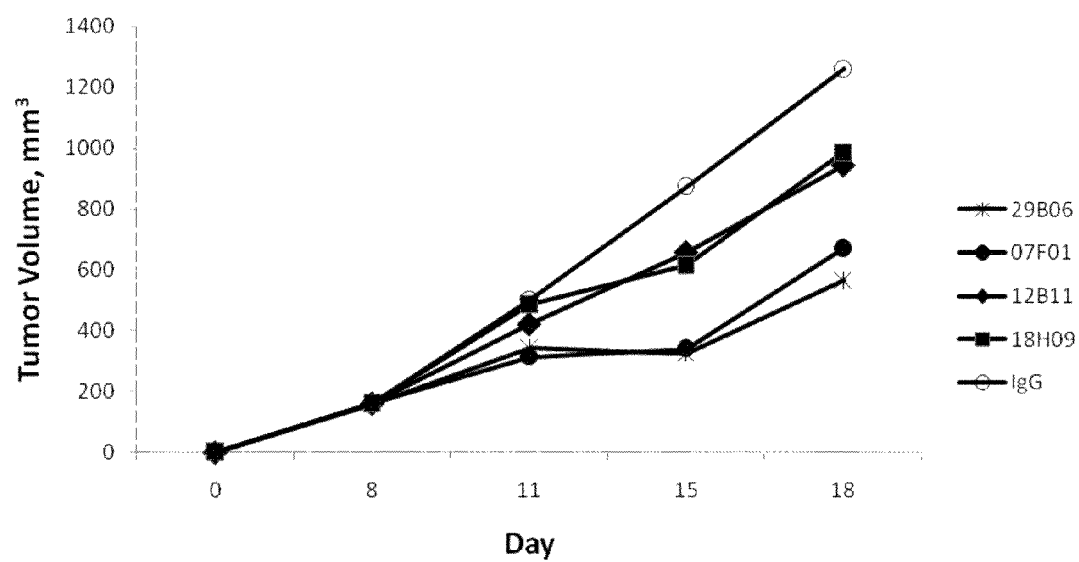
FIG. 9 is a graph summarizing data on inhibition of growth of a wild-type (wt) RON-dependent in vivo tumor model by antibodies 07F01 (●), 12B11 (♦), 18H09 (■), 29B06 (*), and a murine IgG control (○). The antibodies and IgG control were dosed at 20 mg/kg twice per week intraperitoneally.

Inhibition of tumor growth was tested in a directed complementation model of wild-type RON-driven tumor growth. "Directed complementation" tumors were obtained as described in Robinson et al., U.S. Pat. No. 7,556,796. A cDNA encoding wild-type human RON was introduced into BH3 tumor cells by retroviral transfer. Transfected tumor cells were then implanted subcutaneously into recipient mice. Growth of the BH3 tumors was dependent on expression of an inducible HER2 gene, which was not induced. Therefore, tumors would grow only if the RON gene functionally complemented the uninduced HER2 gene. Growth of the directed complementation tumors was observed. Primary tumors were propagated in vivo to generate sufficient tumor material for drug efficacy studies. Quality control for the directed complemented tumors included RT-PCR for RON expression and immunohistochemistry (IHC) for protein expression. The tumors were stored as frozen archival aliquots of approximately $1.5 \times 10^5$ cells/vial. These tumors were thawed, washed once, resuspended in HBS+matrigel and injected subcutaneously. Tumor measurements were taken twice weekly using vernier calipers. Tumor volume was calculated using the formula: width×width×length/2. When tumors reached approximately 150 mm$^3$, the mice were randomized into five groups of ten mice each. Each group (ten mice each) received one of the following antibody treatments: 07F01, 29B06, 12B11, or 18H09, or murine IgG control, all at 20 mg/kg. Treatment was administered by intra-peritoneal injection, twice weekly, for two weeks. Antibodies 29B06 and 07F01 resulted in tumor growth inhibition ("TGI") greater than 50% (p<0.001), while antibodies 18H09 and 12B11 exhibited TGI of 25% and 29%, respectively (FIG. 9). All treatments were well-tolerated with no significant loss in body weight.

Pharmacodynamic changes in RON receptor levels after 29B06 and 07F01 treatment were evaluated. Tumors were treated with 20 mg/kg of the following antibodies: mIgG (control), 29B06 or 07F01 and tumors were harvested at 24 or 48 hours. After harvest, the tumors were lysed in standard RIPA buffer (Boston Bioproducts, cat. No. BP-115) containing protease inhibitors (Roche, catalog No. 04693159001) and phosphatase inhibitors I and II (Sigma, cat. Nos. P2350 and P5726). Lysates were cleared and protein concentration was measured. A Western blot for total RON was done using a polyclonal anti-RON antibody (Santa Cruz, cat. No. sc-322). The Western blot analysis showed that antibody 29B06 induced receptor degradation in vivo in RON-DC xenograft at 24 hours, and to a greater extent at 48 hours.

Example 12

Inhibition of Growth of Delta 160 RON-Driven Tumor Model

Figure 10:
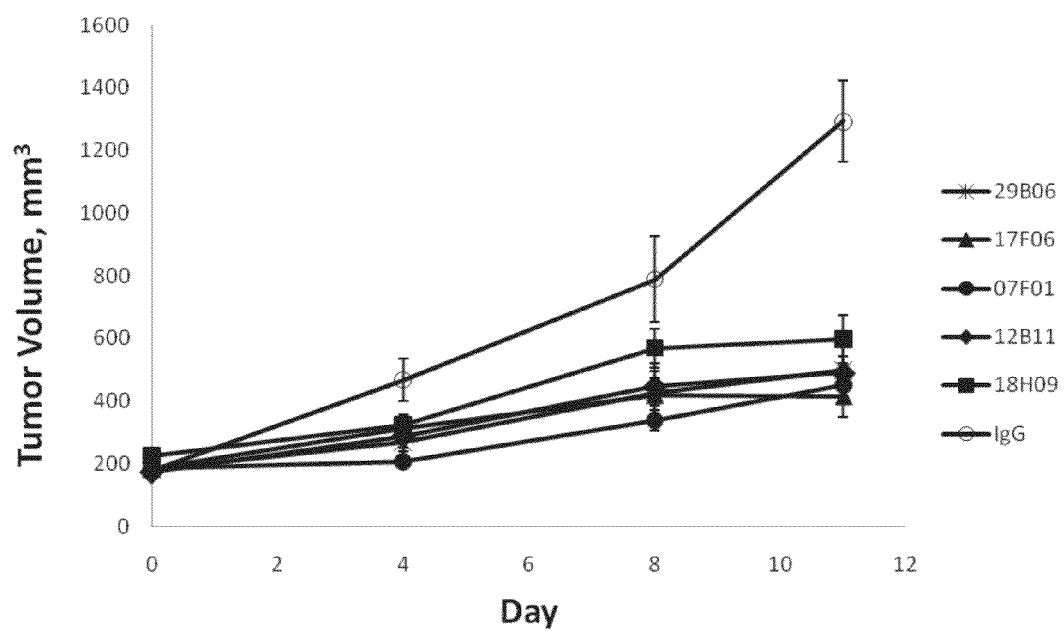
FIG. 10 is a graph summarizing data on inhibition of growth of a delta 160 RON-dependent in vivo tumor model by antibodies 17F06 (▲), 07F01 (●), 12B11 (♦), 18H09 (■), 29B06 (*), and a murine IgG control (○). The antibodies and IgG control were dosed at 20 mg/kg twice per week intraperitoneally.

Inhibition of tumor growth by the antibodies was tested in a directed complementation model of delta 160 RON-driven tumor growth. The model was obtained as described in Example 11, except that the transfected cDNA encoded human delta 160 (oncogenic) form of RON. Growth of the directed complementation tumors was observed. Primary tumors were propagated in vivo to generate sufficient tumor material for drug efficacy studies. Quality control for the directed complimented tumors included RT-PCR for RON expression and IHC for protein expression. The tumors were stored as frozen archival aliquots of approximately $1.5 \times 10^5$ cells/vial. These tumors were thawed, washed once, resuspended in HBS plus matrigel, and injected subcutaneously. Tumor measurements were taken twice weekly. When tumors reached approximately 150 mm$^3$, the mice were randomized into five groups of ten mice each. Each group (ten mice per group) received one of the following treatments: murine IgG control, 07F01, 29B06, 12B11, 17F06, and 18H09, all at 20 mg/kg. Treatment was administered by intra-peritoneal injection, twice weekly, for two weeks. Each treatment group showed similar tumor growth inhibition of greater than 60% (p<0.001) except for 18H09 (TGI 54%) as shown in FIG. 10. All treatments were well-tolerated, with no significant loss in body weight.

Example 13

Inhibition of Growth of NCI-H358 Lung Xenograft Tumor Model

Figure 11:
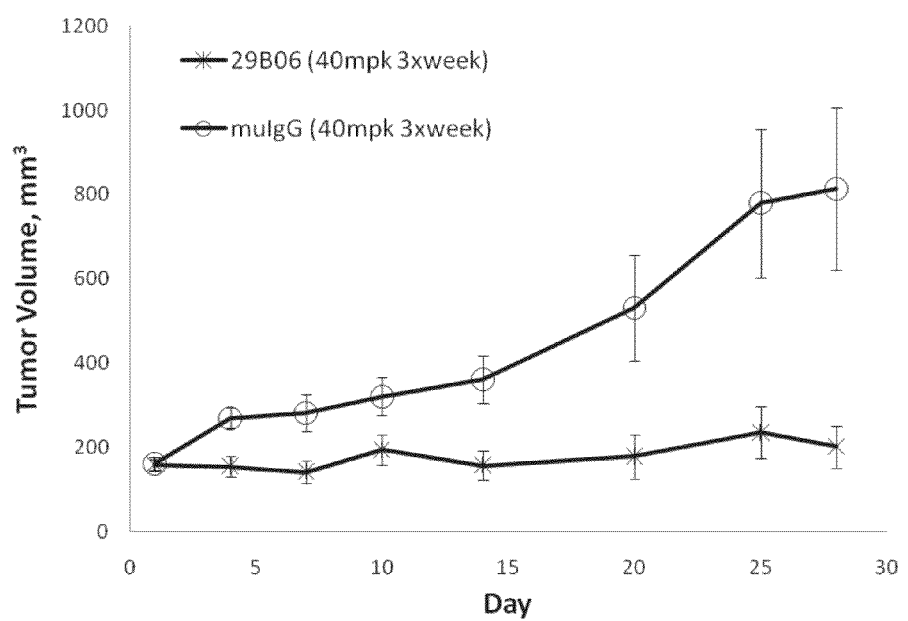
FIG. 11 is a graph summarizing data on inhibition of growth of an NCI-H358 xenograft tumor model by antibody 29B06 (*) and a murine IgG control (○). The antibody and IgG control were dosed at 40 mg/kg (abbreviated as "mpk") three per week intraperitoneally.

Inhibition of tumor growth by the 29B06 antibody was tested in an NCI-H358 lung xenograft model. The NCI-H358 cells were grown in culture at 37° C. in an atmosphere containing 5% $CO_2$, using RMPI medium (Invitrogen) containing 10% FBS. Cells were inoculated subcutaneously into the flank of 8-week old female CB.17 SCID mice with $5 \times 10^6$ cells per mouse in 50% matrigel. Tumor measurements were taken twice weekly. When tumors reached approximately 150 $mm^3$, the mice were randomized into two groups of ten mice each. Each group received one of the following treatments: murine IgG control or 29B06 at 40 mg/kg. Treatment was administered by intra-peritoneal injection three times per week, for three weeks. Antibody 29B06 treatment resulted in tumor growth inhibition of 70% ($p<0.001$) (FIG. 11). Treatment was well-tolerated, with no significant loss in body weight.

Example 14

Humanization of Anti-RON Antibodies

A. Construction of Humanized and Chimeric Anti-RON Antibodies

This Example describes the humanization of two murine antibodies, designated 07F01 and 29B06, and the characterization of the resulting humanized antibodies. The humanized anti-RON antibodies were designed using the SUPERHUMANIZATION™ method (Cephalon, Inc. (Arana Therapeutics Ltd.) and Hwang, W. Y. et al. (2005) METHODS 36:35-42), the CDR grafting method with back mutations (some human framework residues were changed to murine residues) (See e.g., U.S. Pat. Nos. 5,530,101; 5,693,761; 5,693,762; 5,585,089; 6,180,370; 7,022,500), or the HUMAN ENGINEERING™ method (Studnicka et al., Protein Eng. 1994 June; 7(6):805-14; also see, e.g., PCT Publication No. WO 93/11794 and U.S. Pat. Nos. 5,766,886; 5,770,196; 5,821,123; and 5,869,619). With the exception of heavy chain CDR1, the Kabat CDR definitions were used for CDR grafting onto human frameworks (SUPERHUMANIZATION™ and CDR grafting with back mutations). In some cases, a combination of Kabat and Chothia definitions were used for grafting heavy CDR1. In some cases, CDR residues (Kabat or Chothia definitions) were changed to human residues to increase humanness. Models of the murine antibodies were created using the SWISS-MODEL web server (swissmodel.expasy.org). Predicted residue contacts were determined using the Contact Map Analysis web server (ligin.weizmann.ac.il/cma/), and residue surface accessibility was determined using the Accessible Molecular Surface web server (swift.cmbi.ru.nl/servers/html/accessres.html). Residues were selected for back mutation based on predicted surface accessibility, contact with CDR residues, and involvement in the interface between heavy and light chains. Additionally, a cysteine residue present in the heavy chain CDR3 of 07F01 was changed to serine to prevent potential aggregation, and in some examples, a predicted N-linked glycosylation consensus site (N-X-S/T) in 07F01 heavy CDR2 (e.g., N58, Y59, T60) was mutated (e.g., T60A) to prevent any possible glycosylation. The designed amino acid sequences were converted to codon-optimized DNA sequences and synthesized by DNA2.0, Inc. to include (in the following order): 5' HindIII restriction site, Kozak consensus sequence, amino terminal signal sequence, humanized variable region, human IgG1 or Kappa constant region, stop codon, and a 3' EcoRI restriction site.

The anti-RON antibody chains humanized according to the SUPERHUMANIZATION™ method, as described herein, are designated with the prefix "Sh" before the antibody chain name. The anti-RON antibody chains humanized by the CDR grafting method with back mutations, as described herein, are designated with the prefix "Hu" before the antibody chain name. The anti-RON antibody chains humanized by the HUMAN ENGINEERING™ method, as described herein, are designated with the prefix "HE" before the antibody chain name.

The anti-RON antibody heavy chain 07F01 was humanized according to the SUPERHUMANIZATION™ method. Human germline sequence IGHV3-48*01 (also referred to herein as Hv3-48) was selected as the human heavy chain framework. In some embodiments, the human Hv3-48 heavy chain framework sequence was mutated at amino acid position 28 (e.g., D28T). Amino acid numbering is based on the Kabat numbering system.

The anti-RON antibody light chain 07F01 was humanized according to the HUMAN ENGINEERING™ method. Human germline sequence IGKV1-9*01 was selected as the human light chain framework.

The anti-RON antibody heavy chain 29B06 was humanized by the CDR grafting method with back mutations. Human germline sequence IGHV4-59*01 (also referred to herein as Hv4-59) was selected as the human framework. The human framework was back-mutated at amino acid positions 27, 30, 39, 44, 47, 48, 67, 71, and 78 to the murine sequence when the Kabat CDR definitions were used. The back-mutated human Hv4-59 framework sequence was further mutated to comprise at least one amino acid substitution at positions 27, 30, 48, 67, and 78. Amino acid substitutions in the back-mutated Hv4-59 framework sequence (e.g., amino acid substitution from a murine residue to a human residue, e.g., a human residue found in IGHV4-59) may be selected from the group consisting of D27G, T30S, M48I, I67V and Y78F. Amino acid numbering is based on the Kabat numbering system.

The anti-RON antibody light chain 29B06 was humanized according to the SUPERHUMANIZATION™ method. Human germline sequence IGKV2-28*01 was selected as the human light chain framework.

Chimeric (murine variable region and human constant region) 07F01 and 29B06 heavy (human IgG1) and light (human Kappa) chains were also constructed. The cysteine residue present in the heavy chain CDR3 of 07F01 was changed to serine to prevent potential aggregation. To generate chimeric antibodies, the murine variable regions were fused to the human constant region using overlap extension PCR, including (in the following order): 5' HindIII restriction site, Kozak consensus sequence, amino terminal signal sequence, mouse variable region, human IgG1 or Kappa constant region, stop codon, and 3' EcoRI restriction site.

The humanized and chimeric heavy chains were subcloned into pEE6.4 (Lonza, Basel, Switzerland) via HindIII and EcoRI sites using IN-FUSION™ PCR cloning (Clontech, Mountain View, Calif.). The humanized and chimeric Kappa light chains were subcloned into pEE14.4 (Lonza) via HindIII and EcoRI sites using IN-FUSION™ PCR cloning.

Humanized antibody chains or chimeric antibody chains were transiently transfected into 293T cells to produce antibody. Antibody was either purified or used in cell culture media supernatant for subsequent in vitro analysis. Binding of the chimeric and humanized antibodies to human RON was measured as described below. The results are summarized in Table 20.

Additionally, some humanized antibody heavy and light chain combinations were stably expressed in CHOK1SV cells using the GS SYSTEM™ (Lonza) in order to produce large quantities of purified humanized antibody. A single expression vector was constructed by combining pEE6.4 and pEE14.4 based vectors. First, pEE6.4 containing full length humanized heavy chain cDNA was digested with NotI and SalI to isolate the hCMV-MIE promoter+full length humanized heavy chain cDNA+SV40 poly A fragment. This fragment was inserted into the pEE14.4 vector already containing full length humanized light chain cDNA via NotI/SalI sites, thus creating an expression vector that simultaneously expresses heavy and light chains. The combined heavy and light chain vector was linearized and transfected into CHOK1SV cells. Stable clones were selected in the presence of methionine sulfoximine.

Each of the possible combinations of the humanized 07F01 immunoglobulin heavy chain and immunoglobulin light chain variable regions are set forth below in Table 13.

TABLE 13

| Light Chain Variable Region | Heavy Chain Variable Region |
|---|---|
| HE L 07F01 Kv1-9 Light Variable (SEQ ID NO: 139) | Sh07F01 Hv3-48 Heavy Variable (SEQ ID NO: 135) |
| HE L 07F01 Kv1-9 Light Variable (SEQ ID NO: 139) | Sh07F01 Hv3-48 D28T T60A L63V E65G Heavy Variable (SEQ ID NO: 137) |
| Sh07F01 Kv1-9 F1 Light Variable (SEQ ID NO: 141) | Sh07F01 Hv3-48 Heavy Variable (SEQ ID NO: 135) |
| Sh07F01 Kv1-9 F1 Light Variable (SEQ ID NO: 141) | Sh07F01 Hv3-48 D28T T60A L63V E65G Heavy Variable (SEQ ID NO: 137) |

Each of the possible combinations of the humanized 29B06 immunoglobulin heavy chain and immunoglobulin light chain variable regions are set forth below in Table 14.

TABLE 14

| Light Chain Variable Region | Heavy Chain Variable Region |
|---|---|
| Sh29B06 Kv2-28 Kappa Variable (SEQ ID NO: 149) | Sh29B06 Hv4-59 Heavy Variable (SEQ ID NO: 143) |
| Sh29B06_Kv2-28 Kappa Variable (SEQ ID NO: 149) | Hu29B06 Hv4-59 Heavy Variable (SEQ ID NO: 145) |
| Sh29B06 Kv2-28 Kappa Variable (SEQ ID NO: 149) | Hu29B06 Hv4-59 D27G T30S M48I I67V Y78F Heavy Variable (SEQ ID NO: 147) |

The nucleic acid sequences encoding and the protein sequences defining variable regions of the humanized 07F01 and 29B06 antibodies are summarized below (amino terminal signal peptide sequences are not shown). Sequences of the modified chimeric 07F01 heavy variable region in which the cysteine in CDR3 is changed to serine are also summarized below. CDR sequences (Kabat definition) are shown in bold and are underlined in the amino acid sequences.

```
Nucleic Acid Sequence Encoding the Chimeric 07F01 C102S Heavy Chain Variable
Region
                                                              (SEQ ID NO: 132)
     1  gaggtgaagc ttctcgagtc tggaggtggc ctggtgcagc cgggtggatc cctgaaactc 61  tcctgtgcag cctcaggatt cgattttagt agacactgga tgagttgggt ccggctggct 121  ccagggaaag gctagaatg gatcgcagaa attaatccag atagcagaac gataaactat 181  acgccatctc taaaggagaa attcatcatc tccagagaca cgccaaaaa ttcgctgttt 241  ctgcaaatga acagagtgag atctgaggac acagcccttt attactgtgc aagacgggta 301  agaattcatt actacggcgc tatggacagc tggggtcaag aacctcagt caccgtctcc 361  tca Protein Sequence Defining the Chimeric 07F01 C102S Heavy Chain Variable Region
                                                              (SEQ ID NO: 133)
     1  evkllesggg lvqpggslkl scaasgfdfs rhwmswvrla pgkglewiae inpdsrtiny 61  tpslkekfii srdnaknslf lqmnrvrsed talyycarrv rihyygamds wgqgtsvtvs 121  s Nucleic Acid Sequence Encoding the Sh07F01 Hv3-48 Heavy Chain Variable Region
                                                              (SEQ ID NO: 134)
     1  gaggttcagc tggtagaatc cggaggaggg ttggtccaac ctggtggatc actcagactt 61  tcatgcgccg ccagcggctt tgacttctca cgacattgga tgagctgggt ccggcaggct 121  ccaggcaagg gcctcgagtg ggttagcgag atcaatccag acagcagaac cattaactat 181  acacccagtc tgaaggagcg gttcaccata agccgtgata tgccaagaa ctccctgtac 241  ttgcagatga actccttgcg cgctgaagat acagctgtgt actattgtgc aaggcgcgtg 301  cgaatccact attacggggc aatggattct tggggccagg gtactaccgt gactgtgagt 361  tct
```

-continued

Protein Sequence Defining the Sh07F01 Hv3-48 Heavy Chain Variable Region
(SEQ ID NO: 135)

```
  1  evqlvesggg lvqpggslrl scaasgfdfs rhwmswvrga pgkglewvse inpdsrtiny 61  tpslkerfti srdnaknsly lqmnslraed tavyycarrv rihyygamds wgqgttvtvs 121  s
```

Nucleic Acid Sequence Encoding the Sh07F01 Hv3-48 D28T T60A L63V E65G Heavy Chain Variable Region
(SEQ ID NO: 136)

```
  1  gaggttcagc tggtagaatc cggaggaggg ttggtccaac ctggtggatc actcagactt 61  tcatgcgccg ccagcggctt taccttctca cgacattgga tgagctgggt ccggcaggct 121  ccaggcaagg gcctcgagtg ggttagcgag atcaatccag acagcagaac cattaactat 181  gcccccagtg tgaagggccg gttcaccata agccgtgata atgccaagaa ctccctgtac 241  ttgcagatga actccttgcg cgctgaagat acagctgtgt actattgtgc aaggcgcgtg 301  cgaatccact attacggggc aatggattct gggggccagg gtactaccgt gactgtgagt 361  tct
```

Protein Sequence Defining the Sh07F01 Hv3-48 D28T T60A L63V E65G Heavy Chain Variable Region
(SEQ ID NO: 137)

```
  1  evqlvesggg lvqpggslrl scaasgftfs rhwmswvrqa pgkglewvse inpdsrtiny 61  apsvkgrfti srdnaknsly lqmnslraed tavyycarrv rihyygamds wgqgttvtvs 121  s
```

Nucleic Acid Sequence Encoding the HE_L 07F01_Kv1-9 Kappa Chain Variable Region
(SEQ ID NO: 138)

```
  1  gatatccagt tgactcagtc tcagtccttt gtgagtacat cagtgggcga cagggtcacc 61  gtgacctgcc gagcatcaca gaacgttgga agctctcttg tctggtatca gcaaagcct 121  gggaagagcc ccaaaaccct catctattct gcttcctttc tgtactccgg cgtaccaagt 181  agattctctg gtagcggatc cgggacagag ttcactctca caattagcag tgtgcagcct 241  gaggatttcg ccgactactt ctgtcagcaa tacaataact atccccctgac ttttggtggc 301  ggcaccaaag tggaaatcaa g
```

Protein Sequence Defining the HE L 07F01 Kv1-9 Kappa Chain Variable Region
(SEQ ID NO: 139)

```
  1  diqltqsqsf vstsvgdrvt vtcrasqnvg sslvwyqqkp gkspktliys asflysgvps 61  rfsgsgsgte ftltissvqp edfadyfcgg ynnypltfgg gtkveik
```

Nucleic Acid Sequence Encoding the sh07F01 Kv1-9 F1 Kappa Chain Variable Region
(SEQ ID NO: 140)

```
  1  gacattcagc tgactcagtc gccgtcgttt ttgtcggcgt ccgtgggtga cagagtgact 61  atcacatgtc gcgcttcgca aaacgtcgga tcatcgcttg tgtggtatca gcagaaaccc 121  ggtaaagccc ctaagaccct catctattca gcgtcatttc tgtatagcgg ggtcccctca 181  cggttcagcg gatccggctc cgggaccgag ttcacactca ctatttcgag cttgcagccg 241  gaagattttg caacgtacta ctgccagcaa tacaataact acccactcac gttcggaggg 301  ggaacgaagg tagagatcaa g
```

Protein Sequence Defining the sh07F01 Kv1-9 F1 Kappa Chain Variable Region
(SEQ ID NO: 141)

```
  1  diqltqspsf lsasvgdrvt itcrasqnvg sslvwyqqkp gkapktliys asflysgvps 61  rfsgsgsgte ftltisslqp edfatyycgg ynnypltfgg gtkveik
```

Nucleic Acid Sequence Encoding the Sh29B06_Hv4-59 Heavy Chain Variable Region
(SEQ ID NO: 142)

```
  1  caagttcagc tgcaagaatc cggaccagga ttggtcaaac cttcagagac actcagcctg
```

```
 61 acttgcaccg tgagcggtgg cagcatatcc tccggttatt ggaactggat ccggcagcca 121 ccaggcaagg cctcgagtg gattggctac atcagctata gcgggaaaac ctattacaac 181 cccagtctga agagccgagt gaccataagc gtcgatacaa gtaagaacca gttctccctg 241 aagctctcat ccgtgaccgc cgctgataca gctgtgtact attgtgcaag gtcaaagtat 301 gactacgcaa tggactattg gggccagggt actctggtga ctgtgagttc t
```

Protein Sequence Defining the Sh29B06 Hv4-59 Heavy Chain Variable Region
(SEQ ID NO: 143)

```
  1 qvqlqesgpg lvkpsetlsl tctvsggsis sgvwnwirqp pgkglewigy isysgktyyn 61 pslksrvtis vdtsknqfsl klssvtaadt avyycarsky dyamdywgqg tlvtvss
```

Nucleic Acid Sequence Encoding the Hu29B06_Hv4-59 Heavy Chain Variable Region
(SEQ ID NO: 144)

```
  1 caagttcagc tgcaagaatc cggaccagga ttggtcaaac ccagcgaaac actctctctt 61 acatgcaccg tgagcggcga ctctatcacc tcagggtatt ggaattggat tcggaaaccc 121 ccaggcaaga agctcgagta catgggttac atcagttaca gcgggaaaac ctactataac 181 cccagtctga agagcagaat caccataagc cgtgatacct ctaagaacca gtactccctg 241 aagctgagtt ccgtaacagc agctgataca gctgtgtact attgtgcaag gagtaagtat 301 gactacgcaa tggactattg gggccagggt actcttgtga ctgtgagttc t
```

Protein Sequence Defining the Hu29B06_Hv4-59 Heavy Chain Variable Region
(SEQ ID NO: 145)

```
  1 qvqlqesgpg lvkpsetlsl tctvsgdsit sgvwnwirkp pgkkleymgy isysgktyyn 61 pslksritis rdtsknqysl klssvtaadt avyycarsky dyamdywgqg tlvtvss
```

Nucleic Acid Sequence Encoding the Hu29B06 D27G T30S M48I I67V Y78F Heavy Chain Variable Region
(SEQ ID NO: 146)

```
  1 caagttcagc tgcaagaatc cggaccagga ttggtcaaac cttcagagac actcagcctg 61 acttgcaccg tgagcggtgg cagcatatcc tccggttatt ggaactggat ccggaagcca 121 ccaggcaaga agctcgagta cattggctac atcagctata gcgggaaaac ctattacaac 181 cccagtctga agagccgagt gaccataagc agggatacaa gtaagaacca gttctccctg 241 aagctctcat ccgtgaccgc cgctgataca gctgtgtact attgtgcaag gtcaaagtat 301 gactacgcaa tggactattg gggccagggt actctggtga ctgtgagttc t
```

Protein Sequence Defining the Hu29B06 D27G T30S M48I I67V Y78F Heavy Chain Variable Region
(SEQ ID NO: 147)

```
  1 qvqlqesgpg lvkpsetlsl tctvsggsis sgvwnwirkp pgkkleyigy isysgktyyn 61 pslksrvtis rdtsknqfsl klssvtaadt avyycarsky dyamdywgqg tlvtvss
```

Nucleic Acid Sequence Encoding the Sh29B06 Kv2-28 Kappa Chain Variable Region
(SEQ ID NO: 148)

```
  1 gatatcgtta tgacccagag cccacttagt ttgcctgtta ctcctggcga gcctgccagt 61 atttcttgcc gtgctagcga aatcgtggat aactttggta tatcattcat gaattggtat 121 ctccaaaaac ctggccaaag cccccagctc cttatctacg ccgctagcaa ccaggggtcc 181 ggggtacctg atagattttc aggcagcggc tctggaaccg acttcacact gaagatttcc 241 cgggtggagg ccgaggacgt gggcgtgtac tattgtcaac agtccaagga agtccctccc 301 acttcggcg gtgggacaaa ggttgagatt aag
```

Protein Sequence Defining the Sh29B06 Kv2-28 Kappa Chain Variable Region
(SEQ ID NO: 149)

```
  1 divmtqspls lpvtpgepas iscraseivd nfgisfmnwy lqkpgqspql liyaasnqgs 61 gvpdrfsgsg sgtdftlkis rveaedvgvy ycqqskevpp tfggtkvei k
```

The amino acid sequences defining the immunoglobulin heavy chain variable regions for the antibodies produced in Example 14 are aligned in FIGS. 12A and 12B. Amino terminal signal peptide sequences (for proper expression/secretion) are not shown. $CDR_1$, $CDR_2$, and $CDR_3$ (Kabat definition) are identified by boxes. FIGS. 13A and 13B show an alignment of the separate $CDR_1$, $CDR_2$, and $CDR_3$ sequences for each of the variable region sequences shown in FIGS. 12A and 12B, respectively.

The amino acid sequences defining the immunoglobulin light chain variable regions for the antibodies in Example 14 are aligned in FIGS. 14A and 14B. Amino terminal signal peptide sequences (for proper expression/secretion) are not shown. $CDR_1$, $CDR_2$ and $CDR_3$ are identified by boxes. FIGS. 15A and 15B show an alignment of the separate $CDR_1$, $CDR_2$, and $CDR_3$ sequences for each of the variable region sequences shown in FIGS. 14A and 14B, respectively.

Table 15 is a concordance chart showing the SEQ ID NO. of each sequence discussed in this Example.

TABLE 15

| SEQ. ID NO. | Nucleic Acid or Protein |
|---|---|
| 132 | Chimeric 07F01 C102S Heavy Chain Variable Region-nucleic acid |
| 133 | Chimeric 07F01 C102S Heavy Chain Variable Region-protein |
| 5 | Chimeric 07F01 C102S Heavy Chain $CDR_1$ |
| 6 | Chimeric 07F01 C102S Heavy Chain $CDR_2$ |
| 123 | Chimeric 07F01 C102S Heavy Chain $CDR_3$ |
| 134 | Sh07F01 Hv3-48 Heavy Chain Variable Region-nucleic acid |
| 135 | Sh07F01 Hv3-48 Heavy Chain Variable Region-protein |
| 5 | Sh07F01 Hv3-48 Heavy Chain $CDR_1$ |
| 6 | Sh07F01 Hv3-48 Heavy Chain $CDR_2$ |
| 123 | Sh07F01 Hv3-48 Heavy Chain $CDR_3$ |
| 136 | Sh07F01 Hv3-48 D28T T60A L63V E65G Heavy Chain Variable Region-nucleic acid |
| 137 | Sh07F01 Hv3-48 D28T T60A L63V E65G Heavy Chain Variable Region-protein |
| 5 | Sh07F01 Hv3-48 D28T T60A L63V E65G Heavy Chain $CDR_1$ |
| 122 | Sh07F01 Hv3-48 D28T T60A L63V E65G Heavy Chain $CDR_2$ |
| 123 | Sh07F01 Hv3-48 D28T T60A L63V E65G Heavy Chain $CDR_3$ |

TABLE 15-continued

| SEQ. ID NO. | Nucleic Acid or Protein |
|---|---|
| 138 | HE L 07F01 Kv1-9 Light (kappa) Chain Variable Region-nucleic acid |
| 139 | HE L 07F01 Kv1-9 Light (kappa) Chain Variable Region-protein |
| 130 | HE L 07F01 Kv1-9 Light (kappa) Chain $CDR_1$ |
| 131 | HE L 07F01 Kv1-9 Light (kappa) Chain $CDR_2$ |
| 10 | HE L 07F01 Kv1-9 Light (kappa) Chain $CDR_3$ |
| 140 | Sh07F01 Kv1-9 F1 Light (kappa) Chain Variable Region-nucleic acid |
| 141 | Sh07F01 Kv1-9 F1 Light (kappa) Chain Variable Region-protein |
| 130 | Sh07F01 Kv1-9 F1 Light (kappa) Chain $CDR_1$ |
| 131 | Sh07F01 Kv1-9 F1 Light (kappa) Chain $CDR_2$ |
| 10 | Sh07F01 Kv1-9 F1 Light (kappa) Chain $CDR_3$ |
| 142 | Sh29B06 Hv4-59 Heavy Chain Variable Region-nucleic acid |
| 143 | Sh29B06 Hv4-59 Heavy Chain Variable Region-protein |
| 45 | Sh29B06 Hv4-59 Heavy Chain $CDR_1$ |
| 46 | Sh29B06 Hv4-59 Heavy Chain $CDR_2$ |
| 47 | Sh29B06 Hv4-59 Heavy Chain $CDR_3$ |
| 144 | Hu29B06 Hv4-59 Heavy Chain Variable Region-nucleic acid |
| 145 | Hu29B06 Hv4-59 Heavy Chain Variable Region-protein |
| 45 | Hu29B06 Hv4-59 Heavy Chain $CDR_1$ |
| 46 | Hu29B06 Hv4-59 Heavy Chain $CDR_2$ |
| 47 | Hu29B06 Hv4-59 Heavy Chain $CDR_3$ |
| 146 | Hu29B06 Hv4-59 D27G T30S M48I I67V Y78F Heavy Chain Variable Region-nucleic acid |
| 147 | Hu29B06 Hv4-59 D27G T30S M48I I67V Y78F Heavy Chain Variable Region-protein |
| 45 | Hu29B06 Hv4-59 D27G T30S M48I I67V Y78F Heavy Chain $CDR_1$ |
| 46 | Hu29B06 Hv4-59 D27G T30S M48I I67V Y78F Heavy Chain $CDR_2$ |
| 47 | Hu29B06 Hv4-59 D27G T30S M48I I67V Y78F Heavy Chain $CDR_3$ |
| 148 | Sh29B06 Kv2-28 Light (kappa) Chain Variable Region-nucleic acid |
| 149 | Sh29B06 Kv2-28 Light (kappa) Chain Variable Region-protein |
| 48 | Sh29B06 Kv2-28 Light (kappa) Chain $CDR_1$ |
| 49 | Sh29B06 Kv2-28 Light (kappa) Chain $CDR_2$ |
| 50 | Sh29B06 Kv2-28 Light (kappa) Chain $CDR_3$ |

Humanized monoclonal antibody heavy chain CDR sequences (Kabat, Chothia, and IMGT definitions) are shown in Table 16.

TABLE 16

| | CDR1 | CDR2 | CDR3 |
|---|---|---|---|
| Kabat | | | |
| 07F01 | RHWMS (SEQ ID NO: 5) | EINPDSRTINYTPSLKE (SEQ ID NO: 6) | RVRIHYYGAMDC (SEQ ID NO: 7) |
| Chimeric 07F01 C102S | RHWMS (SEQ ID NO: 5) | EINPDSRTINYTPSLKE (SEQ ID NO: 6) | RVRIHYYGAMDS (SEQ ID NO: 123) |
| Sh07F01 Hv3-48 | RHWMS (SEQ ID NO: 5) | EINPDSRTINYTPSLKE (SEQ ID NO: 6) | RVRIHYYGAMDS (SEQ ID NO: 123) |
| Sh07F01 Hv3-48 D28T T60A L63V E65G | RHWMS (SEQ ID NO: 5) | EINPDSRTINYAPSVKG (SEQ ID NO: 122) | RVRIHYYGAMDS (SEQ ID NO: 123) |
| 29B06 | SGYWN (SEQ ID NO: 45) | YISYSGKTYYNPSLKS (SEQ ID NO: 46) | SKYDYAMDY (SEQ ID NO: 47) |
| Sh29B06 Hv4-59 | SGYWN (SEQ ID NO: 45) | YISYSGKTYYNPSLKS (SEQ ID NO: 46) | SKYDYAMDY (SEQ ID NO: 47) |
| Hu29B06 Hv4-59 | SGYWN (SEQ ID NO: 45) | YISYSGKTYYNPSLKS (SEQ ID NO: 46) | SKYDYAMDY (SEQ ID NO: 47) |

TABLE 16-continued

|  | CDR1 | CDR2 | CDR3 |
|---|---|---|---|
| Hu29B06 Hv4-59 D27G T30S M48I I67V Y78F | SGYWN (SEQ ID NO: 45) | YISYSGKTYYNPSLKS (SEQ ID NO: 46) | SKYDYAMDY (SEQ ID NO: 47) |
| Chothia | | | |
| 07F01 | GFDFSRH (SEQ ID NO: 51) | NPDSRT (SEQ ID NO: 52) | RVRIHYYGAMDC (SEQ ID NO: 7) |
| Chimeric 07F01 C102S | GFDFSRH (SEQ ID NO: 51) | NPDSRT (SEQ ID NO: 52) | RVRIHYYGAMDS (SEQ ID NO: 125) |
| Sh07F01 Hv3-48 | GFDFSRH (SEQ ID NO: 51) | NPDSRT (SEQ ID NO: 52) | RVRIHYYGAMDS (SEQ ID NO: 125) |
| Sh07F01 Hv3-48 D28T T60A L63V E65G | GFTFSRH (SEQ ID NO: 124) | NPDSRT (SEQ ID NO: 52) | RVRIHYYGAMDS (SEQ ID NO: 125) |
| 29B06 | GDSITSG (SEQ ID NO: 59) | SYSGK (SEQ ID NO: 60) | SKYDYAMDY (SEQ ID NO: 47) |
| Sh29B06 Hv4-59 | GGSISSG (SEQ ID NO: 126) | SYSGK (SEQ ID NO: 60) | SKYDYAMDY (SEQ ID NO: 47) |
| Hu29B06 Hv4-59 | GDSITSG (SEQ ID NO: 59) | SYSGK (SEQ ID NO: 60) | SKYDYAMDY (SEQ ID NO: 47) |
| Hu29B06 Hv4-59 D27G T30S M48I I67V Y78F | GGSISSG (SEQ ID NO: 126) | SYSGK (SEQ ID NO: 60) | SKYDYAMDY (SEQ ID NO: 47) |
| IMGT | | | |
| 07F01 | GFDFSRHW (SEQ ID NO: 61) | INPDSRTI (SEQ ID NO: 62) | ARRVRIHYYGAMDC (SEQ ID NO: 63) |
| Chimeric 07F01 C102S | GFDFSRHW (SEQ ID NO: 61) | INPDSRTI (SEQ ID NO: 62) | ARRVRIHYYGAMDS (SEQ ID NO: 128) |
| Sh07F01 Hv3-48 | GFDFSRHW (SEQ ID NO: 61) | INPDSRTI (SEQ ID NO: 62) | ARRVRIHYYGAMDS (SEQ ID NO: 128) |
| Sh07F01 Hv3-48 D28T T60A L63V E65G | GFTFSRHW (SEQ ID NO: 127) | INPDSRTI (SEQ ID NO: 62) | ARRVRIHYYGAMDS (SEQ ID NO: 128) |
| 29B06 | GDSITSGY (SEQ ID NO: 73) | ISYSGKT (SEQ ID NO: 74) | ARSKYDYAMDY (SEQ ID NO: 75) |
| Sh29B06 Hv4-59 | GGSISSGY (SEQ ID NO: 129) | ISYSGKT (SEQ ID NO: 74) | ARSKYDYAMDY (SEQ ID NO: 75) |
| Hu29B06 Hv4-59 | GDSITSGY (SEQ ID NO: 73) | ISYSGKT (SEQ ID NO: 74) | ARSKYDYAMDY (SEQ ID NO: 75) |
| Hu29B06 Hv4-59 D27G T30S M48I I67V Y78F | GGSISSGY (SEQ ID NO: 129) | ISYSGKT (SEQ ID NO: 74) | ARSKYDYAMDY (SEQ ID NO: 75) |

Humanized monoclonal antibody Kappa light chain CDR sequences (Kabat, Chothia, and IMGT definitions) are shown in Table 17.

TABLE 17

|  | CDR1 | CDR2 | CDR3 |
|---|---|---|---|
| Kabat/Chothia | | | |
| 07F01 | KASQNVGSSLV (SEQ ID NO: 8) | SASFRYS (SEQ ID NO: 9) | QQYNNYPLT (SEQ ID NO: 10) |

TABLE 17-continued

|  | CDR1 | CDR2 | CDR3 |
|---|---|---|---|
| HE L 07F01 Kv1-9 | RASQNVGSSLV (SEQ ID NO: 130) | SASFLYS (SEQ ID NO: 131) | QQYNNYPLT (SEQ ID NO: 10) |
| Sh07F01 Kv1-9 F1 | RASQNVGSSLV (SEQ ID NO: 130) | SASFLYS (SEQ ID NO: 131) | QQYNNYPLT (SEQ ID NO: 10) |
| 29B06 | RASEIVDNFGISFMN (SEQ ID NO: 48) | AASNQGS (SEQ ID NO: 49) | QQSKEVPPT (SEQ ID NO: 50) |
| Sh29B06 Kv2-28 | RASEIVDNFGISFMN (SEQ ID NO: 48) | AASNQGS (SEQ ID NO: 49) | QQSKEVPPT (SEQ ID NO: 50) |

| | IMG | | |
|---|---|---|---|
| 07F01 | QNVGSS (SEQ ID NO: 76) | SAS | QQYNNYPLT (SEQ ID NO: 10) |
| HE L 07F01 Kv1-9 | QNVGSS (SEQ ID NO: 76) | SAS | QQYNNYPLT (SEQ ID NO: 10) |
| Sh07F01 Kv1-9 F1 | QNVGSS (SEQ ID NO: 76) | SAS | QQYNNYPLT (SEQ ID NO: 10) |
| 29B06 | EIVDNFGISF (SEQ ID NO: 81) | AAS | QQSKEVPPT (SEQ ID NO: 50) |
| Sh29B06 Kv2-28 | EIVDNFGISF (SEQ ID NO: 81) | AAS | QQSKEVPPT (SEQ ID NO: 50) |

To create the complete chimeric and humanized heavy or kappa chain antibody sequences, each variable sequence above is combined with its respective human constant region. For example, a complete heavy chain comprises a heavy variable sequence followed by a human IgG1 heavy chain constant sequence. A complete kappa chain comprises a kappa variable sequence followed by the human kappa light chain constant sequence.

```
Nucleic Acid Sequence Encoding the Human IgG1 Heavy Chain Constant Region
                                                      (SEQ ID NO: 150)
  1  gcctcaacaa aaggaccaag tgtgttccca ctcgccccta gcagcaagag tacatccggg 61  ggcactgcag cactcggctg cctcgtcaag gattattttc cagagccagt aaccgtgagc 121  tggaacagtg gagcactcac ttctggtgtc catactttc  ctgctgtcct gcaaagctct 181  ggcctgtact cactcagctc cgtcgtgacc gtgccatctt catctctggg cactcagacc 241  tacatctgta atgtaaacca caagcctagc aatactaagg tcgataagcg ggtggaaccc 301  aagagctgcg acaagactca cacttgtccc ccatgccctg cccctgaact tctgggcggt 361  cccagcgtct ttttgttccc accaaagcct aaagatactc tgatgataag tagaacaccc 421  gaggtgacat gtgttgttgt agacgtttcc cacgaggacc cagaggttaa gttcaactgg 481  tacgttgatg gagtcgaagt acataatgct aagaccaagc tagagagga gcagtataat 541  agtacatacc gtgtagtcag tgttctcaca gtgctgcacc aagactggct caacggcaaa 601  gaatacaaat gcaaagtgtc caacaaagca ctcccagccc ctatcgagaa gactattagt 661  aaggcaaagg ggcagcctcg tgaaccacag gtgtacactc tgccacccag tagagaggaa 721  atgacaaaga accaagtctc attgacctgc ctggtgaaag gcttctaccc cagcgacatc 781  gccgttgagt gggagagtaa cggtcagcct gagaacaatt acaagacaac cccccagtg 841  ctggatagtg acgggtcttt cttctgtac  agtaagctga ctgtggacaa gtcccgctgg 901  cagcagggta acgtcttcag ctgttccgtg atgcacgagg cattgcacaa ccactacacc 961  cagaagtcac tgagcctgag cccagggaag
```

Protein Sequence Defining the Human IgG1 Heavy Chain Constant Region
(SEQ ID NO: 151)

```
  1  astkgpsvfp lapsskstsg gtaalgclvk dyfpepvtvs wnsgaltsgv htfpavlqss 61  glyslssvvt vpssslgtqt yicnvnhkps ntkvdkrvep kscdkthtcp pcpapellgg 121  psvflfppkp kdtlmisrtp evtcvvvdvs hedpevkfnw yvdgvevhna ktkpreeqyn 181  styrvvsvlt vlhqdwlngk eykckvsnka lpapiektis kakgqprepq vytlppsree 241  mtknqvsltc lvkgfypsdi avewesngqp ennykttppv ldsdgsffly skltvdksrw 301  qqgnvfscsv mhealhnhyt qkslslspgk
```

Nucleic Acid Sequence Encoding the Human Kappa Light Chain Constant Region
(used for chimeric antibodies)
(SEQ ID NO: 152)

```
  1  cgcacagtcg ccgctccctc cgtgttcatc tttccaccaa gtgatgagca actgaagtct 61  ggtactgctt cagtcgtgtg tctgctgaac aatttctacc ctcgagaagc caaagtccaa 121  tggaaggtag acaacgcact gcagtccggc aatagccaag aatcagttac cgaacaggat 181  tcaaaggaca gtacatattc cctgagcagc actctgaccc tgtcaaaggc cgattacgag 241  aaacacaagg tctatgcttg cgaagtgaca catcaggac tgtccagccc agtgacaaaa 301  tcttttaacc gtggggagtg t
```

Nucleic Acid Sequence Encoding the Human Kappa Light Chain Constant Region
(used for humanized antibodies)
(SEQ ID NO: 153)

```
  1  cgcacagttg ctgcccccag cgtgttcatt tcccaccta gcgatgagca gctgaaaagc 61  ggtactgcct ctgtcgtatg cttgctcaac aactttacc cacgtgaggc taaggtgcag 121  tggaaagtgg ataatgcact tcaatctgga aacagtcaag agtccgtgac agaacaggac 181  agcaaagact caacttattc actctcttcc accctgactc tgtccaaggc agactatgaa 241  aaacacaagg tatacgcctg cgaggttaca caccagggtt tgtctagtcc tgtcaccaag 301  tccttcaata ggggcgaatg t
```

Protein Sequence Defining the Human Kappa Light Chain Constant Region (used for
chimeric and humanized antibodies)
(SEQ ID NO: 154)

```
  1  rtvaapsvfi fppsdeqlks gtasvvclln nfypreakvq wkvdnalqsg nsqesvteqd 61  skdstyslss tltlskadye khkvyacevt hqglsspvtk sfnrgec
```

The following sequences represent the actual or contemplated full length heavy and light chain sequence (i.e., containing both the variable and constant regions sequences) for each antibody described in this Example. Signal sequences for proper secretion of the antibodies (e.g., signal sequences at the 5' end of the DNA sequences or the amino terminal end of the protein sequences) are not shown in the full length heavy and light chain sequences disclosed herein and are not included in the final secreted protein. Also not shown are stop codons for termination of translation required at the 3' end of the DNA sequences. It is within ordinary skill in the art to select a signal sequence and/or a stop codon for expression of the disclosed full length IgG heavy chain and light chain sequences. It is also contemplated that the variable region sequences can be ligated to other constant region sequences to produce active full length IgG heavy and light chains.

Nucleic Acid Sequence Encoding the Full Length Chimeric 07F01 C102S Heavy
Chain (Mouse Heavy Chain Variable Region and Human IgG1 Constant Region)
(SEQ ID NO: 155)

```
  1  gaggtgaagc ttctcgagtc tggaggtggc ctggtgcagc cgggtggatc cctgaaactc 61  tcctgtgcag cctcaggatt cgattttagt agacactgga tgagttgggt ccggctggct 121  ccagggaaag gctagaatg gatcgcagaa attaatccag atagcagaac gataaactat 181  acgccatctc taaggagaa attcatcatc tccagadaca cgccaaaaa ttcgctgttt 241  ctgcaaatga acagagtgag atctgaggac acagcccttt attactgtgc aagacgggta 301  agaattcatt actacggcgc tatggacagc tggggtcaag gaacctcagt caccgtctcc 361  tcagcctcaa caaaaggacc aagtgtgttc ccactcgccc ctagcagcaa gagtacatcc
```

-continued

```
 421 gggggcactg cagcactcgg ctgcctcgtc aaggattatt ttccagagcc agtaaccgtg
 481 agctggaaca gtggagcact cacttctggt gtccatactt ttcctgctgt cctgcaaagc
 541 tctggcctgt actcactcag ctccgtcgtg accgtgccat cttcatctct gggcactcag
 601 acctacatct gtaatgtaaa ccacaagcct agcaatacta aggtcgataa gcgggtggaa
 661 cccaagagct cgacaagac tcacacttgt ccccatgcc ctgcccctga acttctgggc
 721 ggtcccagcg tcttttgtt cccaccaaag cctaaagata tctgatgat aagtagaaca
 781 cccgaggtga catgtgttgt tgtagacgtt tcccacgagg acccagaggt taagttcaac
 841 tggtacgttg atggagtcga agtacataat gctaagacca gcctagaga ggagcagtat
 901 aatagtacat accgtgtagt cagtgttctc acagtgctgc accaagactg gctcaacggc
 961 aaagaataca aatgcaaagt gtccaacaaa gcactcccag ccctatcga agactatt
1021 agtaaggcaa aggggcagcc tcgtgaacca caggtgtaca ctctgccacc cagtagagag
1081 gaaatgacaa agaaccaagt ctcattgacc tgcctggtga aaggcttcta ccccagcgac
1141 atcgccgttg agtgggagag taacggtcag cctgagaaca attacaagac aaccccccca
1201 gtgctggata gtgacgggtc tttctttctg tacagtaagc tgactgtgga caagtcccgc
1261 tggcagcagg gtaacgtctt cagctgttcc gtgatgcacg aggcattgca caaccactac
1321 acccagaagt cactgagcct gagcccaggg aag
```

Protein Sequence Defining the Full Length Chimeric 07F01 C102S Heavy Chain
(Mouse Heavy Chain Variable Region and Human IgG1 Constant Region)

(SEQ ID NO: 156)

```
  1 evkllesggg lvqpggslkl scaasgfdfs rhwmswvrla pgkglewiae inpdsrtiny
 61 tpslkekfii srdnaknslf lqmnrvrsed talyycarrv rihyygamds wgqgtsvtvs
121 sastkgpsvf plapssksts ggtaalgclv kdyfpepvtv swnsgaltsg vhtfpavlqs
181 sglyslssvv tvpssslgtq tyicnvnhkp sntkvdkrve pkscdkthtc ppcpapellg
241 gpsvflfppk pkdtlmisrt pevtcvvvdv shedpevkfn wyvdgvevhn aktkpreeqy
301 nstyrvvsvl tvlhqdwlng keykckvsnk alpapiekti skakgqprep qvytlppsre
361 emtknqvslt clvkgfypsd iavewesngq pennykttpp vldsdgsffl yskltvdksr
421 wqqgnvfscs vmhealhnhy tqkslslspg k
```

Nucleic Acid Sequence Encoding the Full Length Chimeric 07F01 Light Chain
(Mouse Kappa Chain Variable Region and Human Kappa Constant Region)

(SEQ ID NO: 157)

```
  1 gacattgtgt tgacccagtc tcaaaaaatc gtgtccacat cagtaggagc cagggtcagc
 61 gtcacctgca aggccagtca gaatgtgggt tctagtttag tctggtatca acagaaacca
121 ggtcaatctc ctaaaacact gatttactcg gcatccttcc ggtacagtgg agtccctgat
181 cgcttcacag gcagtggatc tgggacagat ttcactctca ccatcagcaa tgtgcagtct
241 gaagacttgg cagattattt ctgtcaacaa tataataact atccgctcac gttcggtgct
301 gggaccaagc tggagctgaa acgcacagtc gccgctccct ccgtgttcat ctttccacca
361 agtgatgagc aactgaagtc tggtactgct tcagtcgtgt gtctgctgaa caatttctac
421 cctcgagaag ccaaagtcca atggaaggta gacaacgcac tgcagtccgg caatagccaa
481 gaatcagtta ccgaacagga ttcaaaggac agtacatatt ccctgagcag cactctgacc
541 ctgtcaaagg ccgattacga gaaacacaag gtctatgctt gcgaagtgac acatcaggga
601 ctgtccagcc cagtgacaaa atctttttaac cgtggggagt gt
```

Protein Sequence Defining the Full Length Chimeric 07F01 Light Chain (Mouse Kappa Chain Variable Region and Human Kappa Constant Region)
(SEQ ID NO: 158)

```
  1 divltqsqki vstsvgarvs vtckasqnvg sslvwyqqkp gqspktliys asfrysgvpd 61 rftgsgsgtd ftltisnvqs edladyfcqq ynnypltfga gtklelkrtv aapsvfifpp 121 sdeqlksgta svvcllnnfy preakvqwkv dnalqsgnsq esvteqdskd styslsstlt 181 lskadyekhk vyacevthqg lsspvtksfn rgec
```

Nucleic Acid Sequence Encoding the Full Length Chimeric 29B06 Heavy Chain (Mouse Heavy Chain Variable Region and Human IgG1 Constant Region)
(SEQ ID NO: 159)

```
   1 gaggtgcagc ttcaggagtc aggacctagc ctcgtgaaac cttctcagac tctgtccctc 61 acctgttctg tcactggcga ctccatcacc agtggttact ggaactggat ccggaaattc 121 ccagggaata acttgagta catggggtac ataagctaca gtggtaaaac ttactacaat 181 ccatctctca aaagtcgaat ctccatcact cgagacacat ccaagaacca ttactacctg 241 cagttgattt ctgtgactgc tgaggacaca gccacatatt actgtgcaag gtctaagtac 301 gactatgcta tggactactg ggtcaagga acctcagtca ccgtctcctc agcctcaaca 361 aaaggaccaa gtgtgttccc actcgcccct agcagcaaga gtacatccgg gggcactgca 421 gcactcggct gcctcgtcaa ggattatttt ccagagccag taaccgtgag ctggaacagt 481 ggagcactca cttctggtgt ccatactttt cctgctgtcc tgcaaagctc tggcctgtac 541 tcactcagct ccgtcgtgac cgtgccatct tcatctctgg cactcagac ctacatctgt 601 aatgtaaacc acaagcctag caatactaag gtcgataagc gggtggaacc caagagctgc 661 gacaagactc acacttgtcc cccatgccct gcccctgaac ttctgggcgg tcccagcgtc 721 ttttttgttcc caccaaagcc taaagatact ctgatgataa gtagaacacc cgaggtgaca 781 tgtgttgttg tagacgtttc ccacgaggac ccagaggtta agttcaactg gtacgttgat 841 ggagtcgaag tacataatgc taagaccaag cctagagagg agcagtataa tagtacatac 901 cgtgtagtca gtgttctcac agtgctgcac caagactggc tcaacggcaa agaatacaaa 961 tgcaaagtgt ccaacaaagc actcccagcc ctatcgaga agactattag taaggcaaag 1021 gggcagcctc gtgaaccaca ggtgtacact ctgccaccca gtagagagga aatgacaaag 1081 aaccaagtct cattgacctg cctggtgaaa ggcttctacc ccagcgacat cgccgttgag 1141 tgggagagta acggtcagcc tgagaacaat tacaagacaa cccccccagt gctggatagt 1201 gacgggtctt tctttctgta cagtaagctg actgtggaca gtcccgctg gcagcagggt 1261 aacgtcttca gctgttccgt gatgcacgag gcattgcaca accactacac ccagaagtca 1321 ctgagcctga gcccagggaa g
```

Protein Sequence Defining the Full Length Chimeric 29B06 Heavy Chain (Mouse Heavy Chain Variable Region and Human IgG1 Constant Region)
(SEQ ID NO: 160)

```
  1 evqlqesgps lvkpsqtlsl tcsvtgdsit sgywnwirkf pgnkleymgy isysgktyyn 61 pslksrisit rdtsknhyyl qlisvtaedt atyycarsky dyamdywgqg tsvtvssast 121 kgpsvfplap sskstsggta algclvkdyf pepvtvswns galtsgvhtf pavlqssgly 181 slssvvtvps sslgtqtyic nvnhkpsntk vdkrvepksc dkthtcppcp apellggpsv 241 flfppkpkdt lmisrtpevt cvvvdvshed pevkfnwyvd gvevhnaktk preeqynsty 301 rvvsvltvlh qdwlngkeyk ckvsnkalpa piektiskak gqprepqvyt lppsreemtk 361 nqvsltclvk gfypsdiave wesngqpenn ykttppvlds dgsfflyskl tvdksrwqqg 421 nvfscsvmhe alhnhytqks lslspgk
```

Nucleic Acid Sequence Encoding the Full Length Chimeric 29B06 Light Chain
(Mouse Kappa Chain Variable Region and Human Kappa Constant Region)

(SEQ ID NO: 161)

```
  1 gacattgtgc tgacccaatc tccagcttct ttggctgtgt ctctaggaca gagggccacc 61 atctcctgca gagccagcga aattgttgat aattttggca ttagttttat gaactggttc 121 caacagaaac caggacagcc acccaaactc ctcatctatg ctgcatccaa ccaaggatcc 181 ggggtccctg ccaggtttag tggcagtggg tctgggacag acttcagcct caacatccat 241 cctgtggagg aggatgatac tgcaatgtat ttctgtcagc aaagtaagga ggttcctccg 301 acgttcggtg gaggcaccaa gctggaaatc aaacgcacag tcgccgctcc ctccgtgttc 361 atctttccac caagtgatga gcaactgaag tctggtactg cttcagtcgt gtgtctgctg 421 aacaatttct accctcgaga agccaaagtc caatggaagg tagacaacgc actgcagtcc 481 ggcaatagcc aagaatcagt taccgaacag gattcaaagg acagtacata ttccctgagc 541 agcactctga ccctgtcaaa ggccgattac gagaaacaca aggtctatgc ttgcgaagtg 601 acacatcagg gactgtccag cccagtgaca aaatctttta ccgtgggga gtgt
```

Protein Sequence Defining the Full Length Chimeric 29B06 Light Chain (Mouse
Kappa Chain Variable Region and Human Kappa Constant Region)

(SEQ ID NO: 162)

```
  1 divltqspas layslgqrat iscraseivd nfgisfmnwf qqkpgqppkl liyaasnqgs 61 gvparfsgsg sgtdfslnih pveeddtamy fcqqskevpp tfggtklei krtvaapsvf 121 ifppsdeqlk sgtasvvcll nnfypreakv qwkvdnalqs gnsqesvteq dskdstysls 181 stltlskady ekhkvyacev thqglsspvt ksfnrgec
```

Nucleic Acid Sequence Encoding the Full Length Humanized Sh07F01 Hv3-48
Heavy Chain (Humanized Heavy Chain Variable Region and Human IgG1 Constant Region)

(SEQ ID NO: 163)

```
   1 gaggttcagc tggtagaatc cggaggaggg ttggtccaac tggtggatc actcagactt 61 tcatgcgccg ccagcggctt tgacttctca cgacattgga tgagctgggt ccggcaggct 121 ccaggcaagg gcctcgagtg ggttagcgag atcaatccag acagcagaac cattaactat 181 acacccagtc tgaaggagcg gttcaccata agccgtgata atgccaagaa ctccctgtac 241 ttgcagatga actccttgcg cgctgaagat acagctgtgt actattgtgc aaggcgcgtg 301 cgaatccact attacgggc aatggattct tggggccagg gtactaccgt gactgtgagt 361 tctgcctcaa caaaaggacc aagtgtgttc ccactcgccc ctagcagcaa gagtacatcc 421 gggggcactg cagcactcgg ctgcctcgtc aaggattatt ttccagagcc agtaaccgtg 481 agctggaaca gtggagcact cacttctggt gtccatactt ttcctgctgt cctgcaaagc 541 tctggcctgt actcactcag ctccgtcgtg accgtgccat cttcatctct gggcactcag 601 acctacatct gtaatgtaaa ccacaagcct agcaatacta aggtcgataa gcgggtggaa 661 cccaagagct gcgacaagac tcacacttgt ccccatgcc ctgccctga acttctgggc 721 ggtcccagcg tcttttttgtt cccaccaaag cctaaagata tctgatgat aagtagaaca 781 cccgaggtga catgtgttgt tgtagacgtt tcccacgagg acccagaggt taagttcaac 841 tggtacgttg atggagtcga agtacataat gctaagacca gcctagaga ggagcagtat 901 aatagtacat accgtgtagt cagtgttctc acagtgctgc accaagactg gctcaacggc 961 aaagaataca atgcaaagt gtccaacaaa gcactcccag cccctatcga gaagactatt 1021 agtaaggcaa aggggcagcc tcgtgaacca caggtgtaca ctctgccacc cagtagagag 1081 gaaatgacaa agaaccaagt ctcattgacc tgcctggtga aaggcttcta ccccagcgac 1141 atcgccgttg agtgggagag taacggtcag cctgagaaca attacaagac aacccccccca 1201 gtgctggata tgacgggtc tttctttctg tacagtaagc tgactgtgga caagtcccgc
```

```
1261 tggcagcagg gtaacgtctt cagctgttcc gtgatgcacg aggcattgca caaccactac 1321 acccagaagt cactgagcct gagcccaggg aag
```

Protein Sequence Defining the Full Length Humanized Sh07F01 Hv3-48 Heavy
Chain(Humanized Heavy Chain Variable Region and Human IgG1 Constant Region)

(SEQ ID NO: 164)

```
  1 evqlvesggg lvqpggslrl scaasgfdfs rhwmswvrqa pgkglewvse inpdsrtiny 61 tpslkerfti srdnaknsly lqmnslraed tavyycarrv rihyygamds wgqgttvtvs 121 sastkgpsvf plapssksts ggtaalgclv kdyfpepvtv swnsgaltsg vhtfpavlqs 181 sglyslssvv tvpssslgtq tyicnvnhkp sntkvdkrve pkscdkthtc ppcpapellg 241 gpsvflfppk pkdtlmisrt pevtcvvvdv shedpevkfn wyvdgvevhn aktkpreeqy 301 nstyrvvsvl tvlhqdwlng keykckvsnk alpapiekti skakgqprep qvytlppsre 361 emtknqvslt clvkgfypsd iavewesngq pennykttpp vldsdgsffl ysklvtdksr 421 wqqgnvfscs vmhealhnhy tqkslslspg k
```

Nucleic Acid Sequence Encoding the Full Length Humanized Sh07F01 Hv3-48 D28T
T60A L63V E65G Heavy Chain (Humanized Heavy Chain Variable Region and Human IgG1
Constant Region)

(SEQ ID NO: 165)

```
  1 gaggttcagc tggtagaatc cggaggaggg ttggtccaac ctggtggatc actcagactt 61 tcatgcgccg ccagcggctt taccttctca cgacattgga tgagctgggt ccggcaggct 121 ccaggcaagg gcctcgagtg ggttagcgag atcaatccag acagcagaac cattaactat 181 gcccccagtg tgaagggccg gttcaccata agccgtgata atgccaagaa ctccctgtac 241 ttgcagatga actccttgcg cgctgaagat acagctgtgt actattgtgc aaggcgcgtg 301 cgaatccact attacggggc aatggattct tggggccagg gtactaccgt gactgtgagt 361 tctgcctcaa caaaaggacc aagtgtgttc ccactcgccc ctagcagcaa gagtacatcc 421 gggggcactg cagcactcgg ctgcctcgtc aaggattatt ttccagagcc agtaaccgtg 481 agctggaaca gtggagcact cacttctggt gtccatactt ttcctgctgt cctgcaaagc 541 tctggcctgt actcactcag ctccgtcgtg accgtgccat cttcatctct gggcactcag 601 acctacatct gtaatgtaaa ccacaagcct agcaatacta aggtcgataa gcgggtggaa 661 cccaagagct gcgacaagac tcacacttgt cccccatgcc ctgcccctga acttctgggc 721 ggtcccagcg tcttttttgtt cccaccaaag cctaaagata ctctgatgat aagtagaaca 781 cccgaggtga catgtgttgt tgtagacgtt tcccacgagg acccagaggt taagttcaac 841 tggtacgttg atggagtcga agtacataat gctaagacca agcctagaga ggagcagtat 901 aatagtacat accgtgtagt cagtgttctc acagtgctgc accaagactg gctcaacggc 961 aaagaataca aatgcaaagt gtccaacaaa gcactcccag cccctatcga aagactatt 1021 agtaaggcaa aggggcagcc tcgtgaacca caggtgtaca ctctgccacc cagtagagag 1081 gaaatgacaa agaaccaagt ctcattgacc tgcctggtga aaggcttcta ccccagcgac 1141 atcgccgttg agtgggagag taacggtcag cctgagaaca attacaagac aaccccccca 1201 gtgctggata gtgacgggtc tttctttctg tacagtaagc tgactgtgga caagtcccgc 1261 tggcagcagg gtaacgtctt cagctgttcc gtgatgcacg aggcattgca caaccactac 1321 acccagaagt cactgagcct gagcccaggg aag
```

Protein Sequence Defining the Full Length Humanized Sh07F01 Hv3-48 D28T T60A
L63V E65G Heavy Chain (Humanized Heavy Chain Variable Region and Human IgG1
Constant Region)

(SEQ ID NO: 166)

```
  1 evqlvesggg lvqpggslrl scaasgftfs rhwmswvrqa pgkglewvse inpdsrtiny 61 apsvkgrfti srdnaknsly lqmnslraed tavyycarrv rihyygamds wgqgttvtvs
```

```
121 sastkgpsvf plapssksts ggtaalgclv kdyfpepvtv swnsgaltsg vhtfpavlqs 181 sglyslssvv tvpssslgtq tyicnvnhkp sntkvdkrve pkscdkthtc ppcpapellg 241 gpsvflfppk pkdtlmisrt pevtcvvvdv shedpevkfn wyvdgvevhn aktkpreeqy 301 nstyrvvsvl tvlhqdwlng keykckvsnk alpapiekti skakgqprep qvytlppsre 361 emtknqvslt clvkgfypsd iavewesngq pennykttpp vldsdgsffl yskltvdksr 421 wqqgnvfscs vmhealhnhy tqkslslspg k
```

Nucleic Acid Sequence Encoding the Full Length Humanized HE L 07F01 Kv1-9
Light Chain (Humanized Kappa Chain Variable Region and Human Constant Region)
(SEQ ID NO: 167)

```
  1 gatatccagt tgactcagtc tcagtccttt gtgagtacat cagtgggcga cagggtcacc 61 gtgacctgcc gagcatcaca gaacgttgga agctctcttg tctggtatca gcaaaagcct 121 gggaagagcc ccaaaaccct catctattct gcttcctttc tgtactccgg cgtaccaagt 181 agattctctg gtagcggatc cgggacagag ttcactctca caattagcag tgtgcagcct 241 gaggatttcg ccgactactt ctgtcagcaa tacaataact atcccctgac tttggtggc 301 ggcaccaaag tggaaatcaa gcgcacagtt gctgccccca gcgtgttcat ttcccacct 361 agcgatgagc agctgaaaag cggtactgcc tctgtcgtat gcttgctcaa caactttac 421 ccacgtgagg ctaaggtgca gtggaaagtg gataatgcac ttcaatctgg aaacagtcaa 481 gagtccgtga cagaacagga cagcaaagac tcaacttatt cactctcttc caccctgact 541 ctgtccaagg cagactatga aaaacacaag gtatacgcct gcgaggttac acaccagggt 601 ttgtctagtc ctgtcaccaa gtccttcaat agggccgaat gt
```

Protein Sequence Defining the Full Length Humanized HE L 07F01 Kv1-9 Light
Chain (Humanized Kappa Chain Variable Region and Human Constant Region)
(SEQ ID NO: 168)

```
  1 diqltqsqsf vstsvgdrvt vtcrasqnvg sslvwyqqkp gkspktliys asflysgvps 61 rfsgsgsgte ftltissvqp edfadyfcqq ynnypltfgg gtkveikrtv aapsvfifpp 121 sdeqlksgta svvcllnnfy preakvqwkv dnalqsgnsq esvteqdskd styslsstlt 181 lskadyekhk vyacevthqg lsspvtksfn rgec
```

Nucleic Acid Sequence Encoding the Full Length Humanized sh07F01 Kv1-9 F1
Light Chain (Humanized Kappa Chain Variable Region and Human Constant Region)
(SEQ ID NO: 169)

```
  1 gacattcagc tgactcagtc gccgtcgttt ttgtcggcgt ccgtgggtga cagagtgact 61 atcacatgtc gcgcttcgca aaacgtcgga tcatcgcttg tgtggtatca gcagaaaccc 121 ggtaaagccc ctaagaccct catctattca gcgtcatttc tgtatagcgg gtcccctca 181 cggttcagcg gatccggctc cgggaccgag ttcacactca ctatttcgag cttgcagccg 241 gaagatttg caacgtacta ctgccagcaa tacaataact acccactcac gttcggaggg 301 ggaacgaagg tagagatcaa gcgcacagtt gctgccccca gcgtgttcat tttcccacct 361 agcgatgagc agctgaaaag cggtactgcc tctgtcgtat gcttgctcaa caactttac 421 ccacgtgagg ctaaggtgca gtggaaagtg gataatgcac ttcaatctgg aaacagtcaa 481 gagtccgtga cagaacagga cagcaaagac tcaacttatt cactctcttc caccctgact 541 ctgtccaagg cagactatga aaaacacaag gtatacgcct gcgaggttac acaccagggt 601 ttgtctagtc ctgtcaccaa gtccttcaat agggccgaat gt
```

Protein Sequence Defining the Full Length Humanized sh07F01 Kv1-9 F1 Light
Chain (Humanized Kappa Chain Variable Region and Human Constant Region)
(SEQ ID NO: 170)

```
  1 diqltqspsf lsasvgdrvt itcrasqnvg sslvwyqqkp gkapktliys asflysgvps 61 rfsgsgsgte ftltisslqp edfatyycqq ynnypltfgg gtkveikrtv aapsvfifpp
```

-continued 121 sdeqlksgta svvcllnnfy preakvqwkv dnalqsgnsq esvteqdskd styslsstlt 181 lskadyekhk vyacevthqg lsspvtksfn rgec Nucleic Acid Sequence Encoding the Full Length Humanized Sh29B06 Hv4-59
Heavy Chain (Humanized Heavy Chain Variable Region and Human IgG1 Constant Region)
(SEQ ID NO: 171)

```
   1 caagttcagc tgcaagaatc cggaccagga ttggtcaaac cttcagagac actcagcctg 61 acttgcaccg tgagcggtgg cagcatatcc tccggttatt ggaactggat ccggcagcca 121 ccaggcaagg gcctcgagtg gattggctac atcagctata gcgggaaaac ctattacaac 181 cccagtctga gagccgagt gaccataagc gtcgatacaa gtaagaacca gttctccctg 241 aagctctcat ccgtgaccgc cgctgataca gctgtgtact attgtgcaag gtcaaagtat 301 gactacgcaa tggactattg gggccagggt actctggtga ctgtgagttc tgcctcaaca 361 aaaggaccaa gtgtgttccc actcgcccct agcagcaaga gtacatccgg ggcactgca 421 gcactcggct gcctcgtcaa ggattatttt ccagagccag taaccgtgag ctggaacagt 481 ggagcactca cttctggtgt ccatactttt cctgctgtcc tgcaaagctc tggcctgtac 541 tcactcagct ccgtcgtgac cgtgccatct tcatctctgg cactcagac ctacatctgt 601 aatgtaaacc acaagcctag caatactaag gtcgataagc gggtggaacc caagagctgc 661 gacaagactc acacttgtcc cccatgccct gcccctgaac ttctgggcgg tcccagcgtc 721 tttttgttcc caccaaagcc taaagatact ctgatgataa gtagaacacc cgaggtgaca 781 tgtgttgttg tagacgtttc ccacgaggac ccagaggtta agttcaactg gtacgttgat 841 ggagtcgaag tacataatgc taagaccaag cctagagagg agcagtataa tagtacatac 901 cgtgtagtca gtgttctcac agtgctgcac caagactggc tcaacggcaa agaatacaaa 961 tgcaaagtgt ccaacaaagc actcccagcc cctatcgaga agactattag taaggcaaag 1021 gggcagcctc gtgaaccaca ggtgtacact ctgccaccca gtagagagga aatgacaaag 1081 aaccaagtct cattgacctg cctggtgaaa ggcttctacc ccagcgacat cgccgttgag 1141 tgggagagta acggtcagcc tgagaacaat tacaagacaa cccccccagt gctggatagt 1201 gacgggtctt tctttctgta cagtaagctg actgtggaca agtcccgctg cagcagggt 1261 aacgtcttca gctgttccgt gatgcacgag gcattgcaca accactacac ccagaagtca 1321 ctgagcctga gcccagggaa g
```

Protein Sequence Defining the Full Length Humanized Sh29B06 Hv4-59 Heavy
Chain (Humanized Heavy Chain Variable Region and Human IgG1 Constant Region)
(SEQ ID NO: 172)

```
   1 qvqlqesgpg lvkpsetlsl tctvsggsis sgywnwirqp pgkglewigy isysgktyyn 61 pslksrvtis vdtsknqfsl klssvtaadt avyycarsky dyamdywgqg tlvtvssast 121 kgpsvfplap sskstsggta algclvkdyf pepvtvswns galtsgvhtf pavlqssgly 181 slssvvtvps sslgtqtyic nvnhkpsntk vdkrvepksc dkthtcppcp apellggpsv 241 flfppkpkdt lmisrtpevt cvvvdvshed pevkfnwyvd gvevhnaktk preeqynsty 301 rvvsvltvlh qdwlngkeyk ckvsnkalpa piektiskak gqprepqvyt lppsreemtk 361 nqvsltclvk gfypsdiave wesngqpenn ykttppvlds dgsfflyskl tvdksrwqqg 421 nvfscsvmhe alhnhytqks lslspgk
```

Nucleic Acid Sequence Encoding the Full Length Humanized Hu29B06 Hv4-59
Heavy Chain (Humanized Heavy Chain Variable Region and Human IgG1 Constant Region)
(SEQ ID NO: 173)

```
   1 caagttcagc tgcaagaatc cggaccagga ttggtcaaac ccagcgaaac actctctctt 61 acatgcaccg tgagcggcga ctctatcacc tcagggtatt ggaattggat tcggaaccc 121 ccaggcaaga agctcgagta catgggttac atcagttaca gcgggaaaac ctactataac
```

-continued
```
 181 cccagtctga agagcagaat caccataagc cgtgatacct caagaaccag tactccctg 241 aagctgagtt ccgtaacagc agctgataca gctgtgtact attgtgcaag gagtaagtat 301 gactacgcaa tggactattg gggccagggt actcttgtga ctgtgagttc tgcctcaaca 361 aaaggaccaa gtgtgttccc actcgcccct agcagcaaga gtacatccgg ggcactgca 421 gcactcggct gcctcgtcaa ggattatttt ccagagccag taaccgtgag ctggaacagt 481 ggagcactca cttctggtgt ccatactttt cctgctgtcc tgcaaagctc tggcctgtac 541 tcactcagct ccgtcgtgac cgtgccatct tcatctctgg cactcagac ctacatctgt 601 aatgtaaacc acaagcctag caatactaag gtcgataagc gggtggaacc caagagctgc 661 gacaagactc acacttgtcc cccatgccct gcccctgaac ttctgggcgg tcccagcgtc 721 ttttgttcc caccaaagcc taaagatact ctgatgataa gtagaacacc cgaggtgaca 781 tgtgttgttg tagacgtttc ccacgaggac ccagaggtta agttcaactg gtacgttgat 841 ggagtcgaag tacataatgc taagaccaag cctagagagg agcagtataa tagtacatac 901 cgtgtagtca gtgttctcac agtgctgcac caagactggc tcaacggcaa agaatacaaa 961 tgcaaagtgt ccaacaaagc actcccagcc ctatcgaga agactattag taaggcaaag 1021 gggcagcctc gtgaaccaca ggtgtacact ctgccaccca gtagagagga aatgacaaag 1081 aaccaagtct cattgacctg cctggtgaaa ggcttctacc ccagcgacat cgccgttgag 1141 tgggagagta acggtcagcc tgagaacaat tacaagacaa ccccccccagt gctggatagt 1201 gacgggtctt tcttctctgta cagtaagctg actgtggaca agtcccgctg gcagcagggt 1261 aacgtcttca gctgttccgt gatgcacgag gcattgcaca accactacac ccagaagtca 1321 ctgagcctga gcccagggaa g
```

Protein Sequence Defining the Full Length Humanized Hu29B06 Hv4-59 Heavy
Chain (Humanized Heavy Chain Variable Region and Human IgG1 Constant Region)
(SEQ ID NO: 174)
```
  1 qvqlgesgpg lvkpsetlsl tctvsgdsit sgywnwirkp pgkkleymgy isysgktyyn 61 pslksritis rdtsknqysl klssvtaadt avyycarsky dyamdywgqg tlvtvssast 121 kgpsvfplap sskstsggta algclvkdyf pepvtvswns galtsgvhtf pavlqssgly 181 slssvvtvps sslgtqtyic nvnhkpsntk vdkrvepksc dkthtcppcp apellggpsv 241 flfppkpkdt lmisrtpevt cvvvdvshed pevkfnwyvd gvevhnaktk preeqynsty 301 rvvsvltvlh qdwlngkeyk ckvsnkalpa piektiskak gqprepqvyt lppsreemtk 361 nqvsltclvk gfypsdiave wesngqpenn ykttppvlds dgsffyskl tvdksrwqqg 421 nvfscsvmhe alhnhytqks lslspgk
```

Nucleic Acid Sequence Encoding the Full Length Humanized Hu29B06 Hv4-59
D27G T30S M48I I67V Y78F Heavy Chain (Humanized Heavy Chain Variable Region and
Human IgG1 Constant Region)
(SEQ ID NO: 175)
```
  1 caagttcagc tgcaagaatc cggaccagga ttggtcaaac cttcagagac actcagcctg 61 acttgcaccg tgagcggtgg cagcatatcc tccggttatt ggaactggat ccggaagcca 121 ccaggcaaga agctcgagta cattggctac atcagctata gcgggaaaac ctattacaac 181 cccagtctga agagccgagt gaccataagc agggatacaa gtaagaacca gttctccctg 241 aagctctcat ccgtgaccgc cgctgataca gctgtgtact attgtgcaag gtcaaagtat 301 gactacgcaa tggactattg gggccagggt actctggtga ctgtgagttc tgcctcaaca 361 aaaggaccaa gtgtgttccc actcgcccct agcagcaaga gtacatccgg ggcactgca 421 gcactcggct gcctcgtcaa ggattatttt ccagagccag taaccgtgag ctggaacagt 481 ggagcactca cttctggtgt ccatactttt cctgctgtcc tgcaaagctc tggcctgtac
```

```
541 tcactcagct ccgtcgtgac cgtgccatct tcatctctgg cactcagac ctacatctgt 601 aatgtaaacc acaagcctag caatactaag gtcgataagc gggtggaacc caagagctgc 661 gacaagactc acacttgtcc cccatgccct gcccctgaac ttctgggcgg tcccagcgtc 721 tttttgttcc caccaaagcc taaagatact ctgatgataa gtagaacacc cgaggtgaca 781 tgtgttgttg tagacgtttc ccacgaggac ccagaggtta agttcaactg gtacgttgat 841 ggagtcgaag tacataatgc taagaccaag cctagagagg agcagtataa tagtacatac 901 cgtgtagtca gtgttctcac agtgctgcac caagactggc tcaacggcaa agaatacaaa 961 tgcaaagtgt ccaacaaagc actcccagcc cctatcgaga agactattag taaggcaaag 1021 gggcagcctc gtgaaccaca ggtgtacact ctgccaccca gtagagagga aatgacaaag 1081 aaccaagtct cattgacctg cctggtgaaa ggcttctacc ccagcgacat cgccgttgag 1141 tgggagagta acggtcagcc tgagaacaat tacaagacaa cccccccagt gctggatagt 1201 gacgggtctt ctttctgtac cagtaagctg actgtggaca gtcccgctg gcagcagggt 1261 aacgtcttca gctgttccgt gatgcacgag gcattgcaca accactacac ccagaagtca 1321 ctgagcctga gcccagggaa g
```

Protein Sequence Defining the Full Length Humanized Hu29B06 Hv4-59 D27G
T30S M48I I67V Y78F Heavy Chain (Humanized Heavy Chain Variable Region and Human
IgG1 Constant Region)
(SEQ ID NO: 176)

```
  1 qvglgesgpg lvkpsetlsl tctvsggsis sgywnwirkp pgkkleyigy isysgktyyn 61 pslksrvtis rdtsknqfsl klssvtaadt avyycarsky dyamdywgqg tlvtvssast 121 kgpsvfplap sskstsggta alglclvkdyf pepvtvswns galtsgvhtf pavlqssgly 181 slssvvtvps sslgtqtyic nvnhkpsntk vdkrvepksc dkthtcppcp apellggpsv 241 flfppkpkdt lmisrtpevt cvvvdvshed pevkfnwyvd gvevhnaktk preeqynsty 301 rvvsvltvlh qdwlngkeyk ckvsnkalpa piektiskak gqprepqvyt lppsreemtk 361 nqvsltclvk gfypsdiave wesnggpenn ykttppvlds dgsfflyskl tvdksrwqqg 421 nvfscsvmhe alhnhytqks lslspgk
```

Nucleic Acid Sequence Encoding the Full Length Humanized Sh29B06 Kv2-28 Light
Chain (Humanized Kappa Chain Variable Region and Human Constant Region)
(SEQ ID NO: 177)

```
  1 gatatcgtta tgacccagag cccacttagt ttgcctgtta ctcctggcga gcctgccagt 61 atttcttgcc gtgctagcga aatcgtggat aactttggta tatcattcat gaattggtat 121 ctccaaaaac ctggccaaag cccccagctc cttatctacg ccgctagcaa ccaggggtcc 181 gggtacctg atagatttc aggcagcggc tctggaaccg acttcacact gaagatttcc 241 cgggtggagg ccgaggacgt gggcgtgtac tattgtcaac agtccaagga agtccctccc 301 actttcggcg gtgggacaaa ggttgagatt aagcgcacag ttgctgcccc cagcgtgttc 361 attttcccac ctagcgatga gcagctgaaa agcggtactg cctctgtcgt atgcttgctc 421 aacaactttt acccacgtga ggctaaggtg cagtggaaag tggataatgc acttcaatct 481 ggaaacagtc aagagtccgt gacagaacag gacagcaaag actcaactta ttcactctct 541 tccaccctga ctctgtccaa ggcagactat gaaaaacaca aggtatacgc ctgcgaggtt 601 acacaccagg gtttgtctag tcctgtcacc aagtccttca ataggggcga atgt
```

Protein Sequence Defining the Full Length Humanized Sh29B06 Kv2-28 Light Chain
(Humanized Kappa Chain Variable Region and Human Constant Region)
(SEQ ID NO: 178)

```
  1 divmtqspls lpvtpgepas iscraseivd nfgisfmnwy lqkpggspql liyaasnqgs 61 gvpdrfsgsg sgtdftlkis rveaedvgvy ycqqskevpp tfgggtkvei krtvaapsvf
```

-continued

```
121 ifppsdeqlk sgtasvvcll nnfypreakv qwkvdnalqs gnsqesvteq dskdstysls 181 stltlskady ekhkvyacev thqglsspvt ksfnrgec
```

For convenience, Table 18 provides a concordance chart showing the SEQ ID NO. of each sequence discussed in this Example.

TABLE 18

| SEQ ID NO. | Nucleic Acid or Protein |
|---|---|
| 150 | Human IgG1 constant-nucleic acid |
| 151 | Human IgG1 constant-protein |
| 152 | Human Kappa constant (used for chimeric antibodies)-nucleic acid |
| 153 | Human Kappa constant (used for humanized antibodies)-nucleic acid |
| 154 | Human Kappa constant (used for chimeric and humanized antibodies)-protein |
| 155 | Chimeric 07F01 C102S Mouse Heavy Chain Variable + Human IgG1 constant-nucleic acid |
| 156 | Chimeric 07F01 C102S Mouse Heavy Chain Variable + Human IgG1 constant-protein |
| 157 | Chimeric 07F01 Mouse Light Chain Variable + Human Kappa constant-nucleic acid |
| 158 | Chimeric 07F01 Mouse Light Chain Variable + Human Kappa constant-protein |
| 159 | Chimeric 29B06 Mouse Heavy Chain Variable + Human IgG1 constant-nucleic acid |
| 160 | Chimeric 29B06 Mouse Heavy Chain Variable + Human IgG1 constant-protein |
| 161 | Chimeric 29B06 Mouse Light Chain Variable + Human Kappa constant-nucleic acid |
| 162 | Chimeric 29B06 Mouse Light Chain Variable + Human Kappa constant-protein |
| 163 | Humanized Sh07F01 Hv3-48 Heavy Human Variable + Human IgG1 constant-nucleic acid |
| 164 | Humanized Sh07F01 Hv3-48 Heavy Human Variable + Human IgG1 constant-protein |
| 165 | Humanized Sh07F01 Hv3-48 D28T T60A L63V E65G Heavy Human Variable + Human IgG1 constant-nucleic acid |
| 166 | Humanized Sh07F01 Hv3-48 D28T T60A L63V E65G Heavy Human Variable + Human IgG1 constant-protein |
| 167 | Humanized HE L 07F01 Kv1-9 Human Variable + Human Kappa constant-nucleic acid |
| 168 | Humanized HE L 07F01 Kv1-9 Human Variable + Human Kappa constant-protein |
| 169 | Humanized sh07F01 Kv1-9 F1 Human Variable + Human Kappa constant-nucleic acid |
| 170 | Humanized sh07F01 Kv1-9 F1 Human Variable + Human Kappa constant-protein |
| 171 | Humanized Sh29B06 Hv4-59 Heavy Human Variable + Human IgG1 constant-nucleic acid |
| 172 | Humanized Sh29B06 Hv4-59 Heavy Human Variable + Human IgG1 constant-protein |
| 173 | Humanized Hu29B06 Hv4-59 Heavy Human Variable + Human IgG1 constant-nucleic acid |
| 174 | Humanized Hu29B06 Hv4-59 Heavy Human Variable + Human IgG1 constant-protein |
| 175 | Humanized Hu29B06 Hv4-59 D27G T30S M48I I67V Y78F Heavy Human Variable + Human IgG1 constant-nucleic acid |
| 176 | Humanized Hu29B06 Hv4-59 D27G T30S M48I I67V Y78F Heavy Human Variable + Human IgG1 constant-protein |
| 177 | Humanized Sh29B06 Kv2-28 Human Variable + Human Kappa constant-nucleic acid |
| 178 | Humanized Sh29B06 Kv2-28 Human Variable + Human Kappa constant-protein |

Table 19 below shows antibodies containing chimeric immunoglobulin heavy and light chains and each of the possible combinations of the full-length chimeric or humanized immunoglobulin heavy and light chains.

TABLE 19

| Antibody Name | Light Chain | Heavy Chain |
|---|---|---|
| Sh07F01-2 | Chimeric 07F01 Kappa (SEQ ID NO: 158) | Chimeric 07F01 C102S Heavy IgG1 (SEQ ID NO: 156) |
| Sh07F01-43 | HE L 07F01 Kv1-9 Kappa (SEQ ID NO: 168) | Sh07F01 Hv3-48 IgG1 (SEQ ID NO: 164) |
| Sh07F01-62 | HE L 07F01 Kv1-9 Kappa (SEQ ID NO: 168) | Sh07F01 Hv3-48 D28T T60A L63V E65G IgG1 (SEQ ID NO: 166) |
| Sh07F01-69 | Sh07F01 Kv1-9 F1 Kappa (SEQ ID NO: 170) | Sh07F01 Hv3-48 IgG1 (SEQ ID NO: 164) |
| Sh07F01-83 | Sh07F01 Kv1-9 F1 Kappa (SEQ ID NO: 170) | Sh07F01 Hv3-48 D28T T60A L63V E65G IgG1 (SEQ ID NO: 166) |
| Sh07F01-99 | Chimeric 07F01 Kappa (SEQ ID NO: 158) | Sh07F01 Hv3-48 IgG1 (SEQ ID NO: 164) |
| Sh07F01-100 | Chimeric 07F01 Kappa (SEQ ID NO: 158) | Sh07F01 Hv3-48 D28T T60A L63V E65G IgG1 (SEQ ID NO: 166) |
| Sh07F01-101 | HE L 07F01 Kv1-9 Kappa (SEQ ID NO: 168) | Chimeric 07F01 C102S Heavy IgG1 (SEQ ID NO: 156) |

TABLE 19-continued

| Antibody Name | Light Chain | Heavy Chain |
|---|---|---|
| Sh07F01-102 | Sh07F01 Kv1-9 F1 Kappa (SEQ ID NO: 170) | Chimeric 07F01 C102S Heavy IgG1 (SEQ ID NO: 156) |
| Sh29B06-1 | Chimeric 29B06 Kappa (SEQ ID NO: 162) | Chimeric 29B06 Heavy IgG1 (SEQ ID NO: 160) |
| Sh29B06-2 | Chimeric 29B06 Kappa (SEQ ID NO: 162) | Hu29B06 Hv4-59 IgG1 (SEQ ID NO: 174) |
| Sh29B06-4 | Chimeric 29B06 Kappa (SEQ ID NO: 162) | Sh29B06 Hv4-59 IgG1 (SEQ ID NO: 172) |
| Sh29B06-9 | Sh29B06 Kv2-28 Kappa (SEQ ID NO: 178) | Chimeric 29B06 Heavy IgG1 (SEQ ID NO: 160) |
| Sh29B06-23 | Sh29B06 Kv2-28 Kappa (SEQ ID NO: 178) | Hu29B06 Hv4-59 IgG1 (SEQ ID NO: 174) |
| Sh29B06-25 | Sh29B06 Kv2-28 Kappa (SEQ ID NO: 178) | Sh29B06 Hv4-59 IgG1 (SEQ ID NO: 172) |
| Sh29B06-78 | Sh29B06 Kv2-28 Kappa (SEQ ID NO: 178) | Hu29B06 Hv4-59 D27G T30S M48I I67V Y78F IgG1 (SEQ ID NO: 176) |
| Sh29B06-84 | Chimeric 29B06 Kappa (SEQ ID NO: 162) | Hu29B06 Hv4-59 D27G T30S M48I I67V Y78F IgG1 (SEQ ID NO: 176) |

The antibody constructs containing the full length chimeric heavy and light chains are designated below:

Chimeric 07F01 C102S=Full Length Chimeric 07F01 C102S Heavy Chain (Mouse Variable Region with C102S mutation and Human IgG1 Constant Region) (SEQ ID NO: 156) plus Full Length Chimeric 07F01 Light Chain (Mouse Variable Region and Human Kappa Constant Region) (SEQ ID NO: 158)

Chimeric 29B06=Full Length Chimeric 29B06 Heavy Chain (Mouse Variable Region and Human IgG1 Constant Region) (SEQ ID NO: 160) plus Full Length Chimeric 29B06 Light Chain (Mouse Variable Region and Human Kappa Constant Region) (SEQ ID NO: 162)

Two of the possible antibody constructs containing the full length immunoglobulin heavy and light chains containing humanized variable regions are designated below:

Sh07F01-62=Humanized Sh07F01 Hv3-48 D28T T60A L63V E65G Heavy Chain Variable Region and Human IgG1 Constant Region (SEQ ID NO: 166) plus HE L 07F01 Kv1-9 Light Chain Variable Region and Human Kappa Constant Region (SEQ ID NO: 168)

Sh29B06-78=Humanized Hu29B06 Hv4-59 D27G T30S M48I I67V Y78F Heavy Chain Variable Region and Human IgG1 Constant Region (SEQ ID NO: 176) plus Sh29B06 Kv2-28 Light Chain Variable Region and Human Kappa Constant Region (SEQ ID NO: 178)

B. Binding Affinities of Humanized and Chimeric Anti-RON Monoclonal Antibodies

The binding affinities and kinetics of interaction of monoclonal antibodies produced in Example 14 against recombinant human RON SEMA and PSI domains (rhRON SEMA+PSI) (R&D Systems, Inc., Minneapolis, Minn.) were measured by surface plasmon resonance using a Biacore T100 (Biacore (GE Healthcare), Piscataway, N.J.) instrument.

Goat anti-human IgG Fc (Jackson ImmunoResearch, Catalog No. 109-005-098) was immobilized on carboxymethylated dextran CM4 sensor chips (Biacore) by amine coupling (Biacore) using a standard coupling protocol according to the vendor's instructions. The analyses were performed at 37° C. using PBS (Invitrogen) containing 0.05% surfactant P20 (Biacore) as running buffer.

The antibodies were captured in individual flow cells at a flow rate of 60 µl/minute. Injection time was varied for each antibody to yield an $R_{max}$ between 30 and 60 RU. Buffer or rhRON SEMA+PSI diluted in running buffer was injected sequentially over a reference surface (no antibody captured) and the active surface (antibody to be tested) for 300 seconds at 60 µl/minute. The dissociation phase was monitored for up to 1200 seconds. The surface was then regenerated with two 60 second injections of Glycine pH 2.25 (made from Glycine pH 2.0 (Biacore) and pH 2.5 (Biacore)) at 60 µl/minute. For the initial screening, only one or two concentrations of rhRON SEMA+PSI were tested, typically 10.0 and 2.5 nM (results are summarized in Table 20).

Kinetic parameters were determined using the kinetic function of the BIAevaluation software (Biacore) with double reference subtraction. Kinetic parameters for each antibody, $k_a$ (association rate constant), $k_d$ (dissociation rate constant) and $K_D$ (equilibrium dissociation constant) were determined. Certain monoclonal antibodies were screened using cell culture media supernatant containing secreted antibody, and kinetic values of the monoclonal antibodies on rhRON SEMA+PSI at 37° C. are summarized in Table 20.

TABLE 20

| Antibody | ka (1/Ms) | kd (1/s) | KD (M) | n |
|---|---|---|---|---|
| Sh07F01-2 | 2.0E+06 | 7.3E-04 | 3.8E-10 | 3 |
| Sh07F01-62 | 3.9E+06 | 1.4E-03 | 3.6E-10 | 2 |
| Sh07F01-69 | 2.3E+06 | 1.2E-03 | 5.6E-10 | 2 |
| Sh07F01-76 | 2.3E+06 | 1.3E-03 | 5.7E-10 | 2 |
| Sh07F01-83 | 2.6E+06 | 1.4E-03 | 5.4E-10 | 2 |
| Sh29B06-1 | 6.7E+05 | 7.6E-04 | 1.1E-09 | 3 |
| Sh29B06-9 | 8.7E+05 | 2.2E-04 | 2.6E-10 | 1 |
| Sh29B06-23 | 7.8E+05 | 4.8E-04 | 6.4E-10 | 4 |
| Sh29B06-25 | | No Binding | | |

The results in Table 20 demonstrate that the chimeric and each of the humanized antibodies, except Sh29B06-25, have fast association rates ($k_a$), very slow disassociation rates ($k_d$) and very high affinities ($K_D$). In particular, the antibodies have affinities ranging from about 260 pM to about 1.1 nM. No binding was observed for Sh29B06-25. Because Sh29B06-25 does not bind rhRON SEMA+PSI and Sh29B06-23 does, one or more of the back mutations present in the heavy chain of Sh29B06-23 appear to be required for binding with high affinity.

The binding affinities and kinetics of certain purified monoclonal antibodies were also determined. To further characterize certain antibodies, the surface plasmon resonance experiments described above were conducted using concentrations of rhRON SEMA+PSI between 0.3125 nM and 10.0 nM (a 2-fold serial dilution).

The kinetic values of certain purified monoclonal antibodies (i.e., Sh07F01-62 and Sh29B06-78) on rhRON SEMA+PSI at 25° C. and 37° C. are summarized in Table 21.

TABLE 21

Antibody Binding to rhRON SEMA + PSI

| Antibody | Measurements at 25° C. | | | | Measurements at 37° C. | | | |
|---|---|---|---|---|---|---|---|---|
| | ka (1/Ms) | kd (1/s) | KD (M) | n | ka (1/Ms) | kd (1/s) | KD (M) | n |
| Sh07F01-2 | 1.2E+06 | 9.8E−05 | 8.2E−11 | 9 | 1.7E+06 | 5.3E−04 | 3.1E−10 | 9 |
| Sh07F01-43 | 1.2E+06 | 1.1E−04 | 9.0E−11 | 3 | 1.8E+06 | 5.6E−04 | 3.0E−10 | 3 |
| Sh07F01-62 | 1.8E+06 | 1.6E−04 | 8.5E−11 | 4 | 2.8E+06 | 6.9E−04 | 2.5E−10 | 4 |
| Sh07F01-69 | 1.1E+06 | 1.4E−04 | 1.2E−10 | 2 | 2.5E+06 | 7.8E−04 | 3.0E−10 | 2 |
| Sh07F01-76 | 9.8E+05 | 1.3E−04 | 1.3E−10 | 2 | 2.4E+06 | 7.9E−04 | 3.3E−10 | 2 |
| Sh07F01-83 | 1.6E+06 | 1.8E−04 | 1.1E−10 | 2 | 3.2E+06 | 7.9E−04 | 2.4E−10 | 2 |
| Sh29B06-1 | 5.3E+05 | 2.0E−04 | 3.6E−10 | 6 | 8.2E+05 | 7.0E−04 | 8.6E−10 | 5 |
| Sh29B06-23 | 6.7E+05 | 9.5E−05 | 1.4E−10 | 4 | 7.3E+05 | 3.3E−04 | 4.6E−10 | 5 |
| Sh29B06-78 | 7.5E+05 | 3.9E−05 | 5.2E−11 | 7 | 1.0E+06 | 1.1E−04 | 1.1E−10 | 9 |

The results in Table 21 demonstrate the purified antibodies have affinities ranging from about 52 pM to 360 pM when tested at 25° C. or about 110 pM to about 860 pM when tested at 37° C.

Binding to cell surface human wild-type RON and the delta 160 RON variant by antibodies 07F01, Sh07F01-62, 29B06, and Sh29B06-78 was measured at 4° C., using Fluorescence Activated Cell Sorting (FACS). PC3 cells expressing the human wild-type RON, and HT29 cells expressing the delta 160 variant, were harvested using cell dissociation buffer (Invitrogen), washed twice with FACS buffer (PBS with 0.5% BSA), and treated 10 minutes with Cyto Q Antibody diluent and FC receptor block (Innovex Biosciences, Richmond, Calif.). Purified antibodies were diluted in FACS buffer over a concentration range from 0.01 nM to 25 nM. Cells were incubated with 100 µl of antibody for one hour, washed with FACS buffer three times, and incubated for 45 minutes with goat anti-mouse PE-conjugated antibody (Jackson ImmunoResearch Laboratories, West Grove, Pa.) or donkey anti-human PE-conjugated antibody (Jackson ImmunoResearch Laboratories, West Grove, Pa.). Cells were washed three times with FACS buffer, resuspended in 300 µl of FACS buffer, and analyzed using a Beckman Coulter Cytomics FC 500 FACS instrument. All four antibodies were compared in the same experiment. Results are summarized in Table 22.

TABLE 22

| | 07F01 | Sh07F01-62 | 29B06 | Sh29B06-78 |
|---|---|---|---|---|
| Human RON - $K_D$ (nM) | 0.053 | 0.043 | 0.136 | 0.090 |

TABLE 22-continued

| | 07F01 | Sh07F01-62 | 29B06 | Sh29B06-78 |
|---|---|---|---|---|
| Human RON - $K_D$ range (nM) | 0.036 to 0.069 | 0.026 to 0.060 | 0.083 to 0.190 | 0.063 to 0.117 |
| Delta 160 RON - $K_D$ (nM) | 0.100 | 0.118 | 0.167 | 0.239 |
| Delta 160 RON - $K_D$ range (nM) | 0.071 to 0.129 | 0.045 to 0.191 | 0.066 to 0.267 | 0.202 to 0.277 |

The results in Table 22 demonstrate that the humanized antibodies Sh07F01-62 and Sh29B06-78 retain their ability to bind both wild-type RON and the delta 160 RON variant on the cell surface with affinities equivalent to their murine antibody counterparts (i.e., 07F01 and 29B06, respectively).

C. Comparison of Other Anti-RON Antibodies

Three antibodies that inhibit the function of human RON were constructed and expressed using published information. One antibody, referred to as 1P3B2-BIIB Ab, was constructed based on the disclosure of Huet et al., U.S. Patent Publication No. 2009/0226442 (Biogen Idec, Inc.). Two additional antibodies, referred to as RON6 and RON8, were constructed based on the disclosure of Pereira et al., U.S. Patent Publication No. 2009/0136510 (Imclone Systems, Inc.).

Kinetic parameters for the 1P3B2-BIIB Ab, RON6, and RON8 antibodies on rhRON SEMA+PSI at 25° C. and 37° C. were determined by Biacore as described above (See Section B. Binding Affinities of Humanized and Chimeric Anti-RON Monoclonal Antibodies). The kinetic values for each antibody are summarized in Table 23.

TABLE 23

Antibody Binding to rhRON SEMA + PSI

| Antibody | Measurements at 25° C. | | | | Measurements at 37° C. | | | |
|---|---|---|---|---|---|---|---|---|
| | ka (1/Ms) | kd (1/s) | KD (M) | n | ka (1/Ms) | kd (1/s) | KD (M) | n |
| Sh29B06-78 | 6.8E+05 | 3.1E−05 | 4.8E−11 | 6 | 9.6E+05 | 1.0E−04 | 1.1E−10 | 8 |
| Sh07F01-62 | 1.8E+06 | 1.6E−04 | 8.5E−11 | 4 | 2.8E+06 | 6.9E−04 | 2.5E−10 | 4 |
| 1P3B2-BIIB | 1.5E+06 | 1.2E−03 | 8.0E−10 | 1 | 2.2E+07 | 2.6E−02 | 1.2E−09 | 1 |
| RON6 | 2.3E+06 | 2.6E−03 | 1.1E−09 | 1 | 1.9E+10 | 1.9E−01 | 1.0E−09 | 1 |
| RON8 | 1.2E+06 | 6.8E−04 | 6.7E−10 | 3 | 7.0E+06 | 2.5E−03 | 9.2E−10 | 3 |

The results in Table 23 demonstrate that the overall equilibrium dissociation constant ($K_D$) for Sh29B06-78 and Sh07F01-62 were smaller (i.e., higher affinity) than the $K_D$ for 1P3B2-BIIB, RON6, and RON8 at both 25° C. and 37° C. The $K_D$ of 1P3B2-BIIB, RON6, and RON8 antibodies can also be compared with other humanized 29B06 or 07F01 variants by comparing Tables 21 and 23.

Therefore, the binding affinities of Sh29B06-78 and Sh07F01-62 are significantly higher than the affinities of 1P3B2-BIIB, RON6, and RON8 antibodies as disclosed herein.

Example 15

Inhibition of MSP-RON Binding

The chimeric and humanized antibodies produced in Example 14 were tested for inhibition of MSP binding to hRON SEMA+PSI, as measured by electrochemiluminescence (ECL) assay as described in Example 3. The antibodies (concentration range: 0.006-10 µg/mL) were incubated for 45 minutes at room temperature.

The MSP-hRON binding interaction was inhibited by the chimeric and humanized antibodies listed in Table 24, which were tested in this assay. The $IC_{50}$ for the antibodies (IgG1) are shown in Table 24.

TABLE 24

| Antibody | Mean $IC_{50}$ | Std Dev of $IC_{50}$ | N |
|---|---|---|---|
| Sh29B06-1 | 1.73 | 1.24 | 8 |
| Sh29B06-23 | 1.24 | 1.57 | 9 |
| Sh29B06-78 | 0.41 | 0.24 | 8 |
| Sh07F01-2 | 0.91 | 1.42 | 8 |
| Sh07F01-43 | 0.22 | 0.09 | 2 |
| Sh07F01-62 | 0.32 | 0.12 | 6 |
| Sh07F01-69 | 0.28 | 0.18 | 2 |
| Sh07F01-76 | 0.38 | 0.33 | 2 |
| Sh07F01-83 | 0.33 | 0.24 | 2 |

The results in Table 24 demonstrate that the chimeric and humanized anti-RON antibodies listed in Table 24 (i.e., Sh29B06-1, Sh29B06-23, Sh29B06-78, Sh07F01-2, Sh07F01-43, Sh07F01-62, Sh07F01-69, Sh07F01-76, and Sh07F01-83) retain the ability to block MSP binding to hRON SEMA+PSI with high potency.

Example 16

Inhibition of Downstream Signaling by Anti-RON Antibodies

The chimeric and humanized anti-RON antibodies produced in Example 14 were tested for their ability to inhibit MSP-induced phosphorylation of ERK, a RON downstream signaling molecule, using the cell-based assay described in Example 3. The antibodies (concentration range: 0.006-10 µg/mL) in RPMI were added to the cells and incubated for one hour at 37° C. The IC50s of ERK phosphorylation inhibition by the chimeric and humanized anti-RON antibodies tested in this assay are shown in Table 25.

TABLE 25

| Antibody | Mean $IC_{50}$ | Std Dev of $IC_{50}$ | N |
|---|---|---|---|
| Sh29B06-1 | 0.10 | 0.10 | 6 |
| Sh29B06-23 | 0.11 | 0.08 | 10 |

TABLE 25-continued

| Antibody | Mean $IC_{50}$ | Std Dev of $IC_{50}$ | N |
|---|---|---|---|
| Sh29B06-78 | 0.13 | 0.08 | 5 |
| Sh07F01-2 | 0.06 | 0.06 | 7 |
| Sh07F01-43 | 0.02 | 0.00 | 3 |
| Sh07F01-62 | 0.03 | 0.03 | 2 |
| Sh07F01-69 | 0.05 | 0.02 | 2 |
| Sh07F01-76 | 0.10 | 0.03 | 2 |
| Sh07F01-83 | 0.03 | 0.02 | 2 |

The results in Table 25 demonstrate that the chimeric and humanized anti-RON antibodies listed in Table 25 (i.e., Sh29B06-1, Sh29B06-23, Sh29B06-78, Sh07F01-2, Sh07F01-43, Sh07F01-62, Sh07F01-69, Sh07F01-76, and Sh07F01-83) inhibit MSP-induced ERK phosphorylation in T47D breast cancer cell line with high potency.

Example 17

Inhibition of MSP-Dependent Cell Migration

Figure 16:
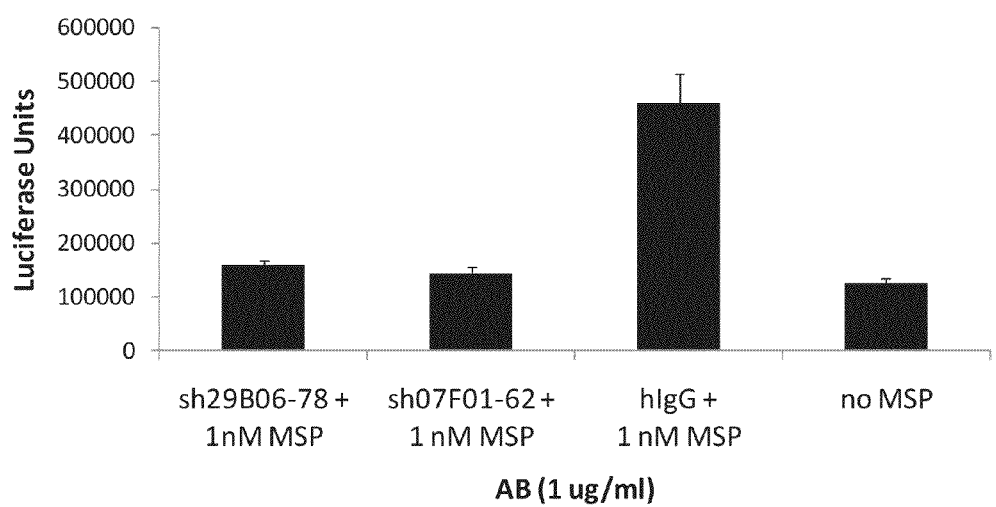
FIG. 16 is a histogram summarizing results from an experiment measuring inhibition of MSP induced HPAF-II cell migration by anti-RON antibodies Sh29B06-78 and Sh07F01-62, an IgG negative control (human IgG), and a no MSP control by transwell assay.

Humanized antibodies sh29B06-78 and sh07F01-62 as produced in Example 14 were tested for their ability to inhibit MSP-induced cell migration as described in Example 10. In this example, antibodies were added at a concentration of 1 µg/ml and serially diluted at a 1:5 dilution, and cells were incubated for 2 hours. Percent inhibition was determined by the following formula: 100−(anti-RON antibody treated-baseline)/(control huIgG treated-baseline)*100. Results on inhibition of MSP-induced HPAF-II cell migration by anti-RON antibodies, sh29B06-78 and sh07F01-62, are summarized in Table 26 and FIG. 16.

TABLE 26

| AB concentration | sh29B06-78 | | sh07F01-62 | |
|---|---|---|---|---|
| ng/ml | AVG | Std DEV | AVG | Std DEV |
| 1000.00 | 94.82 | 3.34 | 98.96 | 3.79 |
| 200.00 | 90.67 | 2.37 | 97.80 | 1.12 |
| 40.00 | 59.85 | 12.50 | 67.18 | 7.67 |
| 8.00 | 59.71 | 2.87 | 37.22 | 4.16 |
| 1.60 | 63.95 | 20.15 | 38.91 | 13.79 |
| 0.32 | 42.03 | 39.88 | 43.27 | 5.76 |
| 0.06 | 60.37 | 11.92 | 34.40 | 2.31 |

The results in Table 26 demonstrate that humanized anti-RON antibodies, sh29B06-78 and sh07F01-62, potently inhibit MSP-induced cell migration in HPAF-II pancreatic cancer cell lines.

Example 18

Inhibition of MSP-Induced Cell Invasion

Humanized antibodies sh29B06-78 and sh07F01-62 as produced in Example 14 were tested for their ability to inhibit MSP-induced cell invasion. HPAF-II pancreatic cancer cells were trypsinized, counted, and placed at a concentration of 50,000/well in 45 µl of 10% FBS/MEM in the upper chamber of a BD 96-well BD BIOCOAT™ MATRIGEL™ invasion FLUOROBLOK™ plate (Becton Dickinson). Antibodies were added at a concentration of 30 µg/ml and cells were incubated for 2 hours. The bottom chamber contained 10% FBS MEM (2000 and 1 nM MSP, and cells were incubated for 24 hours. The number of cells that underwent invasion through the membrane was determined by the addition of Calcien Dye at 4 μg/ml final concentration to the bottom chamber, followed by a one-hour incubation. Fluorescence intensity was measured using a WALLAC 1420 VICTOR™ instrument. Results on inhibition of MSP-induced HPAFII cell invasion by anti-RON antibodies are summarized in FIG. 17.

Figure 17:
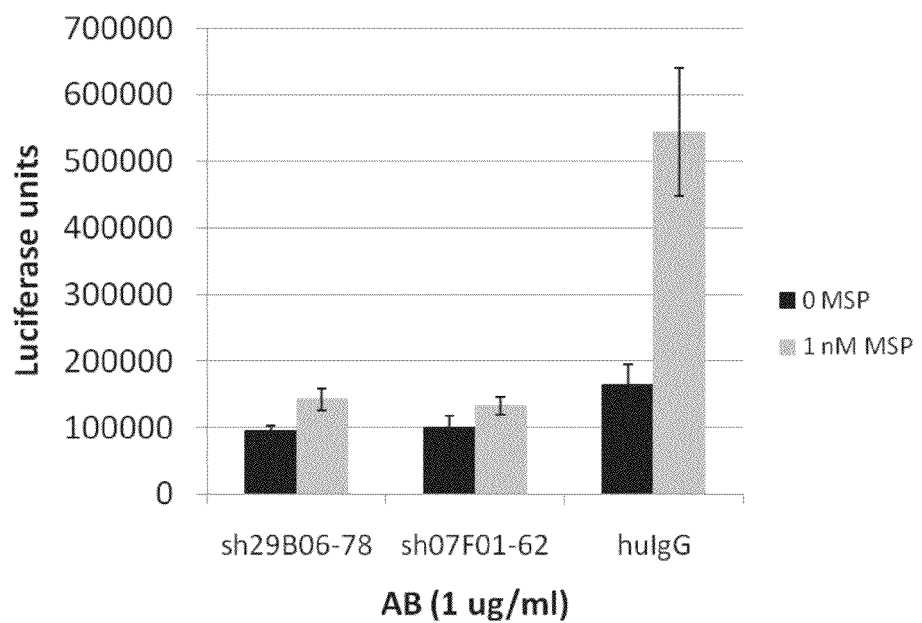
FIG. 17 is a histogram summarizing results from an experiment measuring inhibition of MSP induced HPAF-II cell invasion by anti-RON antibodies Sh29B06-78 and Sh07F01-62 and an IgG negative control (human IgG) at 0 and 1 nM MSP.

The results in FIG. 17 demonstrate that humanized anti-RON antibodies sh29B06-78 and sh07F01-6 potently inhibit MSP-dependent cell invasion in HPAF-II pancreatic cancer cell line.

Example 19

Inhibition of Growth of NCI-H358 Lung Xenograft Tumor Model

Figure 18:
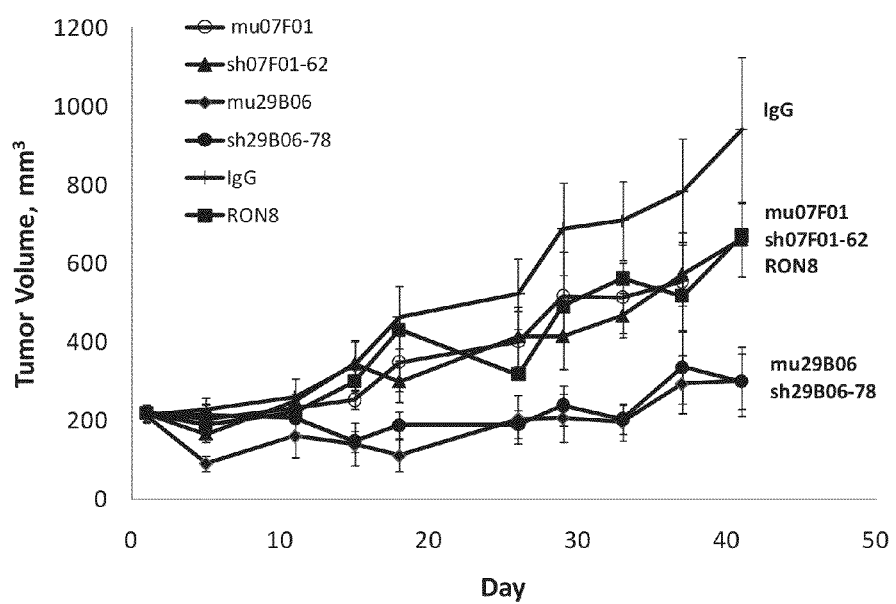
FIG. 18 is a graph summarizing data on inhibition of growth of an NCI-H358 xenograft tumor model by anti-RON antibodies mu07F01 (○), Sh07F01-62 (▲), mu29B06 (♦), RON8 (■), and Sh29B06-78 (●), and a human IgG control (+).

Inhibition of tumor growth by the humanized anti-RON antibodies was tested in an NCI-H358 lung xenograft model. The NCI-H358 cells (ATCC) were grown in culture at 37° C. in an atmosphere containing 5% $CO_2$, using RMPI medium (Invitrogen) containing 10% FBS. Cells were inoculated subcutaneously into the flank of 8-week old female CB.17 SCID mice (Taconic Labs) with $5\times10^6$ cells per mouse in 50% matrigel (Becton Dickinson). Tumor measurements were taken twice weekly using vernier calipers. When tumors reached approximately 150 $mm^3$, the mice were randomized into six groups of ten mice each. Each group received one of the following treatments: human IgG (huIgG) control, mu29B06, sh29B06-78, mu07F01, sh07F01-62 and RON8. Treatment was administered by intra-peritoneal injection two times per week at 10 mg/kg for seven weeks. Treatment was well-tolerated, with no significant loss in body weight. Tumor growth inhibition is expressed as percent inhibition (baseline subtracted) to the huIgG control and statistical analysis was conducted using ANOVA. Results for tumor growth inhibition on day 41 in the NCI-H358 model are shown in FIG. 18 and Table 27.

TABLE 27

| Treatment | TGI % | ANOVA (compared to huIgG) |
|---|---|---|
| mu29B06 | 88.93 | P < 0.01 |
| sh29B06-78 | 89.02 | P < 0.01 |
| mu07F01 | 34.15 | P > 0.05 |
| sh07F01-62 | 39.05 | P > 0.05 |
| RON8 | 37.99 | P > 0.05 |

Anti-RON antibody treatments resulted in tumor growth inhibition compared to huIgG control. Specifically, mu29B06 antibody treatment resulted in tumor growth inhibition of 89% (P<0.01); sh29B06-78 antibody treatment resulted in tumor growth inhibition of 89% (P<0.01); mu07F01 antibody treatment resulted in tumor growth inhibition of 34% (P>0.05); sh07F01-62 antibody treatment resulted in tumor growth inhibition of 39% (P>0.05); and RON8 antibody treatment resulted in tumor growth inhibition of 38% (P>0.05). These results demonstrate that sh29B06-78 and mu29B06 inhibit tumor growth in a NCI-H358 xenograft model (P<0.01), whereas the mu07F01, sh07F01-62, and RON8 antibodies did not inhibit tumor growth in this model (P>0.05, which is not statically significant).

Example 20

RON Receptor Degradation

Western blots were performed to determine total levels of RON receptor at the end of treatment. Four tumor samples from each of the treatment groups were weighed, lysed in RIPA buffer (Boston Bioproducts), 1 mM EDTA (Boston Bioproducts), 1 mM Sodium OrthoVandadate (Sigma), 1× protease inhibitor (Sigma) and 1× Phosphatase Inhibitor I and II (Sigma). The samples were homogenized using a hand-held electric homogenizer and incubated for 10 minutes on ice. Samples are spun down at 11,000 RPM for 30 minutes at 4° C. Supernatants were collected and protein concentrations were determined using Pierce BCA™ assay kit according to the manufacturers protocol. The C-20 (Santa Cruz) antibody was used to detect total RON protein. β-tubulin (Cell Signaling Technologies) was blotted as loading control. The Western blots were blocked for one hour in 5% Milk in 1×TBST (TBS-0.1% TWEEN™) (Sigma), followed by primary antibody incubation over night at 4° C. in 5% BSA 1×TBST at 1:1000 for both antibodies. Western blots were washed three times with 1×TBST, incubated with anti-rabbit HRP conjugated secondary antibody (Cell Signaling Technologies), for one hour at room temperature. Western blots were washed three times with 1×TBST and then developed using Dura Signal (Pierce).

Figure 19:
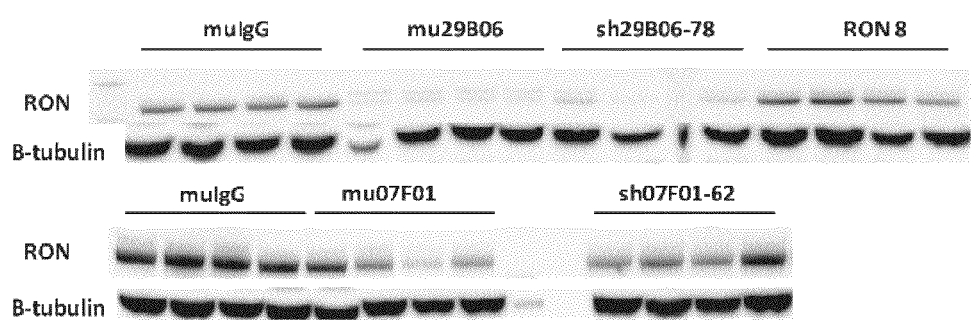
FIG. 19 depicts Western blots summarizing results from an experiment measuring RON receptor degradation by anti-RON antibodies mu07F01, Sh07F01-62, mu29B06, RON8, and Sh29B06-78.

The results in FIG. 19 demonstrate RON receptor degradation in the mu29B06 and sh29B06-78 treated samples and to a lesser extent in the mu07F01 and sh07F01-62 treated samples. RON receptor degradation was not observed in the RON8 treated samples.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

What is claimed is:

1. An isolated antibody that binds human RON (Recepteur d'Origine Natais), comprising:
   (i) an immunoglobulin heavy chain variable region comprising a $CDR_{H1}$ comprising an amino acid sequence selected from the group consisting of SEQ ID NO: 5 and SEQ ID NO: 124, a $CDR_{H2}$ comprising the amino acid sequence of SEQ ID NO: 122, and a $CDR_{H3}$ comprising the amino acid sequence of SEQ ID NO: 123; and
   (ii) an immunoglobulin light chain variable region comprising a $CDR_{L1}$ comprising the amino acid sequence of SEQ ID NO: 130, a $CDR_{L2}$ comprising the amino acid sequence of SEQ ID NO: 131, and a $CDR_{L3}$ comprising the amino acid sequence of SEQ ID NO: 10.

2. The antibody of claim 1, wherein the immunoglobulin heavy chain variable region comprises a $CDR_{H1}$ comprising the amino acid sequence of SEQ ID NO: 5, a $CDR_{H2}$ comprising the amino acid sequence of SEQ ID NO: 122, and a $CDR_{H3}$ comprising the amino acid sequence of SEQ ID NO: 123; and
   the immunoglobulin light chain variable region comprises a $CDR_{L1}$ comprising the amino acid sequence of SEQ ID NO: 130, a $CDR_{L2}$ comprising the amino acid sequence of SEQ ID NO: 131, and a $CDR_{L3}$ comprising the amino acid sequence of SEQ ID NO: 10.

3. The antibody of claim 1, wherein the CDR sequences are interposed between human framework sequences.

4. The antibody of claim 1, wherein the immunoglobulin heavy chain variable region comprises a $CDR_{H1}$ comprising the amino acid sequence of SEQ ID NO: 124, a $CDR_{H2}$ comprising the amino acid sequence of SEQ ID NO: 122, and a $CDR_{H3}$ comprising the amino acid sequence of SEQ ID NO: 123; and
   the immunoglobulin light chain variable region comprises a $CDR_{L1}$ comprising the amino acid sequence of SEQ ID NO: 130, a CDR$_{L2}$ comprising the amino acid sequence of SEQ ID NO: 131, and a CDR$_{L3}$ comprising the amino acid sequence of SEQ ID NO: 10.

5. The antibody of claim 1, wherein the antibody is an antigen-binding fragment.

6. The antibody of claim 1, wherein the immunoglobulin heavy chain variable region comprises the amino acid sequence of SEQ ID NO: 137 and the immunoglobulin light chain variable region comprises the amino acid sequence of SEQ ID NO: 139.

7. The antibody of claim 1, wherein the immunoglobulin heavy chain comprises the amino acid sequence of SEQ ID NO: 166, and the immunoglobulin light chain comprises the amino acid sequence of SEQ ID NO: 168.

8. The antibody of claim 1, wherein the antibody binds human RON with a $K_D$ of 900 pM or lower as measured by surface plasmon resonance.

9. The antibody of claim 8, wherein the antibody binds human RON with a $K_D$ of 500 pM or lower as measured by surface plasmon resonance.

10. The antibody of claim 9, wherein the antibody binds human RON with a $K_D$ of 250 pM or lower as measured by surface plasmon resonance.

11. The antibody of claim 1, wherein the CDR sequences are interposed between humanized framework sequences.

* * * * *

SEQUENCE LISTING

<160> NUMBER OF SEQ ID NOS: 178

<210> SEQ ID NO 1
<211> LENGTH: 363

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gaggtgaagc ttctcgagtc tggaggtggc ctggtgcagc cgggtggatc cctgaaactc     60
tcctgtgcag cctcaggatt cgattttagt agacactgga tgagttgggt ccggctggct    120
ccagggaaag ggctagaatg gatcgcagaa attaatccag atagcagaac gataaactat    180
acgccatctc taaaggagaa attcatcatc tccagagaca acgccaaaaa ttcgctgttt    240
ctgcaaatga acagagtgag atctgaggac acagcccttt attactgtgc aagacgggta    300
agaattcatt actacggcgc tatggactgc tggggtcaag aacctcagt caccgtctcc    360 tca                                                                  363

<210> SEQ ID NO 2
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg His
            20                  25                  30

Trp Met Ser Trp Val Arg Leu Ala Pro Gly Lys Gly Leu Glu Trp Ile
        35                  40                  45

Ala Glu Ile Asn Pro Asp Ser Arg Thr Ile Asn Tyr Thr Pro Ser Leu
    50                  55                  60

Lys Glu Lys Phe Ile Ile Ser Arg Asp Asn Ala Lys Asn Ser Leu Phe
65                  70                  75                  80

Leu Gln Met Asn Arg Val Arg Ser Glu Asp Thr Ala Leu Tyr Tyr Cys
                85                  90                  95

Ala Arg Arg Val Arg Ile His Tyr Tyr Gly Ala Met Asp Cys Trp Gly
            100                 105                 110

Gln Gly Thr Ser Val Thr Val Ser Ser
        115                 120

<210> SEQ ID NO 3
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gacattgtgt tgacccagtc tcaaaaaatc gtgtccacat cagtaggagc cagggtcagc     60
gtcacctgca aggccagtca gaatgtgggt tctagtttag tctggtatca acagaaacca    120
ggtcaatctc ctaaaacact gatttactcg gcatccttcc ggtacagtgg agtccctgat    180
cgcttcacag gcagtggatc tgggacagat ttcactctca ccatcagcaa tgtgcagtct    240
gaagacttgg cagattattt ctgtcaacaa tataataact atccgctcac gttcggtgct    300
gggaccaagc tggagctgaa a                                               321
```

```
<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Val Leu Thr Gln Ser Gln Lys Ile Val Ser Thr Ser Val Gly
1               5                   10                  15

Ala Arg Val Ser Val Thr Cys Lys Ala Ser Gln Asn Val Gly Ser Ser
            20                  25                  30

Leu Val Trp Tyr Gln Gln Lys Pro Gly Gln Ser Pro Lys Thr Leu Ile
        35                  40                  45

Tyr Ser Ala Ser Phe Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Asn Tyr Pro Leu
                85                  90                  95

Thr Phe Gly Ala Gly Thr Lys Leu Glu Leu Lys
            100                 105

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg His Trp Met Ser
1               5

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Ile Asn Pro Asp Ser Arg Thr Ile Asn Tyr Thr Pro Ser Leu Lys
1               5                   10                  15

Glu

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Val Arg Ile His Tyr Tyr Gly Ala Met Asp Cys
1               5                   10

<210> SEQ ID NO 8
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Ala Ser Gln Asn Val Gly Ser Ser Leu Val
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Ala Ser Phe Arg Tyr Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Gln Tyr Asn Asn Tyr Pro Leu Thr
1               5

<210> SEQ ID NO 11
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gaggtgcagt tagtggagtc tgggggaggc ttagtgaagc ctggagggtc cctgaaactc      60
tcctgtgcag cctctggatt cactttcagt acctatgcca tgtcttggat tcgccagact     120
ccggagaaga ggctggagtg ggtcgcagga atcactaatg gtggtagttt cacctactat     180
ccagacactg tgaagggacg attcaccatc tccagagaca tgccaggaa catcctatac      240 ctgcaaatga gcggtctgag gtctgaggac acggccatgt attattgtgc aagacagggt     300
tactatggtg ttaactttga ctactggggc caaggcacca ctctcacagt ctcctca       357

<210> SEQ ID NO 12
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30
```

```
Ala Met Ser Trp Ile Arg Gln Thr Pro Glu Lys Arg Leu Glu Trp Val
            35                  40                  45

Ala Gly Ile Thr Asn Gly Gly Ser Phe Thr Tyr Tyr Pro Asp Thr Val
 50                  55                  60

Lys Gly Arg Phe Thr Ile Ser Arg Asp Asn Ala Arg Asn Ile Leu Tyr
 65                  70                  75                  80

Leu Gln Met Ser Gly Leu Arg Ser Glu Asp Thr Ala Met Tyr Tyr Cys
                85                  90                  95

Ala Arg Gln Gly Tyr Tyr Gly Val Asn Phe Asp Tyr Trp Gly Gln Gly
            100                 105                 110

Thr Thr Leu Thr Val Ser Ser
            115

<210> SEQ ID NO 13
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gatgctgtga tgacccaaac tccactctcc ctgcctgtca gtcttggaga tcaagcctcc      60
atctcttgca ggtctagtca gagccttgaa acagtaacg gaaacactta tttgaactgg     120
tacctccaga aaccaggcca gtctccacag ctcctgatct acagggtttc caaccgattt     180
tctggggtcc cagacaggtt cagtggtagt ggatcaggga cagatttcac actgaaaatc    240
atcagagtgg aggctgagga tttgggactt tatttctgcc tccaagttac acatgtcccg    300
cacacgttcg gagggggac caaactggaa ttaaaa                              336

<210> SEQ ID NO 14
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ala Val Met Thr Gln Thr Pro Leu Ser Leu Pro Val Ser Leu Gly
  1               5                  10                  15

Asp Gln Ala Ser Ile Ser Cys Arg Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ile Arg Val Glu Ala Glu Asp Leu Gly Leu Tyr Phe Cys Leu Gln Val
                85                  90                  95

Thr His Val Pro His Thr Phe Gly Gly Gly Thr Lys Leu Glu Leu Lys
            100                 105                 110

<210> SEQ ID NO 15
<211> LENGTH: 5
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 15

Thr Tyr Ala Met Ser
1               5

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Ile Thr Asn Gly Gly Ser Phe Thr Tyr Tyr Pro Asp Thr Val Lys
1               5                   10                  15

Gly

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Gly Tyr Tyr Gly Val Asn Phe Asp Tyr
1               5                   10

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ser Ser Gln Ser Leu Glu Asn Ser Asn Gly Asn Thr Tyr Leu Asn
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Val Ser Asn Arg Phe Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Gln Val Thr His Val Pro His Thr

<210> SEQ ID NO 21
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
gaagtgaagc tggtggagtc gggggggaggc ttagtgaagc ctggagcgtc tctgaaactc     60
tcctgtgcag cctctggatt cattttcagt tcctatggca tgtcttgggt tcgccagact    120
tcagacaaga ggctggagtg ggtcgcttcc attagtagtg gtggtggtac cacctactat    180
ctagacactg taaagggccg attcaccatc tccagagaga tgccaagga caccctgtac    240 ctgcaaatga gtggtctgaa gtctgaagac acggccttgt attactgtac aagaggccaa    300
tggttactaa agtttgctta ctggggccaa gggactctgg tcactgtctc tgca          354

<210> SEQ ID NO 22
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Lys Leu Val Glu Ser Gly Gly Gly Leu Val Lys Pro Gly Ala
1               5                   10                  15

Ser Leu Lys Leu Ser Cys Ala Ala Ser Gly Phe Ile Phe Ser Ser Tyr
            20                  25                  30

Gly Met Ser Trp Val Arg Gln Thr Ser Asp Lys Arg Leu Glu Trp Val
        35                  40                  45

Ala Ser Ile Ser Ser Gly Gly Thr Thr Tyr Tyr Leu Asp Thr Val
    50                  55                  60

Lys Gly Arg Phe Thr Ile Ser Arg Glu Asn Ala Lys Asp Thr Leu Tyr
65                  70                  75                  80

Leu Gln Met Ser Gly Leu Lys Ser Glu Asp Thr Ala Leu Tyr Tyr Cys
                85                  90                  95

Thr Arg Gly Gln Trp Leu Leu Lys Phe Ala Tyr Trp Gly Gln Gly Thr
            100                 105                 110

Leu Val Thr Val Ser Ala
        115

<210> SEQ ID NO 23
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
caacttgtgc tcactcagtc atcttcagcc tctttctccc tgggagcctc agcaaaactc     60
acgtgcacct tgagtagtca gcacactacg taccaccattg aatggtatca gcaactgcca   120
ctcaagcctc ctaagtatgt gatggagctt aagaaagatg gaagccacag cacaggtgtt    180
gggattcctg atcgcttctc tggatccagc tctggtgctg atcgctacct taccatttcc    240

```
aacatccagc ctgaagatga agcaatatac atctgtggtg tgggtgagac aattgaggac      300
caatttgtgt atgttttcgg cggtggcacc aaggtcactg tccta                     345
```

```
<210> SEQ ID NO 24
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24
```

Gln Leu Val Leu Thr Gln Ser Ser Ala Ser Phe Ser Leu Gly Ala
1               5                   10                  15

Ser Ala Lys Leu Thr Cys Thr Leu Ser Ser Gln His Thr Thr Tyr Thr
            20                  25                  30

Ile Glu Trp Tyr Gln Gln Leu Pro Leu Lys Pro Pro Lys Tyr Val Met
        35                  40                  45

Glu Leu Lys Lys Asp Gly Ser His Ser Thr Gly Val Gly Ile Pro Asp
    50                  55                  60

Arg Phe Ser Gly Ser Ser Ser Gly Ala Asp Arg Tyr Leu Thr Ile Ser
65                  70                  75                  80

Asn Ile Gln Pro Glu Asp Glu Ala Ile Tyr Ile Cys Gly Val Gly Glu
                85                  90                  95

Thr Ile Glu Asp Gln Phe Val Tyr Val Phe Gly Gly Gly Thr Lys Val
            100                 105                 110

Thr Val Leu
        115

```
<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25
```

Ser Tyr Gly Met Ser
1               5

```
<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26
```

Ser Ile Ser Ser Gly Gly Gly Thr Thr Tyr Tyr Leu Asp Thr Val Lys
1               5                   10                  15

Gly

```
<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27
```

```
Gly Gln Trp Leu Leu Lys Phe Ala Tyr
1               5
```

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Thr Leu Ser Ser Gln His Thr Thr Tyr Thr Ile Glu
1               5                   10
```

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Leu Lys Lys Asp Gly Ser His Ser Thr Gly Val
1               5                   10
```

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Gly Val Gly Glu Thr Ile Glu Asp Gln Phe Val Tyr Val
1               5                   10
```

<210> SEQ ID NO 31
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
gaggtgcagc ttcaggagtc aggacctagc ctcgtgaaac cttctcagac tctgtccctc      60
acctgttatg tcactggcga ctccatcacc agtgattact ggaattggat ccggaaattc     120
ccaggaaata aacttgagta catgggatat atcagctaca gtggtagcac ttactacaat     180
ccatctctca aaagtcgaat ctccatcact cgagacacat ccaagaacca gttctacctt     240
cggttgaatt ctgtgactac tgaggacaca gccacatatt actgtgcaag aacccatata     300
cttacgattg cttactgggg ccaagggact ctggtcactg tctctgca                  348
```

<210> SEQ ID NO 32
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Gln Glu Ser Gly Pro Ser Leu Val Lys Pro Ser Gln
1               5                   10                  15

Thr Leu Ser Leu Thr Cys Tyr Val Thr Gly Asp Ser Ile Thr Ser Asp
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Ser Thr Tyr Tyr Asn Pro Ser Leu Lys
    50                  55                  60

Ser Arg Ile Ser Ile Thr Arg Asp Thr Ser Lys Asn Gln Phe Tyr Leu
65                  70                  75                  80

Arg Leu Asn Ser Val Thr Thr Glu Asp Thr Ala Thr Tyr Tyr Cys Ala
                85                  90                  95

Arg Thr His Ile Leu Thr Ile Ala Tyr Trp Gly Gln Gly Thr Leu Val
            100                 105                 110

Thr Val Ser Ala
        115

<210> SEQ ID NO 33
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
caggctgttg tgactcagga atctgcactc accacatcac ctggtgaaac agtcacactc       60
acttgtcgct caagtgccgg ggctgttaca actagtaact ttgccaactg ggtccaagaa      120
aaaccagatc atttattcac tggtctaata ggtgatacca acatccgagc tccaggtgtt      180
cctgccagat tctcaggctc cctgattgga gacaaggctg ccctcaccat cacaggggca      240
cagactgagg atgaggcaat atatttctgt gctctttggt acagcaacca ttactgggtg      300
ttcggtggag gaaccaaact gactgtccta                                       330

<210> SEQ ID NO 34
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Ala Val Val Thr Gln Glu Ser Ala Leu Thr Thr Ser Pro Gly Glu
1               5                   10                  15

Thr Val Thr Leu Thr Cys Arg Ser Ser Ala Gly Ala Val Thr Thr Ser
            20                  25                  30

Asn Phe Ala Asn Trp Val Gln Glu Lys Pro Asp His Leu Phe Thr Gly
        35                  40                  45

Leu Ile Gly Asp Thr Asn Ile Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Tyr Trp Val Phe Gly Gly Gly Thr Lys Leu Thr Val Leu
            100                 105                 110

```
<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Asp Tyr Trp Asn
1               5

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Tyr Ile Ser Tyr Ser Gly Ser Thr Tyr Tyr Asn Pro Ser Leu Lys Ser
1               5                   10                  15

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr His Ile Leu Thr Ile Ala Tyr
1               5

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Ser Ser Ala Gly Ala Val Thr Thr Ser Asn Phe Ala Asn
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Thr Asn Ile Arg Ala Pro
1               5

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 40

Ala Leu Trp Tyr Ser Asn His Tyr Trp Val
1               5                   10

<210> SEQ ID NO 41
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
gaggtgcagc ttcaggagtc aggacctagc ctcgtgaaac cttctcagac tctgtccctc      60
acctgttctg tcactggcga ctccatcacc agtggttact ggaactggat ccggaaattc     120
ccagggaata acttgagta catggggtac ataagctaca gtggtaaaac ttactacaat     180
ccatctctca aaagtcgaat ctccatcact cgagacacat ccaagaacca ttactacctg     240
cagttgattt ctgtgactgc tgaggacaca gccacatatt actgtgcaag gtctaagtac     300
gactatgcta tggactactg gggtcaagga acctcagtca ccgtctcctc a              351

<210> SEQ ID NO 42
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Lys Thr Tyr Tyr Asn Pro Ser Leu Lys
    50                  55                  60

Ser Arg Ile Ser Ile Thr Arg Asp Thr Ser Lys Asn His Tyr Tyr Leu
65                  70                  75                  80

Gln Leu Ile Ser Val Thr Ala Glu Asp Thr Ala Thr Tyr Tyr Cys Ala
                85                  90                  95

Arg Ser Lys Tyr Asp Tyr Ala Met Asp Tyr Trp Gly Gln Gly Thr Ser
            100                 105                 110

Val Thr Val Ser Ser
        115

<210> SEQ ID NO 43
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
gacattgtgc tgacccaatc tccagcttct ttggctgtgt ctctaggaca gagggccacc      60
atctcctgca gagccagcga aattgttgat aattttggca ttagttttat gaactggttc     120

```
caacagaaac caggacagcc acccaaactc ctcatctatg ctgcatccaa ccaaggatcc      180
ggggtccctg ccaggtttag tggcagtggg tctgggacag acttcagcct caacatccat      240
cctgtggagg aggatgatac tgcaatgtat ttctgtcagc aaagtaagga ggttcctccg      300
acgttcggtg gaggcaccaa gctggaaatc aaa                                    333
```

```
<210> SEQ ID NO 44
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44
```

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ile Val Asp Asn Phe
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Thr Ala Met Tyr Phe Cys Gln Gln Ser Lys
                85                  90                  95

Glu Val Pro Pro Thr Phe Gly Gly Gly Thr Lys Leu Glu Ile Lys
            100                 105                 110

```
<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45
```

Ser Gly Tyr Trp Asn
1               5

```
<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46
```

Tyr Ile Ser Tyr Ser Gly Lys Thr Tyr Tyr Asn Pro Ser Leu Lys Ser
1               5                   10                  15

```
<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47
```

Ser Lys Tyr Asp Tyr Ala Met Asp Tyr
1               5

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Ala Ser Glu Ile Val Asp Asn Phe Gly Ile Ser Phe Met Asn
1               5                   10                  15

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Ala Ser Asn Gln Gly Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Gln Ser Lys Glu Val Pro Pro Thr
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Phe Asp Phe Ser Arg His
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asn Pro Asp Ser Arg Thr
1               5

<210> SEQ ID NO 53
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 53

Gly Phe Thr Phe Ser Thr Tyr
1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Thr Asn Gly Gly Ser Phe
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Phe Ile Phe Ser Ser Tyr
1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Ser Gly Gly Gly Thr
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Asp Ser Ile Thr Ser Asp
1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Tyr Ser Gly Ser
1               5
```

```
<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Asp Ser Ile Thr Ser Gly
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ser Tyr Ser Gly Lys
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Phe Asp Phe Ser Arg His Trp
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ile Asn Pro Asp Ser Arg Thr Ile
1               5

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala Arg Arg Val Arg Ile His Tyr Tyr Gly Ala Met Asp Cys
1               5                   10

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64
```

```
Gly Phe Thr Phe Ser Thr Tyr Ala
1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ile Thr Asn Gly Gly Ser Phe Thr
1               5

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Arg Gln Gly Tyr Tyr Gly Val Asn Phe Asp Tyr
1               5                   10

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Phe Ile Phe Ser Ser Tyr Gly
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Ser Ser Gly Gly Gly Thr Thr
1               5

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Thr Arg Gly Gln Trp Leu Leu Lys Phe Ala Tyr
1               5                   10

<210> SEQ ID NO 70
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 70

Gly Asp Ser Ile Thr Ser Asp Tyr
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ile Ser Tyr Ser Gly Ser Thr
1               5

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ala Arg Thr His Ile Leu Thr Ile Ala Tyr
1               5                   10

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Asp Ser Ile Thr Ser Gly Tyr
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Ser Tyr Ser Gly Lys Thr
1               5

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Arg Ser Lys Tyr Asp Tyr Ala Met Asp Tyr
1               5                   10
```

```
<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Asn Val Gly Ser Ser
1               5

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Ser Leu Glu Asn Ser Asn Gly Asn Thr Tyr
1               5                   10

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ser Gln His Thr Thr Tyr Thr
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Lys Lys Asp Gly Ser His
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Gly Ala Val Thr Thr Ser Asn Phe
1               5

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 81

Glu Ile Val Asp Asn Phe Gly Ile Ser Phe
1               5                   10

<210> SEQ ID NO 82
<211> LENGTH: 972
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 82

```
gccaaaacga caccccatc tgtctatcca ctggccctg gatctgctgc ccaaactaac      60
tccatggtga ccctgggatg cctggtcaag ggctatttcc ctgagccagt gacagtgacc    120
tggaactctg gatccctgtc cagcggtgtg cacaccttcc cagctgtcct gcagtctgac   180
ctctacactc tgagcagctc agtgactgtc ccctccagca cctggcccag cgagaccgtc   240
acctgcaacg ttgcccaccc ggccagcagc accaaggtgg acaagaaaat tgtgcccagg   300
gattgtggtt gtaagccttg catatgtaca gtcccagaag tatcatctgt cttcatcttc   360
cccccaaagc ccaaggatgt gctcaccatt actctgactc ctaaggtcac gtgtgttgtg   420
gtagacatca gcaaggatga tcccgaggtc cagttcagct ggtttgtaga tgatgtggag   480
gtgcacacag ctcagacgca accccgggag gagcagttca acagcacttt ccgctcagtc   540
agtgaacttc ccatcatgca ccaggactgg ctcaatggca aggagttcaa atgcagggtc   600
aacagtgcag ctttccctgc ccccatcgag aaaaccatct ccaaaaccaa aggcagaccg   660
aaggctccac aggtgtacac cattccacct cccaaggagc agatggccaa ggataaagtc   720
agtctgacct gcatgataac agacttcttc cctgaagaca ttactgtgga gtggcagtgg   780
aatgggcagc cagcggagaa ctacaagaac actcagccca tcatggacac agatggctct   840
tacttcgtct acagcaagct caatgtgcag aagagcaact gggaggcagg aaatactttc   900
acctgctctg tgttacatga gggcctgcac aaccaccata ctgagaagag cctctcccac   960
tctcctggta aa                                                       972
```

<210> SEQ ID NO 83
<211> LENGTH: 324
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

```
Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 84
<211> LENGTH: 990
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
gccaaaacaa cagccccatc ggtctatcca ctggcccctg tgtgtggaga tacaactggc        60
tcctcggtga ctctaggatg cctggtcaag ggttatttcc ctgagccagt gaccttgacc      120
tggaactctg gatccctgtc cagtggtgtg cacaccttcc cagctgtcct gcagtctgac      180
ctctacaccc tcagcagctc agtgactgta acctcgagca cctggcccag ccagtccatc      240
acctgcaatg tggcccaccc ggcaagcagc accaaggtgg acaagaaaat tgagcccaga      300
gggcccacaa tcaagccctg tcctccatgc aaatgcccag cacctaacct cttgggtgga      360
ccatccgtct tcatcttccc tccaaagatc aaggatgtac tcatgatctc cctgagcccc      420
atagtcacat gtgtggtggt ggatgtgagc gaggatgacc cagatgtcca gatcagctgg      480
tttgtgaaca acgtggaagt acacacagct cagacacaaa cccatagaga ggattacaac      540
agtactctcc gggtggtcag tgccctcccc atccagcacc aggactggat gagtggcaag      600
gagttcaaat gcaaggtcaa caacaaagac ctcccagcgc ccatcgagag aaccatctca      660
aaacccaaag ggtcagtaag agctccacag gtatatgtct tgcctccacc agaagaagag      720
```

```
atgactaaga aacaggtcac tctgacctgc atggtcacag acttcatgcc tgaagacatt    780
tacgtggagt ggaccaacaa cgggaaaaca gagctaaact acaagaacac tgaaccagtc    840
ctggactctg atggttctta cttcatgtac agcaagctga gagtggaaaa gaagaactgg    900
gtggaaagaa atagctactc ctgttcagtg gtccacgagg gtctgcacaa tcaccacacg    960
actaagagct ctcccggac tccgggtaaa                                     990
```

<210> SEQ ID NO 85
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 85

```
Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
```

```
                305                 310                 315                 320
Thr Lys Ser Phe Ser Arg Thr Pro Gly Lys
                    325                 330

<210> SEQ ID NO 86
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
cgggctgatg ctgcaccaac tgtatccatc ttcccaccat ccagtgagca gttaacatct      60
ggaggtgcct cagtcgtgtg cttcttgaac aacttctacc ccaaagacat caatgtcaag     120
tggaagattg atggcagtga acgacaaaat ggcgtcctga acagttggac tgatcaggac     180
agcaaagaca gcacctacag catgagcagc accctcacgt tgaccaagga cgagtatgaa     240
cgacataaca gctatacctg tgaggccact cacaagacat caacttcacc cattgtcaag     300
agcttcaaca ggaatgagtg t                                               321

<210> SEQ ID NO 87
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 88
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
ggccagccca agtcttcgcc atcagtcacc ctgtttccac cttcctctga agagctcgag      60
actaacaagg ccacactggt gtgtacgatc actgatttct acccaggtgt ggtgacagtg     120
gactggaagg tagatggtac ccctgtcact cagggtatgg agacaaccca gccttccaaa     180
cagagcaaca acaagtacat ggctagcagc tacctgaccc tgacagcaag agcatgggaa     240
```

```
aggcatagca gttacagctg ccaggtcact catgaaggtc acactgtgga gaagagtttg    300
tcccgtgctg actgttcc                                                  318
```

<210> SEQ ID NO 89
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gly Gln Pro Lys Ser Ser Pro Ser Val Thr Leu Phe Pro Pro Ser Ser
1               5                   10                  15

Glu Glu Leu Glu Thr Asn Lys Ala Thr Leu Val Cys Thr Ile Thr Asp
            20                  25                  30

Phe Tyr Pro Gly Val Val Thr Val Asp Trp Lys Val Asp Gly Thr Pro
        35                  40                  45

Val Thr Gln Gly Met Glu Thr Thr Gln Pro Ser Lys Gln Ser Asn Asn
    50                  55                  60

Lys Tyr Met Ala Ser Ser Tyr Leu Thr Leu Thr Ala Arg Ala Trp Glu
65                  70                  75                  80

Arg His Ser Ser Tyr Ser Cys Gln Val Thr His Glu Gly His Thr Val
                85                  90                  95

Glu Lys Ser Leu Ser Arg Ala Asp Cys Ser
            100                 105

<210> SEQ ID NO 90
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90

```
ggtcagccca agtccactcc cactctcacc gtgtttccac cttcctctga ggagctcaag    60
gaaaacaaag ccacactggt gtgtctgatt ccaactttt ccccgagtgg tgtgacagtg    120
gcctggaagg caaatggtac acctatcacc cagggtgtgg acacttcaaa tcccaccaaa    180
gagggcaaca agttcatggc cagcagcttc ctacatttga catcggacca gtggagatct    240
cacaacagtt ttacctgtca agttacacat gaaggggaca ctgtggagaa gagtctgtct    300
cctgcagaat gtctc                                                     315
```

<210> SEQ ID NO 91
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gly Gln Pro Lys Ser Thr Pro Thr Leu Thr Val Phe Pro Pro Ser Ser
1               5                   10                  15

Glu Glu Leu Lys Glu Asn Lys Ala Thr Leu Val Cys Leu Ile Ser Asn
            20                  25                  30

Phe Ser Pro Ser Gly Val Thr Val Ala Trp Lys Ala Asn Gly Thr Pro
        35                  40                  45

```
Ile Thr Gln Gly Val Asp Thr Ser Asn Pro Thr Lys Glu Gly Asn Lys
         50                  55                  60

Phe Met Ala Ser Ser Phe Leu His Leu Thr Ser Asp Gln Trp Arg Ser
 65                  70                  75                  80

His Asn Ser Phe Thr Cys Gln Val Thr His Glu Gly Asp Thr Val Glu
                 85                  90                  95

Lys Ser Leu Ser Pro Ala Glu Cys Leu
                100                 105
```

<210> SEQ ID NO 92
<211> LENGTH: 1335
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 92

| | |
|---|---:|
| gaggtgaagc ttctcgagtc tggaggtggc ctggtgcagc cgggtggatc cctgaaactc | 60 |
| tcctgtgcag cctcaggatt cgattttagt agacactgga tgagttgggt ccggctggct | 120 |
| ccagggaaag ggctagaatg gatcgcagaa attaatccag atagcagaac gataaactat | 180 |
| acgccatctc taaaggagaa attcatcatc tccagagaca cgccaaaaa ttcgctgttt | 240 |
| ctgcaaatga acagtgag atctgaggac acagcccttt attactgtgc aagacgggta | 300 |
| agaattcatt actacggcgc tatggactgc tggggtcaag aacctcagt caccgtctcc | 360 |
| tcagccaaaa cgacaccccc atctgtctat ccactggccc ctggatctgc tgcccaaact | 420 |
| aactccatgg tgaccctggg atgcctggtc aagggctatt tccctgagcc agtgacagtg | 480 |
| acctggaact ctggatccct gtccagcggt gtgcacacct tcccagctgt cctgcagtct | 540 |
| gacctctaca ctctgagcag ctcagtgact gtcccctcca gcacctggcc cagcgagacc | 600 |
| gtcacctgca acgttgccca ccggccagc agcaccaagg tggacaagaa aattgtgccc | 660 |
| agggattgtg gttgtaagcc ttgcatatgt acagtcccag aagtatcatc tgtcttcatc | 720 |
| ttccccccaa agcccaagga tgtgctcacc attactctga ctcctaaggt cacgtgtgtt | 780 |
| gtggtagaca tcagcaagga tgatcccgag gtccagttca gctggtttgt agatgatgtg | 840 |
| gaggtgcaca cagctcagac gcaaccccgg gaggagcagt tcaacagcac tttccgctca | 900 |
| gtcagtgaac ttcccatcat gcaccaggac tggctcaatg gcaaggagtt caatgcagg | 960 |
| gtcaacagtg cagctttccc tgcccccatc gagaaaacca tctccaaaac caaaggcaga | 1020 |
| ccgaaggctc cacaggtgta caccattcca cctcccaagg agcagatggc caaggataaa | 1080 |
| gtcagtctga cctgcatgat aacagacttc ttccctgaag acattactgt ggagtggcag | 1140 |
| tggaatgggc agccagcgga gaactacaag aacactcagc ccatcatgga cacagatggc | 1200 |
| tcttacttcg tctacagcaa gctcaatgtg cagaagagca ctgggaggc aggaaatact | 1260 |
| ttcacctgct ctgtgttaca tgagggcctg cacaaccacc atactgagaa gagcctctcc | 1320 |
| cactctcctg gtaaa | 1335 |

<210> SEQ ID NO 93
<211> LENGTH: 445
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

-continued

```
Glu Val Lys Leu Leu Glu Ser Gly Gly Leu Val Gln Pro Gly Gly
1               5                   10                  15

Ser Leu Lys Leu Ser Cys Ala Ala Ser Gly Phe Asp Phe Ser Arg His
            20                  25                  30

Trp Met Ser Trp Val Arg Leu Ala Pro Gly Lys Gly Leu Glu Trp Ile
                35                  40                  45

Ala Glu Ile Asn Pro Asp Ser Arg Thr Ile Asn Tyr Thr Pro Ser Leu
        50                  55                  60

Lys Glu Lys Phe Ile Ile Ser Arg Asp Asn Ala Lys Asn Ser Leu Phe
65                  70                  75                  80

Leu Gln Met Asn Arg Val Arg Ser Glu Asp Thr Ala Leu Tyr Tyr Cys
                85                  90                  95

Ala Arg Arg Val Arg Ile His Tyr Tyr Gly Ala Met Asp Cys Trp Gly
                100                 105                 110

Gln Gly Thr Ser Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
        130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
                180                 185                 190

Ser Ser Thr Trp Pro Ser Glu Thr Val Thr Cys Asn Val Ala His Pro
                195                 200                 205

Ala Ser Ser Thr Lys Val Asp Lys Lys Ile Val Pro Arg Asp Cys Gly
        210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
                260                 265                 270

Phe Ser Trp Phe Val Asp Asp Val Glu Val His Thr Ala Gln Thr Gln
            275                 280                 285

Pro Arg Glu Glu Gln Phe Asn Ser Thr Phe Arg Ser Val Ser Glu Leu
        290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
        370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415
```

```
Ala Gly Asn Thr Phe Thr Cys Ser Val Leu His Glu Gly Leu His Asn
        420                 425                 430

His His Thr Glu Lys Ser Leu Ser His Ser Pro Gly Lys
    435                 440                 445

<210> SEQ ID NO 94
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
gacattgtgt tgacccagtc tcaaaaaatc gtgtccacat cagtaggagc cagggtcagc    60
gtcacctgca aggccagtca gaatgtgggt tctagtttag tctggtatca acagaaacca   120
ggtcaatctc ctaaaacact gatttactcg gcatccttcc ggtacagtgg agtccctgat   180
cgcttcacag gcagtggatc tgggacagat ttcactctca ccatcagcaa tgtgcagtct   240
gaagacttgg cagattattt ctgtcaacaa tataataact atccgctcac gttcggtgct   300
gggaccaagc tggagctgaa acgggctgat gctgcaccaa ctgtatccat cttcccacca   360
tccagtgagc agttaacatc tggaggtgcc tcagtcgtgt gcttcttgaa caacttctac   420
cccaaagaca tcaatgtcaa gtggaagatt gatggcagtg aacgacaaaa tggcgtcctg   480
aacagttgga ctgatcagga cagcaaagac agcacctaca gcatgagcag caccctcacg   540
ttgaccaagg acgagtatga acgacataac agctatacct gtgaggccac tcacaagaca   600
tcaacttcac ccattgtcaa gagcttcaac aggaatgagt gt                      642

<210> SEQ ID NO 95
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Asp Ile Val Leu Thr Gln Ser Gln Lys Ile Val Ser Thr Ser Val Gly
1               5                   10                  15

Ala Arg Val Ser Val Thr Cys Lys Ala Ser Gln Asn Val Gly Ser Ser
            20                  25                  30

Leu Val Trp Tyr Gln Gln Lys Pro Gly Gln Ser Pro Lys Thr Leu Ile
        35                  40                  45

Tyr Ser Ala Ser Phe Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Asn Tyr Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160
```

Asn Ser Trp Thr Asp Gln Asp Ser Lys Asp Ser Thr Tyr Ser Met Ser
            165                 170                 175

Ser Thr Leu Thr Leu Thr Lys Asp Glu Tyr Glu Arg His Asn Ser Tyr
        180                 185                 190

Thr Cys Glu Ala Thr His Lys Thr Ser Thr Ser Pro Ile Val Lys Ser
    195                 200                 205

Phe Asn Arg Asn Glu Cys
    210

<210> SEQ ID NO 96
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
gaggtgcagt tagtggagtc tgggggaggc ttagtgaagc ctggagggtc cctgaaactc     60
tcctgtgcag cctctggatt cactttcagt acctatgcca tgtcttggat tcgccagact    120
ccggagaaga ggctggagtg ggtcgcagga atcactaatg gtggtagttt cacctactat    180
ccagacactg tgaagggacg attcaccatc tccagagaca atgccaggaa catcctatac    240
ctgcaaatga gcggtctgag gtctgaggac acggccatgt attattgtgc aagacagggt    300
tactatggtg ttaactttga ctactggggc caaggcacca ctctcacagt ctcctcagcc    360
aaaacgacac cccatctgt ctatccactg gcccctggat ctgctgccca aactaactcc    420
atggtgaccc tgggatgcct ggtcaagggc tatttccctg agccagtgac agtgacctgg    480
aactctggat ccctgtccag cggtgtgcac accttcccag ctgtcctgca gtctgacctc    540
tacactctga gcagctcagt gactgtcccc tccagcacct ggcccagcga gaccgtcacc    600
tgcaacgttg cccacccggc cagcagcacc aaggtggaca gaaaaattgt gcccagggat    660
tgtggttgta agccttgcat atgtacagtc ccagaagtat catctgtctt catcttcccc    720
ccaaagccca aggatgtgct caccattact ctgactccta aggtcacgtg tgttgtggta    780
gacatcagca aggatgatcc cgaggtccag ttcagctggt ttgtagatga tgtggaggtg    840
cacacagctc agacgcaacc ccgggaggag cagttcaaca gcactttccg ctcagtcagt    900
gaacttccca tcatgcacca ggactggctc aatggcaagg agttcaaatg cagggtcaac    960
agtgcagctt cccctgcccc catcgagaaa accatctcca aaaccaaagg cagaccgaag   1020
gctccacagg tgtacaccat tccacctccc aaggagcaga tggccaagga taaagtcagt   1080
ctgacctgca tgataacaga cttcttccct gaagacatta ctgtggagtg cagtggaat   1140 gggcagccag cggagaacta caagaacact cagcccatca tggacacaga tggctcttac   1200
ttcgtctaca gcaagctcaa tgtgcagaag agcaactggg aggcaggaaa tactttcacc   1260
tgctctgtgt tacatgaggg cctgcacaac caccatactg agaagagcct ctcccactct   1320
cctggtaaa                                                             1329

<210> SEQ ID NO 97
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Lys | Pro | Gly |
| 1 | | | | 5 | | | | | 10 | | | | | 15 |
| Ser | Leu | Lys | Leu | Ser | Cys | Ala | Ala | Ser | Gly | Phe | Thr | Phe | Ser | Thr |
| | | | 20 | | | | | 25 | | | | | 30 | |
| Tyr | Ala | Met | Ser | Trp | Ile | Arg | Gln | Thr | Pro | Glu | Lys | Arg | Leu | Glu |
| | | | 35 | | | | | 40 | | | | | 45 | |
| Trp | Val | Ala | Gly | Ile | Thr | Asn | Gly | Gly | Ser | Phe | Thr | Tyr | Tyr | Pro |
| | | | 50 | | | | | 55 | | | | | 60 | |
| Asp | Thr | Val | Lys | Gly | Arg | Phe | Thr | Ile | Ser | Arg | Asp | Asn | Ala | Arg |
| | | | 65 | | | | | 70 | | | | | 75 | |
| Asn | Ile | Leu | Tyr | Leu | Gln | Met | Ser | Gly | Leu | Arg | Ser | Glu | Asp | Thr |
| | | | 80 | | | | | 85 | | | | | 90 | |
| Ala | Met | Tyr | Tyr | Cys | Ala | Arg | Gln | Gly | Tyr | Tyr | Gly | Val | Asn | Phe |
| | | | 95 | | | | | 100 | | | | | 105 | |
| Asp | Tyr | Trp | Gly | Gln | Gly | Thr | Thr | Leu | Thr | Val | Ser | Ser | Ala | Lys |
| | | | 110 | | | | | 115 | | | | | 120 | |
| Thr | Thr | Pro | Pro | Ser | Val | Tyr | Pro | Leu | Ala | Pro | Gly | Ser | Ala | Ala |
| | | | 125 | | | | | 130 | | | | | 135 | |
| Gln | Thr | Asn | Ser | Met | Val | Thr | Leu | Gly | Cys | Leu | Val | Lys | Gly | Tyr |
| | | | 140 | | | | | 145 | | | | | 150 | |
| Phe | Pro | Glu | Pro | Val | Thr | Val | Thr | Trp | Asn | Ser | Gly | Ser | Leu | Ser |
| | | | 155 | | | | | 160 | | | | | 165 | |
| Ser | Gly | Val | His | Thr | Phe | Pro | Ala | Val | Leu | Gln | Ser | Asp | Leu | Tyr |
| | | | 170 | | | | | 175 | | | | | 180 | |
| Thr | Leu | Ser | Ser | Ser | Val | Thr | Val | Pro | Ser | Ser | Thr | Trp | Pro | Ser |
| | | | 185 | | | | | 190 | | | | | 195 | |
| Glu | Thr | Val | Thr | Cys | Asn | Val | Ala | His | Pro | Ala | Ser | Ser | Thr | Lys |
| | | | 200 | | | | | 205 | | | | | 210 | |
| Val | Asp | Lys | Lys | Ile | Val | Pro | Arg | Asp | Cys | Gly | Cys | Lys | Pro | Cys |
| | | | 215 | | | | | 220 | | | | | 225 | |
| Ile | Cys | Thr | Val | Pro | Glu | Val | Ser | Ser | Val | Phe | Ile | Phe | Pro | Pro |
| | | | 230 | | | | | 235 | | | | | 240 | |
| Lys | Pro | Lys | Asp | Val | Leu | Thr | Ile | Thr | Leu | Thr | Pro | Lys | Val | Thr |
| | | | 245 | | | | | 250 | | | | | 255 | |
| Cys | Val | Val | Val | Asp | Ile | Ser | Lys | Asp | Asp | Pro | Glu | Val | Gln | Phe |
| | | | 260 | | | | | 265 | | | | | 270 | |
| Ser | Trp | Phe | Val | Asp | Asp | Val | Glu | Val | His | Thr | Ala | Gln | Thr | Gln |
| | | | 275 | | | | | 280 | | | | | 285 | |
| Pro | Arg | Glu | Glu | Gln | Phe | Asn | Ser | Thr | Phe | Arg | Ser | Val | Ser | Glu |
| | | | 290 | | | | | 295 | | | | | 300 | |
| Leu | Pro | Ile | Met | His | Gln | Asp | Trp | Leu | Asn | Gly | Lys | Glu | Phe | Lys |
| 305 | | | | | 310 | | | | | 315 | | | | |
| Cys | Arg | Val | Asn | Ser | Ala | Ala | Phe | Pro | Ala | Pro | Ile | Glu | Lys | Thr |
| | | | 320 | | | | | 325 | | | | | 330 | |
| Ile | Ser | Lys | Thr | Lys | Gly | Arg | Pro | Lys | Ala | Pro | Gln | Val | Tyr | Thr |
| | | | 335 | | | | | 340 | | | | | 345 | |
| Ile | Pro | Pro | Lys | Glu | Gln | Met | Ala | Lys | Asp | Lys | Val | Ser | Leu | Thr |
| | | | 350 | | | | | 355 | | | | | 360 | |
| Cys | Met | Ile | Thr | Asp | Phe | Phe | Pro | Glu | Asp | Ile | Thr | Val | Glu | Trp |
| | | | 365 | | | | | 370 | | | | | 375 | |
| Gln | Trp | Asn | Gly | Gln | Pro | Ala | Glu | Asn | Tyr | Lys | Asn | Thr | Gln | Pro |
| | | | 380 | | | | | 385 | | | | | 390 | |
| Ile | Met | Asp | Thr | Asp | Gly | Ser | Tyr | Phe | Val | Tyr | Ser | Lys | Leu | Asn |
| | | | 395 | | | | | 400 | | | | | 405 | |
| Val | Gln | Lys | Ser | Asn | Trp | Glu | Ala | Gly | | | | | | |
| | | | 410 | | | | | 415 | | | | | | |

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 98
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
gatgctgtga tgacccaaac tccactctcc ctgcctgtca gtcttggaga tcaagcctcc      60
atctcttgca ggtctagtca gagccttgaa aacagtaacg aaacacttta tttgaactgg    120
tacctccaga aaccaggcca gtctccacag ctcctgatct acagggtttc caaccgattt    180
tctggggtcc cagacaggtt cagtggtagt ggatcaggga cagatttcac actgaaaatc    240
atcagagtgg aggctgagga tttgggactt tatttctgcc tccaagttac acatgtcccg    300
cacacgttcg gaggggggac caaactggaa ttaaaacggg ctgatgctgc accaactgta    360
tccatcttcc caccatccag tgagcagtta acatctggag gtgcctcagt cgtgtgcttc    420
ttgaacaact ctaccccaa agacatcaat gtcaagtgga gattgatgg cagtgaacga    480 caaaatggcg tcctgaacag ttggactgat caggacagca agacagcac ctacagcatg    540 agcagcaccc tcacgttgac caaggacgag tatgaacgac ataacagcta cctgtgagg    600 gccactcaca agacatcaac ttcacccatt gtcaagagct tcaacaggaa tgagtgt      657

<210> SEQ ID NO 99
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ile Arg Val Glu Ala Glu Asp Leu Gly Leu Tyr Phe Cys Leu Gln Val
                85                  90                  95

Thr His Val Pro His Thr Phe Gly Gly Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg

| | | 145 | | | 150 | | | | 155 | | | | 160 | |
|---|---|---|---|---|---|---|---|---|---|---|---|---|---|---|

Gln Asn Gly Val Leu Asn Ser Trp Thr Asp Gln Asp Ser Lys Asp Ser
                                 165                               170                               175

Thr Tyr Ser Met Ser Ser Thr Leu Thr Leu Thr Lys Asp Glu Tyr Glu
                               180                               185                               190

Arg His Asn Ser Tyr Thr Cys Glu Ala Thr His Lys Thr Ser Thr Ser
                195                               200                               205

Pro Ile Val Lys Ser Phe Asn Arg Asn Glu Cys
            210                           215

<210> SEQ ID NO 100
<211> LENGTH: 1344
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 100

| | | |
|---|---|---|
| gaagtgaagc tggtggagtc gggggaggc ttagtgaagc ctggagcgtc tctgaaactc | 60 |
| tcctgtgcag cctctggatt cattttcagt tcctatggca tgtcttgggt tcgccagact | 120 |
| tcagacaaga ggctggagtg ggtcgcttcc attagtagtg gtggtggtac cacctactat | 180 |
| ctagacactg taaagggccg attcaccatc tccagagaga tgccaagga caccctgtac | 240 |
| ctgcaaatga gtggtctgaa gtctgaagac acggccttgt attactgtac aagaggccaa | 300 |
| tggttactaa agtttgctta ctggggccaa gggactctgg tcactgtctc tgcagccaaa | 360 |
| acaacagccc catcggtcta tccactggcc cctgtgtgtg gagatacaac tggctcctcg | 420 |
| gtgactctag gatgcctggt caagggttat ttccctgagc cagtgacctt gacctggaac | 480 |
| tctggatccc tgtccagtgg tgtgcacacc ttcccagctg tcctgcagtc tgacctctac | 540 |
| accctcagca gctcagtgac tgtaacctcg agcacctggc ccagccagtc catcacctgc | 600 |
| aatgtggccc acccggcaag cagcaccaag gtggacaaga aaattgagcc cagagggccc | 660 |
| acaatcaagc cctgtcctcc atgcaaatgc ccagcaccta acctcttggg tggaccatcc | 720 |
| gtcttcatct tccctccaaa gatcaaggat gtactcatga tctccctgag ccccatagtc | 780 |
| acatgtgtgg tggtggatgt gagcgaggat gacccagatg tccagatcag ctggtttgtg | 840 |
| aacaacgtgg aagtacacac agctcagaca caaacccata gagaggatta caacagtact | 900 |
| ctccgggtgg tcagtgccct ccccatccag caccaggact ggatgagtgg caaggagttc | 960 |
| aaatgcaagg tcaacaacaa agacctccca gcgcccatcg agaaccat ctcaaaaccc | 1020 |
| aaagggtcag taagagctcc acaggtatat gtcttgcctc caccagaaga agagatgact | 1080 |
| aagaaacagg tcactctgac ctgcatggtc acagacttca tgcctgaaga catttacgtg | 1140 |
| gagtggacca acaacgggaa aacagagcta aactacaaga cactgaacc agtcctggac | 1200 |
| tctgatggtt cttacttcat gtacagcaag ctgagagtgg aaaagaagaa ctgggtggaa | 1260 |
| agaaatagct actcctgttc agtggtccac gagggtctgc acaatcacca cacgactaag | 1320 |
| agcttctccc ggactccggg taaa | 1344 |

<210> SEQ ID NO 101
<211> LENGTH: 448
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 101

```
Glu Val Lys Leu Val Glu Ser Gly Gly Gly Leu Val Lys Pro Gly Ala
  1               5                  10                  15

Ser Leu Lys Leu Ser Cys Ala Ala Ser Gly Phe Ile Phe Ser Ser Tyr
             20                  25                  30

Gly Met Ser Trp Val Arg Gln Thr Ser Asp Lys Arg Leu Glu Trp Val
         35                  40                  45

Ala Ser Ile Ser Ser Gly Gly Thr Thr Tyr Tyr Leu Asp Thr Val
     50                  55                  60

Lys Gly Arg Phe Thr Ile Ser Arg Glu Asn Ala Lys Asp Thr Leu Tyr
 65                  70                  75                  80

Leu Gln Met Ser Gly Leu Lys Ser Glu Asp Thr Ala Leu Tyr Tyr Cys
                 85                  90                  95

Thr Arg Gly Gln Trp Leu Leu Lys Phe Ala Tyr Trp Gly Gln Gly Thr
            100                 105                 110

Leu Val Thr Val Ser Ala Ala Lys Thr Thr Ala Pro Ser Val Tyr Pro
        115                 120                 125

Leu Ala Pro Val Cys Gly Asp Thr Thr Gly Ser Ser Val Thr Leu Gly
130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
    370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
```

```
                405                 410                 415
Asn Trp Val Glu Arg Asn Ser Tyr Ser Cys Ser Val His Glu Gly
            420                 425                 430

Leu His Asn His His Thr Thr Lys Ser Phe Ser Arg Thr Pro Gly Lys
            435                 440                 445

<210> SEQ ID NO 102
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
caacttgtgc tcactcagtc atcttcagcc tctttctccc tgggagcctc agcaaaactc      60
acgtgcacct tgagtagtca gcacactacg tacaccattg aatggtatca gcaactgcca     120
ctcaagcctc ctaagtatgt gatggagctt aagaaagatg gaagccacag cacaggtgtt     180
gggattcctg atcgcttctc tggatccagc tctggtgctg atcgctacct taccatttcc     240
aacatccagc ctgaagatga agcaatatac atctgtggtg tgggtgagac aattgaggac     300
caatttgtgt atgttttcgg cggtggcacc aaggtcactg tcctaggtca gcccaagtcc     360
actcccactc tcaccgtgtt tccaccttcc tctgaggagc tcaaggaaaa caaagccaca     420
ctggtgtgtc tgatttccaa cttttccccg agtggtgtga cagtggcctg aaggcaaat      480 ggtacaccta tcacccaggg tgtggacact tcaaatccca ccaaagaggg caacaagttc     540
atggccagca gcttcctaca tttgacatcg gaccagtgga gatctcacaa cagttttacc     600
tgtcaagtta cacatgaagg ggacactgtg agaagagtc tgtctcctgc agaatgtctc     660

<210> SEQ ID NO 103
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Leu Val Leu Thr Gln Ser Ser Ser Ala Ser Phe Ser Leu Gly Ala
1               5                   10                  15

Ser Ala Lys Leu Thr Cys Thr Leu Ser Ser Gln His Thr Thr Tyr Thr
            20                  25                  30

Ile Glu Trp Tyr Gln Gln Leu Pro Leu Lys Pro Lys Tyr Val Met
        35                  40                  45

Glu Leu Lys Lys Asp Gly Ser His Ser Thr Gly Val Gly Ile Pro Asp
    50                  55                  60

Arg Phe Ser Gly Ser Ser Ser Gly Ala Asp Arg Tyr Leu Thr Ile Ser
65                  70                  75                  80

Asn Ile Gln Pro Glu Asp Glu Ala Ile Tyr Ile Cys Gly Val Gly Glu
                85                  90                  95

Thr Ile Glu Asp Gln Phe Val Tyr Val Phe Gly Gly Gly Thr Lys Val
            100                 105                 110

Thr Val Leu Gly Gln Pro Lys Ser Thr Pro Thr Leu Thr Val Phe Pro
        115                 120                 125

Pro Ser Ser Glu Glu Leu Lys Glu Asn Lys Ala Thr Leu Val Cys Leu
    130                 135                 140
```

```
Ile Ser Asn Phe Ser Pro Ser Gly Val Thr Val Ala Trp Lys Ala Asn
145                 150                 155                 160

Gly Thr Pro Ile Thr Gln Gly Val Asp Thr Ser Asn Pro Thr Lys Glu
                165                 170                 175

Gly Asn Lys Phe Met Ala Ser Ser Phe Leu His Leu Thr Ser Asp Gln
            180                 185                 190

Trp Arg Ser His Asn Ser Phe Thr Cys Gln Val Thr His Glu Gly Asp
        195                 200                 205

Thr Val Glu Lys Ser Leu Ser Pro Ala Glu Cys Leu
    210                 215                 220
```

<210> SEQ ID NO 104
<211> LENGTH: 1320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104

```
gaggtgcagc ttcaggagtc aggacctagc ctcgtgaaac cttctcagac tctgtccctc      60
acctgttatg tcactggcga ctccatcacc agtgattact ggaattggat ccggaaattc     120
ccaggaaata aacttgagta catgggatat atcagctaca gtggtagcac ttactacaat     180
ccatctctca aaagtcgaat ctccatcact cgagacacat ccaagaacca gttctacctt     240
cggttgaatt ctgtgactac tgaggacaca gccacatatt actgtgcaag aacccatata     300
cttacgattg cttactgggg ccaagggact ctggtcactg tctctgcagc caaaacgaca     360
cccccatctg tctatccact ggcccctgga tctgctgccc aaactaactc catggtgacc     420
ctgggatgcc tggtcaaggg ctatttccct gagccagtga cagtgacctg aactctgga      480
tccctgtcca gcggtgtgca caccttccca gctgtcctgc agtctgacct ctacactctg     540
agcagctcag tgactgtccc ctccagcacc tggcccagcg accgtcac ctgcaacgtt       600
gcccacccgg ccagcagcac caaggtggac aagaaaattg tgcccaggga ttgtggttgt     660
aagccttgca tatgtacagt cccagaagta tcatctgtct tcatcttccc cccaaagccc     720
aaggatgtgc tcaccattac tctgactcct aaggtcacgt gtgttgtggt agacatcagc     780
aaggatgatc ccgaggtcca gttcagctgg tttgtagatg atgtggaggt gcacacagct     840
cagacgcaac cccgggagga gcagttcaac agcactttcc gctcagtcag tgaacttccc     900
atcatgcacc aggactggct caatggcaag gagttcaaat gcagggtcaa cagtgcagct     960
ttccctgccc ccatcgagaa aaccatctcc aaaaccaaag gcagaccgaa ggctccacag    1020
gtgtacacca ttccacctcc caaggagcag atggccaagg ataaagtcag tctgacctgc    1080
atgataacag acttcttccc tgaagacatt actgtggagt ggcagtggaa tgggcagcca    1140
gcggagaact acaagaacac tcagcccatc atggacacag atggctctta cttcgtctac    1200
agcaagctca atgtgcagaa gagcaactgg gaggcaggaa atactttcac ctgctctgtg    1260
ttacatgagg gcctgcacaa ccaccatact gagaagagcc tctcccactc tcctggtaaa    1320
```

<210> SEQ ID NO 105
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 105

Glu Val Gln Leu Gln Glu Ser Gly Pro Ser Leu Val Lys Pro Ser Gln
1               5                   10                  15

Thr Leu Ser Leu Thr Cys Tyr Val Thr Gly Asp Ser Ile Thr Ser Asp
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Ser Thr Tyr Tyr Asn Pro Ser Leu Lys
50                  55                  60

Ser Arg Ile Ser Ile Thr Arg Asp Thr Ser Lys Asn Gln Phe Tyr Leu
65                  70                  75                  80

Arg Leu Asn Ser Val Thr Thr Glu Asp Thr Ala Thr Tyr Tyr Cys Ala
                85                  90                  95

Arg Thr His Ile Leu Thr Ile Ala Tyr Trp Gly Gln Gly Thr Leu Val
            100                 105                 110

Thr Val Ser Ala Ala Lys Thr Thr Pro Pro Ser Val Tyr Pro Leu Ala
        115                 120                 125

Pro Gly Ser Ala Ala Gln Thr Asn Ser Met Val Thr Leu Gly Cys Leu
130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Pro Ser Ser Thr Trp Pro
            180                 185                 190

Ser Glu Thr Val Thr Cys Asn Val Ala His Pro Ala Ser Ser Thr Lys
        195                 200                 205

Val Asp Lys Lys Ile Val Pro Arg Asp Cys Gly Cys Lys Pro Cys Ile
210                 215                 220

Cys Thr Val Pro Glu Val Ser Ser Val Phe Ile Phe Pro Pro Lys Pro
225                 230                 235                 240

Lys Asp Val Leu Thr Ile Thr Leu Thr Pro Lys Val Thr Cys Val Val
                245                 250                 255

Val Asp Ile Ser Lys Asp Asp Pro Glu Val Gln Phe Ser Trp Phe Val
            260                 265                 270

Asp Asp Val Glu Val His Thr Ala Gln Thr Gln Pro Arg Glu Glu Gln
        275                 280                 285

Phe Asn Ser Thr Phe Arg Ser Val Ser Glu Leu Pro Ile Met His Gln
290                 295                 300

Asp Trp Leu Asn Gly Lys Glu Phe Lys Cys Arg Val Asn Ser Ala Ala
305                 310                 315                 320

Phe Pro Ala Pro Ile Glu Lys Thr Ile Ser Lys Thr Lys Gly Arg Pro
                325                 330                 335

Lys Ala Pro Gln Val Tyr Thr Ile Pro Pro Lys Glu Gln Met Ala
            340                 345                 350

Lys Asp Lys Val Ser Leu Thr Cys Met Ile Thr Asp Phe Phe Pro Glu
        355                 360                 365

Asp Ile Thr Val Glu Trp Gln Trp Asn Gly Gln Pro Ala Glu Asn Tyr
370                 375                 380

Lys Asn Thr Gln Pro Ile Met Asp Thr Asp Gly Ser Tyr Phe Val Tyr
385                 390                 395                 400

Ser Lys Leu Asn Val Gln Lys Ser Asn Trp Glu Ala Gly Asn Thr Phe
                405                 410                 415
```

```
Thr Cys Ser Val Leu His Glu Gly Leu His Asn His Thr Glu Lys
            420                 425                 430
Ser Leu Ser His Ser Pro Gly Lys
        435                 440
```

<210> SEQ ID NO 106
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106

```
caggctgttg tgactcagga atctgcactc accacatcac ctggtgaaac agtcacactc     60
acttgtcgct caagtgccgg ggctgttaca actagtaact ttgccaactg ggtccaagaa    120
aaaccagatc atttattcac tggtctaata ggtgatacca acatccgagc tccaggtgtt    180
cctgccagat tctcaggctc cctgattgga gacaaggctg ccctcaccat cacagggca     240 cagactgagg atgaggcaat atatttctgt gctctttggt acagcaacca ttactgggtg    300
ttcggtggag gaaccaaact gactgtccta ggccagccca gtcttcgcc atcagtcacc     360 ctgtttccac cttcctctga agagctcgag actaacaagg ccacactggt gtgtacgatc    420
actgatttct acccaggtgt ggtgacagtg actggaagg tagatggtac ccctgtcact     480
cagggtatgg agacaaccca gccttccaaa cagagcaaca caagtacat ggctagcagc     540 tacctgaccc tgacagcaag agcatgggaa aggcatagca gttacagctg ccaggtcact    600
catgaaggtc acactgtgga aagagtttg tcccgtgctg actgttcc                 648
```

<210> SEQ ID NO 107
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

```
Gln Ala Val Val Thr Gln Glu Ser Ala Leu Thr Thr Ser Pro Gly Glu
1               5                   10                  15

Thr Val Thr Leu Thr Cys Arg Ser Ser Ala Gly Ala Val Thr Thr Ser
            20                  25                  30

Asn Phe Ala Asn Trp Val Gln Glu Lys Pro Asp His Leu Phe Thr Gly
        35                  40                  45

Leu Ile Gly Asp Thr Asn Ile Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Tyr Trp Val Phe Gly Gly Gly Thr Lys Leu Thr Val Leu Gly Gln
            100                 105                 110

Pro Lys Ser Ser Pro Ser Val Thr Leu Phe Pro Pro Ser Ser Glu Glu
        115                 120                 125

Leu Glu Thr Asn Lys Ala Thr Leu Val Cys Thr Ile Thr Asp Phe Tyr
    130                 135                 140

Pro Gly Val Val Thr Val Asp Trp Lys Val Asp Gly Thr Pro Val Thr
```

```
                145                 150                 155                 160
Gln Gly Met Glu Thr Thr Gln Pro Ser Lys Gln Ser Asn Asn Lys Tyr
                    165                 170                 175

Met Ala Ser Ser Tyr Leu Thr Leu Thr Ala Arg Ala Trp Glu Arg His
                    180                 185                 190

Ser Ser Tyr Ser Cys Gln Val Thr His Glu Gly His Thr Val Glu Lys
                    195                 200                 205

Ser Leu Ser Arg Ala Asp Cys Ser
                    210                 215

<210> SEQ ID NO 108
<211> LENGTH: 1323
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
gaggtgcagc ttcaggagtc aggacctagc ctcgtgaaac cttctcagac tctgtccctc        60
acctgttctg tcactggcga ctccatcacc agtggttact ggaactggat ccggaaattc       120
ccagggaata acttgagta catggggtac ataagctaca gtggtaaaac ttactacaat        180
ccatctctca aaagtcgaat ctccatcact cgagacacat ccaagaacca ttactacctg       240
cagttgattt ctgtgactgc tgaggacaca gccacatatt actgtgcaag gtctaagtac       300
gactatgcta tggactactg gggtcaagga acctcagtca ccgtctcctc agccaaaacg       360
acacccccat ctgtctatcc actggcccct ggatctgctg cccaaactaa ctccatggtg       420
accctgggat gcctggtcaa ggctatttc cctgagccag tgacagtgac ctggaactct       480
ggatccctgt ccagcggtgt gcacaccttc ccagctgtcc tgcagtctga cctctacact       540
ctgagcagct cagtgactgt cccctccagc acctggccca gcgagaccgt cacctgcaac       600
gttgcccacc cggccagcag caccaaggtg gacaagaaaa ttgtgcccag ggattgtggt       660
tgtaagcctt gcatatgtac agtcccagaa gtatcatctg tcttcatctt ccccccaaag       720
cccaaggatg tgctcaccat tactctgact cctaaggtca cgtgtgttgt ggtagacatc       780
agcaaggatg atcccgaggt ccagttcagc tggtttgtag atgatgtgga ggtgcacaca       840
gctcagacgc aaccccggga ggagcagttc aacagcactt tccgctcagt cagtgaactt       900
cccatcatgc accaggactg gctcaatggc aaggagttca atgcagggt caacagtgca       960 gctttccctg cccccatcga gaaaaccatc tccaaaacca aaggcagacc gaaggctcca      1020
caggtgtaca ccattccacc tcccaaggag cagatggcca aggataaagt cagtctgacc      1080
tgcatgataa cagacttctt ccctgaagac attactgtgg agtggcagtg gaatgggcag      1140
ccagcggaga actacaagaa cactcagccc atcatggaca cagatggctc ttacttcgtc      1200
tacagcaagc tcaatgtgca gaagagcaac tgggaggcag gaaatacttt cacctgctct      1260
gtgttacatg agggcctgca caaccaccat actgagaaga gcctctccca ctctcctggt      1320
aaa                                                                     1323

<210> SEQ ID NO 109
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 109

```
Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Lys Thr Tyr Tyr Asn Pro Ser Leu Lys
    50                  55                  60

Ser Arg Ile Ser Ile Thr Arg Asp Thr Ser Lys Asn His Tyr Tyr Leu
65                  70                  75                  80

Gln Leu Ile Ser Val Thr Ala Glu Asp Thr Ala Thr Tyr Tyr Cys Ala
                85                  90                  95

Arg Ser Lys Tyr Asp Tyr Ala Met Asp Tyr Trp Gly Gln Gly Thr Ser
            100                 105                 110

Val Thr Val Ser Ser Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Thr Trp
            180                 185                 190

Pro Ser Glu Thr Val Thr Cys Asn Val Ala His Pro Ala Ser Ser Thr
        195                 200                 205

Lys Val Asp Lys Lys Ile Val Pro Arg Asp Cys Gly Cys Lys Pro Cys
    210                 215                 220

Ile Cys Thr Val Pro Glu Val Ser Ser Val Phe Ile Phe Pro Pro Lys
225                 230                 235                 240

Pro Lys Asp Val Leu Thr Ile Thr Leu Thr Pro Lys Val Thr Cys Val
                245                 250                 255

Val Val Asp Ile Ser Lys Asp Asp Pro Glu Val Gln Phe Ser Trp Phe
            260                 265                 270

Val Asp Asp Val Glu Val His Thr Ala Gln Thr Gln Pro Arg Glu Glu
        275                 280                 285

Gln Phe Asn Ser Thr Phe Arg Ser Val Ser Glu Leu Pro Ile Met His
    290                 295                 300

Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
                325                 330                 335

Pro Lys Ala Pro Gln Val Tyr Thr Ile Pro Pro Lys Glu Gln Met
            340                 345                 350

Ala Lys Asp Lys Val Ser Leu Thr Cys Met Ile Thr Asp Phe Phe Pro
        355                 360                 365

Glu Asp Ile Thr Val Glu Trp Gln Trp Asn Gly Gln Pro Ala Glu Asn
    370                 375                 380

Tyr Lys Asn Thr Gln Pro Ile Met Asp Thr Asp Gly Ser Tyr Phe Val
385                 390                 395                 400

Tyr Ser Lys Leu Asn Val Gln Lys Ser Asn Trp Glu Ala Gly Asn Thr
```

Phe Thr Cys Ser Val Leu His Glu Gly Leu His Asn His His Thr Glu
            420                 425                 430

Lys Ser Leu Ser His Ser Pro Gly Lys
        435                 440

<210> SEQ ID NO 110
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
gacattgtgc tgacccaatc tccagcttct ttggctgtgt ctctaggaca gagggccacc     60
atctcctgca gagccagcga aattgttgat aattttggca ttagttttat gaactggttc    120
caacagaaac caggacagcc acccaaactc ctcatctatg ctgcatccaa ccaaggatcc    180
ggggtccctg ccaggtttag tggcagtggg tctgggacag acttcagcct caacatccat    240
cctgtggagg aggatgatac tgcaatgtat ttctgtcagc aaagtaagga ggttcctccg    300
acgttcggtg gaggcaccaa gctggaaatc aaacggctg atgctgcacc aactgtatcc     360
atcttcccac catccagtga gcagttaaca tctggaggtg cctcagtcgt gtgcttcttg    420
aacaacttct accccaaaga catcaatgtc aagtggaaga ttgatggcag tgaacgacaa    480
aatggcgtcc tgaacagttg gactgatcag gacagcaaag acagcaccta cagcatgagc    540
agcaccctca cgttgaccaa ggacgagtat gaacgacata cagctatac ctgtgaggcc     600 actcacaaga catcaacttc acccattgtc aagagcttca caggaatga gtgt           654

<210> SEQ ID NO 111
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ile Val Asp Asn Phe
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Thr Ala Met Tyr Phe Cys Gln Gln Ser Lys
                85                  90                  95

Glu Val Pro Pro Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

```
Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
            165                 170                 175

Tyr Ser Met Ser Ser Thr Leu Thr Leu Thr Lys Asp Glu Tyr Glu Arg
        180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```

```
<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
cgactggagc acgaggacac tga                                             23

<210> SEQ ID NO 113
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ctaatacgac tcactatagg gcaagcagtg gtatcaacgc agagt                     45

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
ctaatacgac tcactatagg gc                                              22

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
tatgcaaggc ttacaaccac a                                               21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
aggacagggc ttgattgtgg g                                               21
```

-continued

<210> SEQ ID NO 117
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
ctcattcctg ttgaagctct tgacaat                                            27

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gcacgggaca aactcttctc                                                    20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
cacagtgtcc ccttcatgtg                                                    20

<210> SEQ ID NO 120
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
gtaaaacgac ggccagt                                                       17

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
caggaaacag ctatgacc                                                      18

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Glu Ile Asn Pro Asp Ser Arg Thr Ile Asn Tyr Ala Pro Ser Val Lys
1               5                   10                  15

Gly

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Arg Val Arg Ile His Tyr Tyr Gly Ala Met Asp Ser
1               5                   10

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Phe Thr Phe Ser Arg His
1               5

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Arg Val Arg Ile His Tyr Tyr Gly Ala Met Asp Ser
1               5                   10

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Gly Ser Ile Ser Ser Gly
1               5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Phe Thr Phe Ser Arg His Trp
1               5

<210> SEQ ID NO 128
<211> LENGTH: 14
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 128

Ala Arg Arg Val Arg Ile His Tyr Tyr Gly Ala Met Asp Ser
1               5                   10

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Gly Ser Ile Ser Ser Gly Tyr
1               5

<210> SEQ ID NO 130
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Arg Ala Ser Gln Asn Val Gly Ser Ser Leu Val
1               5                   10

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ser Ala Ser Phe Leu Tyr Ser
1               5

<210> SEQ ID NO 132
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132
gaggtgaagc ttctcgagtc tggaggtggc ctggtgcagc cgggtggatc cctgaaactc        60
tcctgtgcag cctcaggatt cgattttagt agacactgga tgagttgggt ccggctggct       120
ccagggaaag ggctagaatg gatcgcagaa attaatccag atagcagaac gataaactat       180
acgccatctc taaaggagaa attcatcatc tccagagaca acgccaaaaa ttcgctgttt       240
ctgcaaatga acagtgagat ctgaggac acagccctttt attactgtgc aagacgggta       300
agaattcatt actacggcgc tatggacagc tggggtcaag aacctcagt caccgtctcc       360 tca                                                                    363

<210> SEQ ID NO 133
<211> LENGTH: 121
<212> TYPE: PRT

-continued

<213> ORGANISM: Artificial Sequence
<220> FEATURE:
<223> OTHER INFORMATION: Description of Artificial Sequence: Synthetic
      polypeptide

<400> SEQUENCE: 133

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg His
            20                  25                  30

Trp Met Ser Trp Val Arg Leu Ala Pro Gly Lys Gly Leu Glu Trp Ile
        35                  40                  45

Ala Glu Ile Asn Pro Asp Ser Arg Thr Ile Asn Tyr Thr Pro Ser Leu
50                  55                  60

Lys Glu Lys Phe Ile Ile Ser Arg Asp Asn Ala Lys Asn Ser Leu Phe
65                  70                  75                  80

Leu Gln Met Asn Arg Val Arg Ser Glu Asp Thr Ala Leu Tyr Tyr Cys
                85                  90                  95

Ala Arg Arg Val Arg Ile His Tyr Tyr Gly Ala Met Asp Ser Trp Gly
            100                 105                 110

Gln Gly Thr Ser Val Thr Val Ser Ser
        115                 120

<210> SEQ ID NO 134
<211> LENGTH: 363
<212> TYPE: DNA
<213> ORGANISM: Artificial Sequence
<220> FEATURE:
<223> OTHER INFORMATION: Description of Artificial Sequence: Synthetic
         polynucleotide

<400> SEQUENCE: 134
gaggttcagc tggtagaatc cggaggaggg ttggtccaac ctggtggatc actcagactt    60
tcatgcgccg ccagcggctt tgacttctca cgacattgga tgagctgggt ccggcaggct   120
ccaggcaagg gcctcgagtg ggttagcgag atcaatccag acagcagaac cattaactat   180
acacccagtc tgaaggagcg gttcaccata agccgtgata atgccaagaa ctccctgtac   240
ttgcagatga actccttgcg cgctgaagat acagctgtgt actattgtgc aaggcgcgtg   300
cgaatccact attacggggc aatggattct tggggccagg gtactaccgt gactgtgagt   360
tct                                                                 363

<210> SEQ ID NO 135
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg His
            20                  25                  30

Trp Met Ser Trp Val Arg Gln Ala Pro Gly Lys Gly Leu Glu Trp Val
        35                  40                  45

Ser Glu Ile Asn Pro Asp Ser Arg Thr Ile Asn Tyr Thr Pro Ser Leu
50                  55                  60

```
Lys Glu Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Arg Val Arg Ile His Tyr Tyr Gly Ala Met Asp Ser Trp Gly
            100                 105                 110

Gln Gly Thr Thr Val Thr Val Ser Ser
            115                 120
```

<210> SEQ ID NO 136
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 136

```
gaggttcagc tggtagaatc cggaggaggg ttggtccaac ctggtggatc actcagactt    60
tcatgcgccg ccagcggctt taccttctca cgacattgga tgagctgggt ccggcaggct   120
ccaggcaagg gcctcgagtg ggttagcgag atcaatccag acagcagaac cattaactat   180
gcccccagtg tgaagggccg gttcaccata agccgtgata atgccaagaa ctccctgtac   240
ttgcagatga actccttgcg cgctgaagat acagctgtgt actattgtgc aaggcgcgtg   300
cgaatccact attacggggc aatggattct tggggccagg gtactaccgt gactgtgagt   360
tct                                                                363
```

<210> SEQ ID NO 137
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 137

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg His
             20                  25                  30

Trp Met Ser Trp Val Arg Gln Ala Pro Gly Lys Gly Leu Glu Trp Val
             35                  40                  45

Ser Glu Ile Asn Pro Asp Ser Arg Thr Ile Asn Tyr Ala Pro Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Arg Val Arg Ile His Tyr Tyr Gly Ala Met Asp Ser Trp Gly
            100                 105                 110

Gln Gly Thr Thr Val Thr Val Ser Ser
            115                 120
```

<210> SEQ ID NO 138
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 138

```
gatatccagt tgactcagtc tcagtcctttt gtgagtacat cagtgggcga cagggtcacc      60
gtgacctgcc agcatcaca gaacgttgga agctctcttg tctggtatca gcaaaagcct       120
gggaagagcc ccaaaaccct catctattct gcttcctttc tgtactccgg cgtaccaagt      180
agattctctg gtagcggatc cgggacagag ttcactctca caattagcag tgtgcagcct      240
gaggatttcg ccgactactt ctgtcagcaa tacaataact atcccctgac ttttggtggc      300
ggcaccaaag tggaaatcaa g                                                321
```

<210> SEQ ID NO 139
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

```
Asp Ile Gln Leu Thr Gln Ser Gln Ser Phe Val Ser Thr Ser Val Gly
1               5                   10                  15

Asp Arg Val Thr Val Thr Cys Arg Ala Ser Gln Asn Val Gly Ser Ser
                20                  25                  30

Leu Val Trp Tyr Gln Gln Lys Pro Gly Lys Ser Pro Lys Thr Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Glu Phe Thr Leu Thr Ile Ser Ser Val Gln Pro
65                  70                  75                  80

Glu Asp Phe Ala Asp Tyr Phe Cys Gln Gln Tyr Asn Asn Tyr Pro Leu
                85                  90                  95

Thr Phe Gly Gly Gly Thr Lys Val Glu Ile Lys
            100                 105
```

<210> SEQ ID NO 140
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140

```
gacattcagc tgactcagtc gccgtcgttt ttgtcggcgt ccgtgggtga cagagtgact      60
atcacatgtc gcgcttcgca aaacgtcgga tcatcgcttg tgtggtatca gcagaaaccc      120
ggtaaagccc ctaagaccct catctattca gcgtcatttc tgtatagcgg ggtcccctca     180
cggttcagcg gatccggctc cgggaccgag ttcacactca ctatttcgag cttgcagccg      240
gaagattttg caacgtacta ctgccagcaa tacaataact acccactcac gttcggaggg      300
ggaacgaagg tagagatcaa g                                                321
```

<210> SEQ ID NO 141
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Asn Val Gly Ser Ser
            20                  25                  30

Leu Val Trp Tyr Gln Gln Lys Pro Gly Lys Ala Pro Lys Thr Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gly Gly Thr Lys Val Glu Ile Lys
            100                 105

<210> SEQ ID NO 142
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142
caagttcagc tgcaagaatc cggaccagga ttggtcaaac cttcagagac actcagcctg      60
acttgcaccg tgagcggtgg cagcatatcc tccggttatt ggaactggat ccggcagcca     120
ccaggcaagg gcctcgagtg gattggctac atcagctata gcgggaaaac ctattacaac     180
cccagtctga agagccgagt gaccataagc gtcgatacaa gtaagaacca gttctccctg     240
aagctctcat ccgtgaccgc cgctgataca gctgtgtact attgtgcaag gtcaaagtat     300
gactacgcaa tggactattg gggccagggt actctggtga ctgtgagttc t               351

<210> SEQ ID NO 143
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Tyr Trp Asn Trp Ile Arg Gln Pro Pro Gly Lys Gly Leu Glu Trp Ile
        35                  40                  45

Gly Tyr Ile Ser Tyr Ser Gly Lys Thr Tyr Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Lys Tyr Asp Tyr Ala Met Asp Tyr Trp Gly Gln Gly Thr Leu
            100                 105                 110

Val Thr Val Ser Ser
        115

<210> SEQ ID NO 144
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144
caagttcagc tgcaagaatc cggaccagga ttggtcaaac ccagcgaaac actctctctt    60
acatgcaccg tgagcggcga ctctatcacc tcagggtatt ggaattggat tcggaaaccc   120
ccaggcaaga agctcgagta catgggttac atcagttaca gcgggaaaac ctactataac   180
cccagtctga agagcagaat caccataagc cgtgatacct ctaagaacca gtactccctg   240
aagctgagtt ccgtaacagc agctgataca gctgtgtact attgtgcaag gagtaagtat   300
gactacgcaa tggactattg gggccagggt actcttgtga ctgtgagttc t             351

<210> SEQ ID NO 145
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Gly
            20                  25                  30

Tyr Trp Asn Trp Ile Arg Lys Pro Pro Gly Lys Lys Leu Glu Tyr Met
        35                  40                  45

Gly Tyr Ile Ser Tyr Ser Gly Lys Thr Tyr Tyr Asn Pro Ser Leu Lys
    50                  55                  60

Ser Arg Ile Thr Ile Ser Arg Asp Thr Ser Lys Asn Gln Tyr Ser Leu
65                  70                  75                  80

Lys Leu Ser Ser Val Thr Ala Ala Asp Thr Ala Val Tyr Tyr Cys Ala
                85                  90                  95

Arg Ser Lys Tyr Asp Tyr Ala Met Asp Tyr Trp Gly Gln Gly Thr Leu
            100                 105                 110

Val Thr Val Ser Ser
        115

<210> SEQ ID NO 146
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146
caagttcagc tgcaagaatc cggaccagga ttggtcaaac cttcagagac actcagcctg    60
acttgcaccg tgagcggtgg cagcatatcc tccggttatt ggaactggat ccggaagcca   120
ccaggcaaga agctcgagta cattggctac atcagctata gcgggaaaac ctattacaac   180
cccagtctga agagccgagt gaccataagc agggatacaa gtaagaacca gttctccctg   240

```
aagctctcat ccgtgaccgc cgctgataca gctgtgtact attgtgcaag gtcaaagtat        300
gactacgcaa tggactattg gggccagggt actctggtga ctgtgagttc t                 351
```

<210> SEQ ID NO 147
<211> LENGTH: 117
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 147

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Tyr Trp Asn Trp Ile Arg Lys Pro Pro Gly Lys Lys Leu Glu Tyr Ile
        35                  40                  45

Gly Tyr Ile Ser Tyr Ser Gly Lys Thr Tyr Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Lys Tyr Asp Tyr Ala Met Asp Tyr Trp Gly Gln Gly Thr Leu
            100                 105                 110

Val Thr Val Ser Ser
        115
```

<210> SEQ ID NO 148
<211> LENGTH: 333
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 148

```
gatatcgtta tgacccagag cccacttagt ttgcctgtta ctcctggcga gcctgccagt        60
atttcttgcc gtgctagcga aatcgtggat aactttggta tatcattcat gaattggtat       120
ctccaaaaac ctggccaaag cccccagctc cttatctacg ccgctagcaa ccagggtcc        180 ggggtacctg atagattttc aggcagcggc tctggaaccg acttcacact gaagatttcc       240
cgggtggagg ccgaggacgt gggcgtgtac tattgtcaac agtccaagga agtccctccc       300
actttcggcg gtgggacaaa ggttgagatt aag                                    333
```

<210> SEQ ID NO 149
<211> LENGTH: 111
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 149

```
Asp Ile Val Met Thr Gln Ser Pro Leu Ser Leu Pro Val Thr Pro Gly
1               5                   10                  15

Glu Pro Ala Ser Ile Ser Cys Arg Ala Ser Glu Ile Val Asp Asn Phe
            20                  25                  30
```

```
Gly Ile Ser Phe Met Asn Trp Tyr Leu Gln Lys Pro Gly Gln Ser Pro
                35                  40                  45

Gln Leu Leu Ile Tyr Ala Ala Ser Asn Gln Gly Ser Gly Val Pro Asp
         50                  55                  60

Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Gln Gln Ser Lys
                 85                  90                  95

Glu Val Pro Pro Thr Phe Gly Gly Gly Thr Lys Val Glu Ile Lys
            100                 105                 110

<210> SEQ ID NO 150
<211> LENGTH: 990
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150
gcctcaacaa aaggaccaag tgtgttccca ctcgccccta gcagcaagag tacatccggg     60
ggcactgcag cactcggctg cctcgtcaag gattattttc cagagccagt aaccgtgagc    120
tggaacagtg agcactcac ttctggtgtc catactttc ctgctgtcct gcaaagctct      180
ggcctgtact cactcagctc cgtcgtgacc gtgccatctt catctctggg cactcagacc    240
tacatctgta atgtaaacca caagcctagc aatactaagg tcgataagcg ggtggaaccc    300
aagagctgcg acaagactca cacttgtccc ccatgccctg cccctgaact tctgggcggt    360
cccagcgtct ttttgttccc accaaagcct aaagatactc tgatgataag tagaacaccc    420
gaggtgacat gtgttgttgt agacgtttcc cacgaggacc cagaggttaa gttcaactgg    480
tacgttgatg gagtcgaagt acataatgct aagaccaagc ctagagagga gcagtataat    540
agtacatacc gtgtagtcag tgttctcaca gtgctgcacc aagactggct caacggcaaa    600
gaatacaaat gcaaagtgtc caacaaagca ctcccagccc ctatcgagaa gactattagt    660
aaggcaaagg ggcagcctcg tgaaccacag gtgtacactc tgccacccag tagagaggaa    720
atgacaaaga accaagtctc attgacctgc ctggtgaaag cttctaccc cagcgacatc    780 gccgttgagt gggagagtaa cggtcagcct gagaacaatt acaagacaac cccccagtg    840 ctggatagtg acgggtcttt ctttctgtac agtaagctga ctgtggacaa gtcccgctgg    900
cagcagggta acgtcttcag ctgttccgtg atgcacgagg cattgcacaa ccactacacc    960
cagaagtcac tgagcctgag cccagggaag                                     990

<210> SEQ ID NO 151
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

```
              35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 152
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152
cgcacagtcg ccgctccctc cgtgttcatc tttccaccaa gtgatgagca actgaagtct    60
ggtactgctt cagtcgtgtg tctgctgaac aatttctacc ctcgagaagc caaagtccaa   120
tggaaggtag acaacgcact gcagtccggc aatagccaag atcagttac cgaacaggat    180 tcaaaggaca gtacatattc cctgagcagc actctgaccc tgtcaaaggc cgattacgag   240
aaacacaagg tctatgcttg cgaagtgaca catcagggac tgtccagccc agtgacaaaa   300
tcttttaacc gtggggagtg t                                             321
```

<210> SEQ ID NO 153
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 153
cgcacagttg ctgcccccag cgtgttcatt ttcccaccta gcgatgagca gctgaaaagc    60
ggtactgcct ctgtcgtatg cttgctcaac aactttacc cacgtgaggc taaggtgcag   120
tggaaagtgg ataatgcact tcaatctgga aacagtcaag agtccgtgac agaacaggac   180
agcaaagact caacttattc actctcttcc accctgactc tgtccaaggc agactatgaa   240
aaacacaagg tatacgcctg cgaggttaca caccagggtt tgtctagtcc tgtcaccaag   300
tccttcaata ggggcgaatg t                                             321

<210> SEQ ID NO 154
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 155
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 155
gaggtgaagc ttctcgagtc tggaggtggc ctggtgcagc cgggtggatc cctgaaactc    60
tcctgtgcag cctcaggatt cgattttagt agacactgga tgagttgggt ccggctggct   120
ccagggaaag gctagaatg gatcgcagaa attaatccag atagcagaac gataaactat   180
acgccatctc taaggagaa attcatcatc tccagagaca cgccaaaaa ttcgctgttt   240 ctgcaaatga acagagtgag atctgaggac acagcccttt attactgtgc aagacgggta   300
agaattcatt actacggcgc tatggacagc tggggtcaag aacctcagt caccgtctcc   360 tcagcctcaa caaaggacc aagtgtgttc ccactcgccc ctagcagcaa gagtacatcc   420

```
gggggcactg cagcactcgg ctgcctcgtc aaggattatt ttccagagcc agtaaccgtg    480
agctggaaca gtggagcact cacttctggt gtccatactt ttcctgctgt cctgcaaagc    540
tctggcctgt actcactcag ctccgtcgtg accgtgccat cttcatctct gggcactcag    600
acctacatct gtaatgtaaa ccacaagcct agcaatacta aggtcgataa gcgggtggaa    660
cccaagagct gcgacaagac tcacacttgt cccccatgcc ctgcccctga acttctgggc    720
ggtcccagcg tcttttttgtt cccaccaaag cctaaagata tctgatgat aagtagaaca    780 cccgaggtga catgtgttgt tgtagacgtt tcccacgagg acccagaggt taagttcaac    840
tggtacgttg atggagtcga agtacataat gctaagacca agcctagaga ggagcagtat    900
aatagtacat accgtgtagt cagtgttctc acagtgctgc accaagactg gctcaacggc    960
aaagaataca aatgcaaagt gtccaacaaa gcactcccag cccctatcga aagactatt    1020 agtaaggcaa aggggcagcc tcgtgaacca caggtgtaca ctctgccacc cagtagagag   1080
gaaatgacaa agaaccaagt ctcattgacc tgcctggtga aaggcttcta ccccagcgac   1140
atcgccgttg agtgggagag taacggtcag cctgagaaca attacaagac aacccccca   1200 gtgctggata tgacgggtc tttctttctg tacagtaagc tgactgtgga caagtcccgc   1260
tggcagcagg gtaacgtctt cagctgttcc gtgatgcacg aggcattgca caaccactac   1320
acccagaagt cactgagcct gagcccaggg aag                                1353
```

<210> SEQ ID NO 156
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 156

```
Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg His
            20                  25                  30

Trp Met Ser Trp Val Arg Leu Ala Pro Gly Lys Gly Leu Glu Trp Ile
        35                  40                  45

Ala Glu Ile Asn Pro Asp Ser Arg Thr Ile Asn Tyr Thr Pro Ser Leu
    50                  55                  60

Lys Glu Lys Phe Ile Ile Ser Arg Asp Asn Ala Lys Asn Ser Leu Phe
65                  70                  75                  80

Leu Gln Met Asn Arg Val Arg Ser Glu Asp Thr Ala Leu Tyr Tyr Cys
                85                  90                  95

Ala Arg Arg Val Arg Ile His Tyr Tyr Gly Ala Met Asp Ser Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
            245                 250                 255
Ile Ser Arg Thr Pro Glu Val Thr Cys Val Val Val Asp Val Ser His
        260                 265                 270
Glu Asp Pro Glu Val Lys Phe Asn Trp Tyr Val Asp Gly Val Glu Val
    275                 280                 285
His Asn Ala Lys Thr Lys Pro Arg Glu Glu Gln Tyr Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
            325                 330                 335
Glu Lys Thr Ile Ser Lys Ala Lys Gly Gln Pro Arg Glu Pro Gln Val
        340                 345                 350
Tyr Thr Leu Pro Pro Ser Arg Glu Glu Met Thr Lys Asn Gln Val Ser
    355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
            405                 410                 415
Asp Lys Ser Arg Trp Gln Gln Gly Asn Val Phe Ser Cys Ser Val Met
        420                 425                 430
His Glu Ala Leu His Asn His Tyr Thr Gln Lys Ser Leu Ser Leu Ser
    435                 440                 445
Pro Gly Lys
    450

<210> SEQ ID NO 157
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157
gacattgtgt tgacccagtc tcaaaaaatc gtgtccacat cagtaggagc cagggtcagc      60
gtcacctgca aggccagtca gaatgtgggt tctagtttag tctggtatca acagaaacca     120
ggtcaatctc ctaaaacact gatttactcg gcatccttcc ggtacagtgg agtccctgat     180
cgcttcacag gcagtggatc tgggacagat tcactctcac catcagcaa tgtgcagtct     240 gaagacttgg cagattattt ctgtcaacaa tataataact atccgctcac gttcggtgct     300
gggaccaagc tggagctgaa acgcacagtc gccgctccct ccgtgttcat ctttccacca     360
agtgatgagc aactgaagtc tggtactgct cagtcgtgt gtctgctgaa caatttctac     420
cctcgagaag ccaaagtcca atggaaggta gacaacgcac tgcagtccgg caatagccaa     480
```

```
gaatcagtta ccgaacagga ttcaaaggac agtacatatt ccctgagcag cactctgacc      540
ctgtcaaagg ccgattacga gaaacacaag gtctatgctt gcgaagtgac acatcaggga      600
ctgtccagcc cagtgacaaa atcttttaac cgtggggagt gt                         642
```

<210> SEQ ID NO 158
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

```
Asp Ile Val Leu Thr Gln Ser Gln Lys Ile Val Ser Thr Ser Val Gly
1               5                   10                  15

Ala Arg Val Ser Val Thr Cys Lys Ala Ser Gln Asn Val Gly Ser Ser
            20                  25                  30

Leu Val Trp Tyr Gln Gln Lys Pro Gly Gln Ser Pro Lys Thr Leu Ile
        35                  40                  45

Tyr Ser Ala Ser Phe Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Asn Tyr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 159
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 159

```
gaggtgcagc ttcaggagtc aggacctagc ctcgtgaaac cttctcagac tctgtccctc      60
acctgttctg tcactggcga ctccatcacc agtggttact ggaactggat ccggaaattc      120
ccagggaata aacttgagta catgggggtac ataagctaca gtggtaaaac ttactacaat     180
ccatctctca aaagtcgaat ctccatcact cgagacacat ccaagaacca ttactacctg     240
cagttgattt ctgtgactgc tgaggacaca gccacatatt actgtgcaag gtctaagtac     300
```

```
gactatgcta tggactactg gggtcaagga acctcagtca ccgtctcctc agcctcaaca    360
aaaggaccaa gtgtgttccc actcgcccct agcagcaaga gtacatccgg ggcactgca    420
gcactcggct gcctcgtcaa ggattatttt ccagagccag taaccgtgag ctggaacagt    480
ggagcactca cttctggtgt ccatactttt cctgctgtcc tgcaaagctc tggcctgtac    540
tcactcagct ccgtcgtgac cgtgccatct tcatctctgg cactcagac ctacatctgt    600
aatgtaaacc acaagcctag caatactaag gtcgataagc gggtggaacc caagagctgc    660
gacaagactc acacttgtcc cccatgccct gcccctgaac ttctgggcgg tcccagcgtc    720
tttttgttcc caccaaagcc taaagatact ctgatgataa gtagaacacc cgaggtgaca    780
tgtgttgttg tagacgtttc ccacgaggac ccagaggtta agttcaactg gtacgttgat    840
ggagtcgaag tacataatgc taagaccaag cctagagagg agcagtataa tagtacatac    900
cgtgtagtca gtgttctcac agtgctgcac caagactggc tcaacggcaa agaatacaaa    960
tgcaaagtgt ccaacaaagc actcccagcc cctatcgaga agactattag taaggcaaag   1020
gggcagcctc gtgaaccaca ggtgtacact ctgccaccca gtagagagga aatgacaaag   1080
aaccaagtct cattgacctg cctggtgaaa ggcttctacc ccagcgacat cgccgttgag   1140
tgggagagta acggtcagcc tgagaacaat tacaagacaa ccccccccagt gctggatagt   1200
gacgggtctt tctttctgta cagtaagctg actgtggaca gtcccgctg cagcagggt    1260
aacgtcttca gctgttccgt gatgcacgag gcattgcaca accactacac ccagaagtca   1320
ctgagcctga gcccagggaa g                                              1341
```

<210> SEQ ID NO 160
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Lys Thr Tyr Tyr Asn Pro Ser Leu Lys
    50                  55                  60

Ser Arg Ile Ser Ile Thr Arg Asp Thr Ser Lys Asn His Tyr Tyr Leu
65                  70                  75                  80

Gln Leu Ile Ser Val Thr Ala Glu Asp Thr Ala Thr Tyr Tyr Cys Ala
                85                  90                  95

Arg Ser Lys Tyr Asp Tyr Ala Met Asp Tyr Trp Gly Gln Gly Thr Ser
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser

```
            165                 170                 175
Ser Gly Leu Tyr Ser Leu Ser Val Val Thr Val Pro Ser Ser
        180                 185                 190
Leu Gly Thr Gln Thr Tyr Ile Cys Asn Val Asn His Lys Pro Ser Asn
    195                 200                 205
Thr Lys Val Asp Lys Arg Val Glu Pro Lys Ser Cys Asp Lys Thr His
210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 161
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161
gacattgtgc tgacccaatc tccagcttct ttggctgtgt ctctaggaca gagggccacc      60
atctcctgca gagccagcga aattgttgat aattttggca ttagttttat gaactggttc     120
caacagaaac caggacagcc acccaaactc ctcatctatg ctgcatccaa ccaaggatcc     180
ggggtccctg ccaggtttag tggcagtggg tctgggacag acttcagcct caacatccat     240
cctgtggagg aggatgatac tgcaatgtat ttctgtcagc aaagtaagga ggttcctccg     300
acgttcggtg aggcaccaa gctggaaatc aaacgcacag tcgccgctcc ctccgtgttc     360
atctttccac caagtgatga gcaactgaag tctggtactg cttcagtcgt gtgtctgctg     420
aacaatttct accctcgaga agccaaagtc aatggaagg tagacaacgc actgcagtcc     480
```

```
ggcaatagcc aagaatcagt taccgaacag gattcaaagg acagtacata ttccctgagc    540
agcactctga ccctgtcaaa ggccgattac gagaaacaca aggtctatgc ttgcgaagtg    600
acacatcagg gactgtccag cccagtgaca aaatctttta accgtgggga gtgt          654
```

```
<210> SEQ ID NO 162
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162
```

```
Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ile Val Asp Asn Phe
             20                  25                  30

Gly Ile Ser Phe Met Asn Trp Phe Gln Gln Lys Pro Gly Gln Pro Pro
         35                  40                  45

Lys Leu Leu Ile Tyr Ala Ala Ser Asn Gln Gly Ser Gly Val Pro Ala
     50                  55                  60

Arg Phe Ser Gly Ser Gly Ser Gly Thr Asp Phe Ser Leu Asn Ile His
 65                  70                  75                  80

Pro Val Glu Glu Asp Asp Thr Ala Met Tyr Phe Cys Gln Gln Ser Lys
                 85                  90                  95

Glu Val Pro Pro Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

```
<210> SEQ ID NO 163
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 163
```

```
gaggttcagc tggtagaatc cggaggaggg ttggtccaac ctggtggatc actcagactt    60
tcatgcgccg ccagcggctt tgacttctca cgacattgga tgagctgggt ccggcaggct    120
ccaggcaagg gcctcgagtg ggttagcgag atcaatccag acagcagaac cattaactat    180
acacccagtc tgaaggagcg gttcaccata agccgtgata atgccaagaa ctccctgtac    240
```

```
ttgcagatga actccttgcg cgctgaagat acagctgtgt actattgtgc aaggcgcgtg    300
cgaatccact attacggggc aatggattct tggggccagg gtactaccgt gactgtgagt    360
tctgcctcaa caaaaggacc aagtgtgttc ccactcgccc ctagcagcaa gagtacatcc    420
gggggcactg cagcactcgg ctgcctcgtc aaggattatt ttccagagcc agtaaccgtg    480
agctggaaca gtggagcact cacttctggt gtccatactt ttcctgctgt cctgcaaagc    540
tctggcctgt actcactcag ctccgtcgtg accgtgccat cttcatctct gggcactcag    600
acctacatct gtaatgtaaa ccacaagcct agcaatacta aggtcgataa gcgggtggaa    660
cccaagagct gcgacaagac tcacacttgt cccccatgcc ctgcccctga acttctgggc    720
ggtcccagcg tcttttttgtt cccaccaaag cctaaagata ctctgatgat aagtagaaca    780
cccgaggtga catgtgttgt tgtagacgtt cccacgagg acccagaggt taagttcaac    840
tggtacgttg atggagtcga agtacataat gctaagacca gcctagaga ggagcagtat    900
aatagtacat accgtgtagt cagtgttctc acagtgctgc accaagactg gctcaacggc    960
aaagaataca aatgcaaagt gtccaacaaa gcactcccag cccctatcga aagactatt    1020
agtaaggcaa aggggcagcc tcgtgaacca caggtgtaca ctctgccacc cagtagagag    1080
gaaatgacaa agaaccaagt ctcattgacc tgcctggtga aaggcttcta ccccagcgac    1140
atcgccgttg agtgggagag taacggtcag cctgagaaca attacaagac aaccccccca    1200
gtgctggata tgacgggtc tttcttctg tacagtaagc tgactgtgga caagtcccgc    1260
tggcagcagg gtaacgtctt cagctgttcc gtgatgcacg aggcattgca caaccactac    1320
acccagaagt cactgagcct gagcccaggg aag                                1353
```

<210> SEQ ID NO 164
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 164

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg His
            20                  25                  30

Trp Met Ser Trp Val Arg Gln Ala Pro Gly Lys Gly Leu Glu Trp Val
        35                  40                  45

Ser Glu Ile Asn Pro Asp Ser Arg Thr Ile Asn Tyr Thr Pro Ser Leu
    50                  55                  60

Lys Glu Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Val Arg Ile His Tyr Tyr Gly Ala Met Asp Ser Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

```
Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 165
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 165
gaggttcagc tggtagaatc cggaggaggg ttggtccaac tggtggatc actcagactt      60 tcatgcgccg ccagcggctt taccttctca cgacattgga tgagctgggt ccggcaggct    120
ccaggcaagg gcctcgagtg ggttagcgag atcaatccag acagcagaac cattaactat    180
gcccccagtg tgaagggccg gttcaccata agccgtgata atgccaagaa ctccctgtac    240
ttgcagatga actccttgcg cgctgaagat acagctgtgt actattgtgc aaggcgcgtg    300
cgaatccact attacggggc aatggattct tggggccagg gtactaccgt gactgtgagt    360
```

```
tctgcctcaa caaaaggacc aagtgtgttc ccactcgccc ctagcagcaa gagtacatcc      420
gggggcactg cagcactcgg ctgcctcgtc aaggattatt ttccagagcc agtaaccgtg      480
agctggaaca gtggagcact cacttctggt gtccatactt ttcctgctgt cctgcaaagc      540
tctggcctgt actcactcag ctccgtcgtg accgtgccat cttcatctct gggcactcag      600
acctacatct gtaatgtaaa ccacaagcct agcaatacta aggtcgataa gcgggtggaa      660
cccaagagct gcgacaagac tcacacttgt cccccatgcc ctgcccctga acttctgggc      720
ggtcccagcg tcttttttgtt cccaccaaag cctaaagata ctctgatgat aagtagaaca      780
cccgaggtga catgtgttgt tgtagacgtt tcccacgagg acccagaggt taagttcaac      840
tggtacgttg atggagtcga agtacataat gctaagacca agcctagaga ggagcagtat      900
aatagtacat accgtgtagt cagtgttctc acagtgctgc accaagactg gctcaacggc      960
aaagaataca aatgcaaagt gtccaacaaa gcactcccag cccctatcga aagactatt     1020 agtaaggcaa aggggcagcc tcgtgaacca caggtgtaca ctctgccacc cagtagagag     1080
gaaatgacaa agaaccaagt ctcattgacc tgcctggtga aaggcttcta ccccagcgac     1140
atcgccgttg agtgggagag taacggtcag cctgagaaca attacaagac aaccccccca     1200
gtgctggata tgacgggtc tttctttctg tacagtaagc tgactgtgga caagtcccgc     1260
tggcagcagg gtaacgtctt cagctgttcc gtgatgcacg aggcattgca caaccactac     1320
acccagaagt cactgagcct gagcccaggg aag                                  1353
```

<210> SEQ ID NO 166
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg His
            20                  25                  30

Trp Met Ser Trp Val Arg Gln Ala Pro Gly Lys Gly Leu Glu Trp Val
        35                  40                  45

Ser Glu Ile Asn Pro Asp Ser Arg Thr Ile Asn Tyr Ala Pro Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Val Arg Ile His Tyr Tyr Gly Ala Met Asp Ser Trp Gly
            100                 105                 110

Gln Gly Thr Thr Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 167
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 167
gatatccagt tgactcagtc tcagtccttt gtgagtacat cagtgggcga cagggtcacc      60
gtgacctgcc gagcatcaca gaacgttgga agctctcttg tctggtatca gcaaaagcct     120
gggaagagcc ccaaaaccct catctattct gcttcctttc tgtactccgg cgtaccaagt     180
agattctctg gtagcggatc cgggacagag ttcactctca aattagcagt gtgcagcct      240 gaggatttcg ccgactactt ctgtcagcaa tacaataact atccctgac ttttggtggc      300 ggcaccaaag tggaaatcaa gcgcacagtt gctgccccca gcgtgttcat ttttcccacct    360 agcgatgagc agctgaaaag cggtactgcc tctgtcgtat gcttgctcaa caactttac    420

```
ccacgtgagg ctaaggtgca gtggaaagtg ataatgcac ttcaatctgg aaacagtcaa      480
gagtccgtga cagaacagga cagcaaagac tcaacttatt cactctcttc caccctgact     540
ctgtccaagg cagactatga aaaacacaag gtatacgcct gcgaggttac acaccagggt    600
ttgtctagtc ctgtcaccaa gtccttcaat aggggcgaat gt                        642
```

<210> SEQ ID NO 168
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 168

```
Asp Ile Gln Leu Thr Gln Ser Gln Ser Phe Val Ser Thr Ser Val Gly
1               5                   10                  15

Asp Arg Val Thr Val Thr Cys Arg Ala Ser Gln Asn Val Gly Ser Ser
            20                  25                  30

Leu Val Trp Tyr Gln Gln Lys Pro Gly Lys Ser Pro Lys Thr Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Glu Phe Thr Leu Thr Ile Ser Ser Val Gln Pro
65                  70                  75                  80

Glu Asp Phe Ala Asp Tyr Phe Cys Gln Gln Tyr Asn Asn Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 169
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 169

```
gacattcagc tgactcagtc gccgtcgttt tgtcggcgt ccgtgggtga cagagtgact      60
atcacatgtc gcgcttcgca aaacgtcgga tcatcgcttg tgtggtatca gcagaaaccc    120
ggtaaagccc ctaagaccct catctattca gcgtcatttc tgtatagcgg ggtcccctca    180
cggttcagcg gatccggctc cgggaccgag ttcacactca ctatttcgag cttgcagccg    240
```

```
gaagattttg caacgtacta ctgccagcaa tacaataact acccactcac gttcggaggg      300
ggaacgaagg tagagatcaa gcgcacagtt gctgccccca gcgtgttcat tttcccacct      360
agcgatgagc agctgaaaag cggtactgcc tctgtcgtat gcttgctcaa caacttttac      420
ccacgtgagg ctaaggtgca gtggaaagtg gataatgcac ttcaatctgg aaacagtcaa      480
gagtccgtga cagaacagga cagcaaagac tcaacttatt cactctcttc caccctgact      540
ctgtccaagg cagactatga aaaacacaag gtatacgcct gcgaggttac acaccagggt      600
ttgtctagtc ctgtcaccaa gtccttcaat aggggcgaat gt                        642
```

<210> SEQ ID NO 170
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 170

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Asn Val Gly Ser Ser
            20                  25                  30

Leu Val Trp Tyr Gln Lys Pro Gly Lys Ala Pro Lys Thr Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 171
<211> LENGTH: 1341
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 171

```
caagttcagc tgcaagaatc cggaccagga ttggtcaaac cttcagagac actcagcctg      60
acttgcaccg tgagcggtgg cagcatatcc tccggttatt ggaactggat ccggcagcca     120
ccaggcaagg gcctcgagtg gattggctac atcagctata gcgggaaaac ctattacaac     180
cccagtctga agagccgagt gaccataagc gtcgatacaa gtaagaacca gttctccctg     240
aagctctcat ccgtgaccgc cgctgataca gctgtgtact attgtgcaag gtcaaagtat     300
gactacgcaa tggactattg gggccagggt actctggtga ctgtgagttc tgcctcaaca     360
aaaggaccaa gtgtgttccc actcgcccct agcagcaaga gtacatccgg gggcactgca     420
gcactcggct gcctcgtcaa ggattatttt ccagagccag taaccgtgag ctggaacagt     480
ggagcactca cttctggtgt ccatactttt cctgctgtcc tgcaaagctc tggcctgtac     540
tcactcagct ccgtcgtgac cgtgccatct tcatctctgg gcactcagac ctacatctgt     600
aatgtaaacc acaagcctag caatactaag gtcgataagc gggtggaacc caagagctgc     660
gacaagactc acacttgtcc cccatgccct gcccctgaac ttctgggcgg tcccagcgtc     720
tttttgttcc caccaaagcc taaagatact ctgatgataa gtagaacacc cgaggtgaca     780
tgtgttgttg tagacgtttc ccacgaggac ccagaggtta agttcaactg gtacgttgat     840
ggagtcgaag tacataatgc taagaccaag cctagagagg agcagtataa tagtacatac     900
cgtgtagtca gtgttctcac agtgctgcac caagactggc tcaacggcaa agaatacaaa     960
tgcaaagtgt ccaacaaagc actcccagcc cctatcgaga agactattag taaggcaaag    1020
gggcagcctc gtgaaccaca ggtgtacact ctgccaccca gtagagagga aatgacaaag    1080
aaccaagtct cattgacctg cctggtgaaa ggcttctacc ccagcgacat cgccgttgag    1140
tgggagagta acggtcagcc tgagaacaat tacaagacaa cccccccagt gctggatagt    1200
gacgggtctt tctttctgta cagtaagctg actgtggaca agtcccgctg gcagcagggt    1260
aacgtcttca gctgttccgt gatgcacgag gcattgcaca accactacac ccagaagtca    1320
ctgagcctga gcccagggaa g                                              1341
```

```

<210> SEQ ID NO 172
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Tyr Trp Asn Trp Ile Arg Gln Pro Pro Gly Lys Gly Leu Glu Trp Ile
        35                  40                  45

Gly Tyr Ile Ser Tyr Ser Gly Lys Thr Tyr Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Lys Tyr Asp Tyr Ala Met Asp Tyr Trp Gly Gln Gly Thr Leu
            100                 105                 110

Val Thr Val Ser Ser Ala Ser Thr Lys Gly Pro Ser Val Phe Pro Leu
```

```
                  115                 120                 125
Ala Pro Ser Ser Lys Ser Thr Ser Gly Gly Thr Ala Ala Leu Gly Cys
            130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Arg Val Glu Pro Lys Ser Cys Asp Lys Thr His
210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 173
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 173
caagttcagc tgcaagaatc cggaccagga ttggtcaaac ccagcgaaac actctctctt      60
acatgcaccg tgagcggcga ctctatcacc tcagggtatt ggaattggat tcggaaaccc    120
ccaggcaaga agctcgagta catgggttac atcagttaca gcgggaaaac ctactataac    180
```

```
cccagtctga agagcagaat caccataagc cgtgatacct ctaagaacca gtactccctg      240
aagctgagtt ccgtaacagc agctgataca gctgtgtact attgtgcaag gagtaagtat      300
gactacgcaa tggactattg gggccagggt actcttgtga ctgtgagttc tgcctcaaca      360
aaaggaccaa gtgtgttccc actcgcccct agcagcaaga gtacatccgg ggcactgca       420 gcactcggct gcctcgtcaa ggattatttt ccagagccag taaccgtgag ctggaacagt      480
ggagcactca cttctggtgt ccatactttt cctgctgtcc tgcaaagctc tggcctgtac      540
tcactcagct ccgtcgtgac cgtgccatct tcatctctgg gcactcagac ctacatctgt      600
aatgtaaacc acaagcctag caatactaag gtcgataagc gggtggaacc caagagctgc      660
gacaagactc acacttgtcc cccatgccct gcccctgaac ttctgggcgg tcccagcgtc      720 ttttgttcc caccaaagcc taaagatact ctgatgataa gtagaacacc cgaggtgaca       780
tgtgttgttg tagacgtttc ccacgaggac ccagaggtta agttcaactg gtacgttgat      840
ggagtcgaag tacataatgc taagaccaag cctagagagg agcagtataa tagtacatac      900
cgtgtagtca gtgttctcac agtgctgcac caagactggc tcaacggcaa agaatacaaa      960
tgcaaagtgt ccaacaaagc actcccagcc cctatcgaga agactattag taaggcaaag     1020
gggcagcctc gtgaaccaca ggtgtacact ctgccaccca gtagagagga atgacaaag     1080 aaccaagtct cattgacctg cctggtgaaa ggcttctacc ccagcgacat cgccgttgag     1140
tgggagagta acggtcagcc tgagaacaat tacaagacaa ccccccccagt gctggatagt    1200 gacgggtctt tctttctgta cagtaagctg actgtggaca agtcccgctg cagcagggt     1260 aacgtcttca gctgttccgt gatgcacgag gcattgcaca accactacac ccagaagtca    1320
ctgagcctga gcccagggaa g                                               1341

<210> SEQ ID NO 174
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Gly
            20                  25                  30

Tyr Trp Asn Trp Ile Arg Lys Pro Pro Gly Lys Lys Leu Glu Tyr Met
        35                  40                  45

Gly Tyr Ile Ser Tyr Ser Gly Lys Thr Tyr Tyr Asn Pro Ser Leu Lys
    50                  55                  60

Ser Arg Ile Thr Ile Ser Arg Asp Thr Ser Lys Asn Gln Tyr Ser Leu
65                  70                  75                  80

Lys Leu Ser Ser Val Thr Ala Ala Asp Thr Ala Val Tyr Tyr Cys Ala
                85                  90                  95

Arg Ser Lys Tyr Asp Tyr Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
```

```
                145                 150                 155                 160
Gly Ala Leu Thr Ser Gly Val His Thr Phe Pro Ala Val Leu Gln Ser
                    165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 175
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 175
caagttcagc tgcaagaatc cggaccagga ttggtcaaac cttcagagac actcagcctg       60
acttgcaccg tgagcggtgg cagcatatcc tccggttatt ggaactggat ccggaagcca      120
ccaggcaaga agctcgagta cattggctac atcagctata gcgggaaaac ctattacaac      180
cccagtctga gagccgagt gaccataagc aggatacaa gtaagaaccca gttctccctg      240 aagctctcat ccgtgaccgc cgctgataca gctgtgtact attgtgcaag gtcaaagtat      300
gactacgcaa tggactattg gggccagggt actctggtga ctgtgagttc tgcctcaaca      360
```

```
aaaggaccaa gtgtgttccc actcgcccct agcagcaaga gtacatccgg gggcactgca    420
gcactcggct gcctcgtcaa ggattatttt ccagagccag taaccgtgag ctggaacagt    480
ggagcactca cttctggtgt ccatactttt cctgctgtcc tgcaaagctc tggcctgtac    540
tcactcagct ccgtcgtgac cgtgccatct tcatctctgg gcactcagac ctacatctgt    600
aatgtaaacc acaagcctag caatactaag gtcgataagc gggtggaacc caagagctgc    660
gacaagactc acacttgtcc cccatgcccT gcccctgaac ttctgggcgg tcccagcgtc    720
tttttgttcc caccaaagcc taaagatact ctgatgataa gtagaacacc cgaggtgaca    780
tgtgttgttg tagacgtttc ccacgaggac ccagaggtta agttcaactg gtacgttgat    840
ggagtcgaag tacataatgc taagaccaag cctagagagg agcagtataa tagtacatac    900
cgtgtagtca gtgttctcac agtgctgcac caagactggc tcaacggcaa agaatacaaa    960
tgcaaagtgt ccaacaaagc actcccagcc cctatcgaga agactattag taaggcaaag   1020
gggcagcctc gtgaaccaca ggtgtacact ctgccaccca gtagagagga aatgacaaag   1080
aaccaagtct cattgacctg cctggtgaaa ggcttctacc ccagcgacat cgccgttgag   1140
tgggagagta acggtcagcc tgagaacaat tacaagacaa ccccccccagt gctggatagt   1200
gacgggtctt tctttctgta cagtaagctg actgtggaca gtcccgctg gcagcagggt   1260
aacgtcttca gctgttccgt gatgcacgag gcattgcaca accactacac ccagaagtca   1320
ctgagcctga gcccagggaa g                                             1341
```

<210> SEQ ID NO 176
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 176

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Tyr Trp Asn Trp Ile Arg Lys Pro Pro Gly Lys Lys Leu Glu Tyr Ile
        35                  40                  45

Gly Tyr Ile Ser Tyr Ser Gly Lys Thr Tyr Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Lys Tyr Asp Tyr Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
```

```
            180                 185                 190
Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 177
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 177
gatatcgtta tgacccagag cccacttagt ttgcctgtta ctcctggcga gcctgccagt    60
atttcttgcc gtgctagcga atcgtggat aactttggta tatcattcat gaattggtat    120
ctccaaaaac ctggccaaag cccccagctc cttatctacg ccgctagcaa ccaggggtcc    180
ggggtacctg atagattttc aggcagcggc tctggaaccg acttcacact gaagatttcc    240
cgggtggagg ccgaggacgt gggcgtgtac tattgtcaac agtccaagga agtccctccc    300
actttcggcg gtgggacaaa ggttgagatt aagcgcacag ttgctgcccc cagcgtgttc    360
attttcccac ctagcgatga gcagctgaaa agcggtactg cctctgtcgt atgcttgctc    420
aacaactttt acccacgtga ggctaaggtg cagtggaaag tggataatgc acttcaatct    480
ggaaacagtc aagagtccgt gacagaacag gacagcaaag actcaactta ttcactctct    540
```

```
tccaccctga ctctgtccaa ggcagactat gaaaaacaca aggtatacgc ctgcgaggtt      600
acacaccagg gtttgtctag tcctgtcacc aagtccttca atagggcga atgt             654
```

<210> SEQ ID NO 178
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

```
Asp Ile Val Met Thr Gln Ser Pro Leu Ser Leu Pro Val Thr Pro Gly
1               5                   10                  15

Glu Pro Ala Ser Ile Ser Cys Arg Ala Ser Glu Ile Val Asp Asn Phe
            20                  25                  30

Gly Ile Ser Phe Met Asn Trp Tyr Leu Gln Lys Pro Gly Gln Ser Pro
        35                  40                  45

Gln Leu Leu Ile Tyr Ala Ala Ser Asn Gln Gly Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Lys
                85                  90                  95

Glu Val Pro Pro Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```